United States Patent
Trotter et al.

(10) Patent No.: US 7,691,879 B2
(45) Date of Patent: Apr. 6, 2010

(54) ISOQUINOLINE POTASSIUM CHANNEL INHIBITORS

(75) Inventors: B. Wesley Trotter, Glenside, PA (US); Kausik K. Nanda, Norristown, PA (US); Nathan R. Kett, Perkiomenville, NJ (US); Christopher J. Dinsmore, Newton, MA (US); Gerald S. Ponticello, Lansdale, PA (US); David A. Claremon, Maple Glen, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 530 days.

(21) Appl. No.: 10/572,342

(22) PCT Filed: Sep. 17, 2004

(86) PCT No.: PCT/US2004/030486
§ 371 (c)(1),
(2), (4) Date: Mar. 17, 2006

(87) PCT Pub. No.: WO2005/030130
PCT Pub. Date: Apr. 7, 2005

(65) Prior Publication Data
US 2006/0276450 A1 Dec. 7, 2006

Related U.S. Application Data

(60) Provisional application No. 60/505,143, filed on Sep. 23, 2003.

(51) Int. Cl.
*A61K 31/47* (2006.01)
*C07D 217/00* (2006.01)
*C07D 217/22* (2006.01)

(52) U.S. Cl. ............ 514/307; 514/309; 514/310; 546/150; 546/141; 546/143

(58) Field of Classification Search ........... 546/143, 546/141, 150; 514/307, 309, 310
See application file for complete search history.

(56) References Cited

U.S. PATENT DOCUMENTS 4,175,191 A 11/1979 Houlihan et al.

FOREIGN PATENT DOCUMENTS

| EP | 0848000 | 10/2000 |
| JP | 2000 281654 | 10/1997 |
| WO | WO 2004/108681 A1 | 12/2004 |
| WO | WO 2005/020444 | 3/2005 |
| WO | WO 2005/028444 | 3/2005 |

OTHER PUBLICATIONS

Hcaplus 135: 371759.*
Hcaplus 2008:99468, Burgess et. al., (2001), "Chlorotris (triphenylphosphine)-rhodium (I)".*
Hcaplus 1982:527463, Ardabilchi et. al., (1982), "A reinvestigation of the Pictet-Gams isoquinoline synthesis. Part 2. Formation of rearranged isoquinolines: the 2-oxazoline-isoquinoline transformation".*

* cited by examiner

*Primary Examiner*—Janet L Andres
*Assistant Examiner*—Binta M Robinson
(74) *Attorney, Agent, or Firm*—Heidi M. Struse; Mark R. Daniel; Richard S. Parr

(57) ABSTRACT

The present invention relates to compounds having the structure (I) useful as potassium channel inhibitors to treat cardiac arrhythmias, and the like.

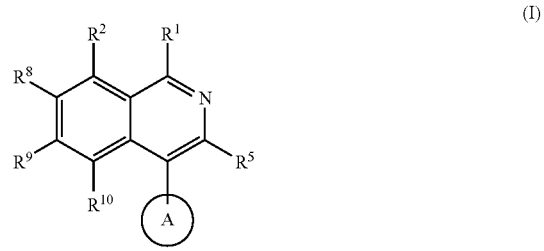

3 Claims, No Drawings

ISOQUINOLINE POTASSIUM CHANNEL INHIBITORS

CROSS REFERENCE TO RELATED APPLICATION

This application is a U.S. National Phase application under 35 U.S.C. § 371 of PCT Application No. PCT/US2004/030480, filed Sep. 17, 2004, which claims priority under 35 U.S.C. § 119(e) from U.S. Provisional Application Ser. No. 60/505,143, filed Sep. 23, 2003.

BACKGROUND OF THE INVENTION

The present invention relates broadly to compounds that are useful as potassium channel inhibitors. Compounds in this class may be useful as Kv1.5 antagonists for treating and preventing cardiac arrhythmias, and the like, and as Kv1.3 inhibitors for treatment of immunosuppression, autoimmune diseases, and the like.

Voltage gated potassium channels (Kv) are multimeric membrane proteins composed of four α subunits and are often associated with accessory β subunits. Kv channels are typically closed at resting membrane potentials, but open upon membrane depolarization. They are involved in the repolarization of the action potential and thus in the electrical excitability of nerve and muscle fibers. The Kv1 class of potassium channels is comprised of at least seven family members, named Kv1.1, Kv1.3, Kv1.5, etc. Functional voltage-gated $K^+$ channels may exist either as homo-oligomers composed of identical subunits, or hetero-oligomers of different subunit composition. This phenomenon is thought to account for the wide diversity of $K^+$ channels. However, subunit compositions of native $K^+$ channels and the physiologic role that particular channels play are, in most cases, still unclear.

The Kv1.3 voltage-gated potassium channel is found in neurons, blood cells, osteoclasts and T-lymphocytes. Membrane depolarization by Kv1.3 inhibition has been shown to be an effective method to prevent T-cell proliferation and therefore has applications in many autoimmune conditions. Inhibition of $K^+$ channels in the plasma membrane of human T-lymphocytes has been postulated to play a role in eliciting immunosuppressive responses by regulating intracellular $Ca^{++}$ homeostasis, which has been found to be important in T-cell activation. Blockade of the Kv1.3 channel has been proposed as a novel mechanism for eliciting an immunosuppressant response (Chandy et al., *J. Exp. Med.* 160: 369, 1984; Decoursey et al., *Nature,* 307: 465, 1984). However, the $K^+$ channel blockers employed in these early studies were nonselective. In later studies, Margatoxin, which blocks only Kv1.3 in T-cells, was shown to exhibit immunosuppressant activity in both in vitro and in vivo models. (Lin et al., *J. Exp. Med,* 177: 637, 1993). The therapeutic utility of this compound, however, is limited by its potent toxicity. Recently, a class of compounds has been reported that may be an attractive alternative to the above-mentioned drugs (U.S. Pat. Nos. 5,670,504; 5,631,282; 5,696,156; 5,679,705; and 5,696,156). While addressing some of the activity/toxicity problems of previous drugs, these compounds tend to be of large molecular weight and are generally produced by synthetic manipulation of a natural product, isolation of which is cumbersome and labor intensive Atrial fibrillation (AF) is the most common sustained cardiac arrhythmia in clinical practice and is likely to increase in prevalence with the aging of the population. Conservative estimates indicate that AF affects >2 million Americans, represents over 5% of all admissions for cardiovascular diseases and leads to a 3- to 5-fold increase in the risk of stroke (Kannel et al, *Am. J. Cardiol.,* 82:2N-9 N, 1998). While AF is rarely fatal, it can impair cardiac function and lead to complications such as the development of congestive heart failure, thromboembolism, or ventricular fibrillation.

Reentrant excitation (reentry) has been shown to be a prominent mechanism underlying supraventricular arrhythmias in man (Nattel, S., *Nature,* 415:219-226, 2002). Reentrant excitation requires a critical balance between slow conduction velocity and sufficiently brief refractory periods to allow for the initiation and maintenance of multiple reentry circuits to coexist simultaneously and sustain AF. Increasing myocardial refractoriness by prolonging action potential duration (APD) prevents and/or terminates reentrant arrhythmias. Action potential duration is determined by the contributions of the repolarizing potassium currents $I_{Kr}$, $I_{Ks}$, and $I_{Kur}$, and the transient outward current, $I_{to}$. Blockers of any one of these currents would therefore be expected to increase the APD and produce antiarrhythmic effects.

Currently available antiarrhythmic agents have been developed for the treatment of ventricular and atrial/supraventricular arrhythmias. Malignant ventricular arrhythmias are immediately, life-threatening and require emergency care. Drug therapy for ventricular arrhythmia includes Class Ia (eg. procainamide, quinidine), Class Ic (eg. flecainide, propafenone), and Class III (amiodarone) agents, which pose significant risks of proarrhythmia. These Class I and III drugs have been shown to convert AF to sinus rhythm and to prevent recurrence of AF (Mounsey, J P, Demarked, J P, *Circulation,* 102:2665-2670), but pose an unacceptable risk of potentially lethal ventricular proarrhythmia and thus may increase mortality (Pratt, C M, Moye, L A, *Am J. Cardiol.,* 65:20B-29B, 1990; Waldo et al, *Lancet,* 348:7-12, 1996; Torp-Pedersen et al, *Expert Opin. Invest. Drugs,* 9:2695-2704, 2000). These observations demonstrate a clear unmet medical need to develop safer and more efficacious drugs for the treatment of atrial arrhythmias.

Class III antiarrhythmic agents cause a selective prolongation of the APD without significant depression of cardiac conduction or contractile function. The only selective Class III drug approved for clinical use in atrial fibrillation is dofetilide, which mediates its anti-arrhythmic effects by blocking $I_{Kr}$, the rapidly activating component of $I_K$ found in both atrium and ventricle in humans (Mounsey, J P, DiMarco, J P, *Circulation,* 102:2665-2670). Since $I_{Kr}$ blockers increase APD and refractoriness both in atria and ventricle without affecting conduction per se, theoretically they represent potentially useful agents for the treatment of arrhythmias like AF (Torp-Pedersen, et al, *Expert Opin. Invest. Drugs,* 9:2695-2704, 2000). However, these agents have the major liability of an enhanced risk of proarrhythmia at slow heart rates. For example, torsades de points has been observed when these compounds are utilized (Roden, D. M. "Current Status of Class III Antiarrhythmia Dug Therapy", Am. J. Cardiol., 72:44B49B, 1993). This exaggerated effect at slow heart rates has been termed "reverse frequency-dependence", and is in contrast to frequency-independent or forward frequency-dependent actions (Hondeghem, L. M. "Development of Class m Antiarrhythmic Agents". *J. Cardiovasc. Cardiol.,* 20 (Suppl. 2):S17-S22). Amiodarone has been shown to possess interesting Class III properties (Singh B. N., Vaughan Williams E. M. "A Third Class Of Anti-Arrhythmic Action: Effects On Atrial And Ventricular Intracellular Potentials And Other Pharmacological Actions On Cardiac Muscle, of MJ 1999 and AH 3747" *Br. J. Pharmacol.,* 39:675-689, 1970; Singh B. N., Vaughan Williams E. M, "The Effect Of Amiodarone, A New Anti-Anginal Drug, On Cardiac Muscle", *Br. J. Pharmacol.*, 39:657-667, 1970), although it is not a selective Class III agent because it effects multiple ion channels; additionally, its use is severely limited due to its side effect profile (Nademanee, K. "The Amiodarone Odyssey". *J. Am. Coll. Cardiol.*, 20:1063-1065, 1992; Fuster et al, *Circulation*, 104:2118-2150, 2001; Bril, A. *Curr. Opin. Pharmacol.* 2:154-159, 2002). Thus, currently available agents such as amiodarone and Class III drugs confer a significant risk of adverse effects including the development of potentially lethal ventricular proarrhythmia.

The ultrarapid delayed rectifier K$^+$ current, I$_{Kur}$, has been observed specifically in human atrium and not in ventricle. The molecular correlate of I$_{Kur}$ in the human atrium is the potassium channel designated Kv1.5. Kv1.5 mRNA (Bertaso, Sharpe, Hendry, and James, *Basic Res. Cardiol.*, 97:424-433, 2002) and protein (Mays, Foose, Philipson, and Tankan, *J. Clin. Invest.*, 96:282-292, 1995) have been detected in human atrial tissue. In intact human atrial myocytes, an ultra-rapidly activating delayed rectifier K$^+$ current (I$_{Kur}$), also known as the sustained outward current, I$_{sus}$ or I$_{so}$, has been identified and this current has properties and kinetics identical to those expressed by the human K$^+$ channel clone (hKv1.5, HK2) [Wang, Fermini and Nattel, *Circ. Res.*, 73:1061-1076, 1993; Fedida et al., *Circ. Res.* 73:210-216, 1993; Snyders, Tamkun and Bennett, *J. Gen. Physiol.*, 101: 513-543, 1993] and a similar clone from rat brain (Swanson et al., *Neuron*, 4:929-939, 1990). Furthermore, because of its rapidity of activation and limited slow inactivation, I$_{Kur}$ is believed to contribute significantly to repolarization in human atrium. Consequently, a specific blocker of I$_{Kur}$, that is a compound which blocks Kv1.5, would overcome the shortcoming of other compounds by prolonging refractoriness through retardation of the repolarization in the human atrium without causing the delays in ventricular repolarization that underlie arrhythmogenic after depolarizations and acquired long QT syndrome observed during treatment with current Class III drugs. Kv1.5 blockers exhibiting these properties have been described (Peukert et al, *J. Med. Chem.*, 46:486-498, 2003; Knobloch et al, *Naunyn-Schmedieberg's Arch. Pharmacol.* 366:482-287, 2002; Merck & Co., Inc. WO0224655, 2002).

The compounds described in this invention represent a novel structural class of Kv1.5 antagonist.

SUMMARY OF THE INVENTION

This invention relates to potassium channel inhibitors of general structural Formula I

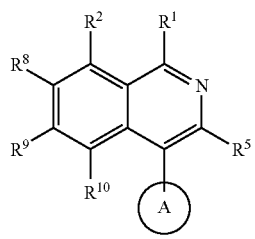

(I)

The compounds of this invention are useful in the treatment and prevention of cardiac arrhythmias, and the like. Also within the scope of this invention are pharmaceutical formulations comprising a compound of Formula I and a pharmaceutical carrier.

DETAILED DESCRIPTION OF THE DISCLOSURE

The present invention is a compound of formula I

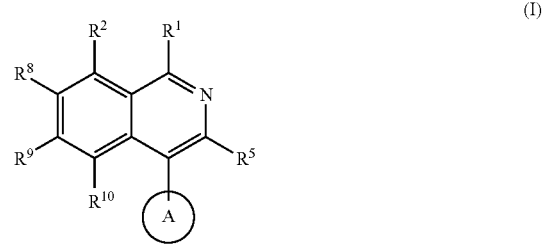

(I)

or a pharmaceutically acceptable salt, crystal form, or hydrate, wherein:

A is
a) an aryl ring, wherein any stable aryl ring atom is independently unsubstituted or substituted with
1) halogen,
2) NO$_2$,
3) CN,
4) CR$^{46}$=C(R$^{47}$R$^{48}$)$_2$,
5) C≡C R$^{46}$,
6) (CR$^{i}$R$^{j}$)$_r$OR$^{46}$,
7) (CR$^{i}$R$^{j}$)$_r$N(R$^{46}$R$^{47}$),
8) (CR$^{i}$R$^{j}$)$_r$C(O)R$^{46}$,
9) (CR$^{i}$R$^{j}$)$_r$C(O)OR$^{46}$,
10) (CR$^{i}$R$^{j}$)$_r$R$^{46}$,
11) (CR$^{i}$R$^{j}$)$_r$S(O)$_{0-2}$R$^{61}$,
12) (CR$^{i}$R$^{j}$)$_r$S(O)$_{0-2}$N(R$^{46}$R$^{47}$),
13) OS(O)$_{0-2}$R$^{61}$,
14) N(R$^{46}$)C(O)R$^{47}$,
15) N(R$^{46}$)S(O)$_{0-2}$R$^{61}$,
16) (CR$^{i}$R$^{j}$)$_r$N(R$^{46}$)R$^{61}$,
17) (CR$^{i}$R$^{j}$)$_r$N(R$^{46}$)R$^{61}$OR$^{47}$,
18) (CR$^{i}$R$^{j}$)$_r$N(R$^{46}$)(CR$^{k}$R$^{j}$)$_s$C(O)N(R$^{47}$R$^{48}$),
19) N(R$^{46}$)(CR$^{i}$R$^{j}$)$_r$R$^{61}$,
20) N(R$^{46}$)(CR$^{i}$R$^{j}$)$_r$N(R$^{47}$R$^{48}$),
21) (CR$^{i}$R$^{j}$)$_r$C(O)N(R$^{47}$R$^{48}$), or
22) oxo, b) a heteroaryl ring selected from the group consisting of a 5-membered unsaturated monocyclic ring with 1, 2, 3 or 4 heteroatom ring atoms selected from the group consisting or N, O or S,
a 6-membered unsaturated monocyclic ring with 1, 2, 3 or 4 heteroatom ring atoms selected from the group consisting N, O and S, and
a 9- or 10-membered unsaturated bicyclic ring with 1, 2, 3 or 4 heteroatom ring atoms selected from the group consisting or N, O or S,
wherein any stable S heteroaryl ring atom is unsubstituted or mono- or di-substituted with oxo, and any stable C or N heteroaryl ring atom is independently unsubstituted or substituted with
1) halogen,
2) NO$_2$,
3) CN,
4) CR$^{46}$=C(R$^{47}$R$^{48}$)$_2$,
5) C≡CR$^{46}$,
6) (CR$^{i}$R$^{j}$)$_r$OR$^{46}$,
7) (CR$^{i}$R$^{j}$)$_r$N(R$^{46}$R$^{47}$),
8) (CR$^{i}$R$^{j}$)$_r$C(O)R$^{46}$, 9) $(CR^iR^j)_rC(O)OR^{46}$,
10) $(CR^iR^j)_rR^{46}$,
11) $(CR^iR^j)_rS(O)_{0-2}R^{61}$,
12) $(CR^iR^j)_rS(O)_{0-2}N(R^{46}R^{47})$,
13) $OS(O)_{0-2}R^{61}$,
14) $N(R^{46})C(O)R^{47}$,
15) $N(R^{46})S(O)_xR^{61}$,
16) $(CR^iR^j)_rN(R^{46})R^{61}$,
17) $(CR^iR^j)_rN(R^{46})R^{61}OR^{47}$,
18) $(CR^iR^j)_rN(R^{46})(CR^kR^l)_sC(O)N(R^{47}R^{48})$,
19) $N(R^{46})(CR^iR^j)_rR^{61}$,
20) $N(R^{46})(CR^iR^j)_rN(R^{47}R^{48})$,
21) $(CR^iR^j)_rC(O)N(R^{47}R^{48})$, or
22) oxo, or c) a 4-, 5- or 6-membered heterocyclic ring containing 1 or 2 nitrogen atoms, unsubstituted, mono-substituted or di-substituted with $C_1$-$C_6$ alkyl;

Y is $CH_2$, $NR^{53}$, $NC(O)R^{53}$, $S(O)_{0-2}$ or O;
G is $H_2$ or O;
$R^a$, $R^b$, $R^c$, $R^d$, $R^e$, $R^f$, $R^g$, $R^h$, $R^i$, $R^j$, $R^k$, and $R^l$ are independently selected from the group consisting of:
1) hydrogen,
2) $C_1$-$C_6$ alkyl,
3) halogen,
4) aryl,
5) $R^{80}$,
6) $C_3$-$C_{10}$ cycloalkyl, and
7) $OR^4$, said alkyl, aryl, and cycloalkyl being unsubstituted, mono-substituted with $R^7$, disubstituted with $R^7$ and $R^{15}$, trisubstituted with $R^7$, $R^{15}$ and $R^{16}$, or tetrasubstituted with $R^7$, $R^{15}$, $R^{16}$ and $R^{17}$;

$R^1$ is independently selected from:
1) hydrogen,
2) halogen,
3) $NO_2$,
4) CN,
5) $CR^{40}=C(R^{41}R^{42})$,
6) $C\equiv CR^{40}$,
7) $(CR^aR^b)_nOR^{40}$,
8) $(CR^aR^b)_nN(R^{40}R^{41})$,
9) $(CR^aR^b)_nC(O)R^{40}$,
10) $(CR^aR^b)_nC(O)OR^{40}$,
11) $(CR^aR^b)_nR^{40}$,
12) $(CR^aR^b)_nS(O)_{0-2}R^6$,
13) $(CR^aR^b)_nS(O)_{0-2}N(R^{40}R^{41})$,
14) $OS(O)_{0-2}R^6$,
15) $N(R^{40})C(O)R^{41}$,
16) $N(R^{40})S(O)_{0-2}R^6$,
17) $(CR^aR^b)_nN(R^{40})R^6$,
18) $(CR^aR^b)_nN(R^{40})R^6OR^{41}$,
19) $(CR^aR^b)_nN(R^{40})(CR^cR^d)_tC(O)N(R^{41}R^{42})$,
20) $N(R^{40})(CR^aR^b)_nR^6$,
21) $N(R^{40})(CR^aR^b)_nN(R^{41}R^{42})$,

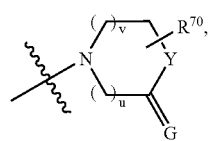
22)

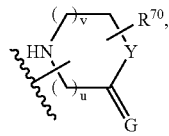
23)

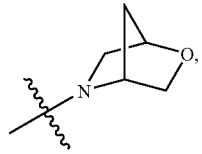
24)

25) $(CR^aR^b)_nC(O)N(R^{41}R^{42})$, and
26) a 4-, 5-, or 6-membered heterocyclic ring containing 1 nitrogen atom, unsubstituted, or mono-, di- or tri-substituted with —OH;

$R^2$, $R^8$, $R^9$ and $R^{10}$ are independently selected from:
1) hydrogen,
2) halogen,
3) $NO_2$,
4) CN,
5) $CR^{43}=C(R^{44}R^{45})$,
6) $C\equiv CR^{43}$,
7) $(CR^eR^f)_pOR^{43}$,
8) $(CR^eR^f)_pN(R^{43}R^{44})$,
9) $(CR^eR^f)_pC(O)R^{43}$,
10) $(CR^eR^f)_pC(O)OR^{43}$,
11) $(CR^eR^f)_pR^{43}$,
12) $(CR^eR^f)_pS(O)_{0-2}R^{60}$,
13) $(CR^eR^f)_pS(O)_{0-2}N(R^{43}R^{44})$,
14) $OS(O)_{0-2}R^{60}$,
15) $N(R^{43})C(O)R^{44}$,
16) $N(R^{43})S(O)_{0-2}R^{60}$,
17) $(CR^eR^f)_pN(R^{43})R^{60}$,
18) $(CR^eR^f)_pN(R^{43})R^{60}OR^{44}$,
19) $(CR^eR^f)_pN(R^{43})(CR^gR^h)_qC(O)N(R^{44}R^{45})$,
20) $N(R^{43})(CR^eR^f)_pR^{60}$,
21) $N(R^{43})(CR^eR^f)_pN(R^{44}R^{45})$, and
22) $(CR^eR^f)_pC(O)N(R^{43}R^{44})$, or $R^2$ and $R^8$ are independently as defined above, and $R^9$ and $R^{10}$, together with the atoms to which they are attached, form the ring

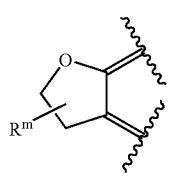

where $R^m$ is $C_{1-6}$alkyl;
$R^4$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, and $R^{53}$ are independently selected from:
1) hydrogen,
2) $C_1$-$C_6$ alkyl,
3) $C_3$-$C_{10}$ cycloalkyl,
4) aryl,
5) $R^{81}$,
6) $CF_3$,
7) $C_2$-$C_6$ alkenyl, and
8) $C_2$-$C_6$ alkynyl,

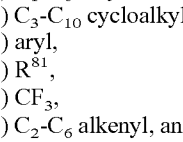

said alkyl, aryl, and cycloalkyl is unsubstituted, mono-substituted with $R^{18}$, di-substituted with $R^{18}$ and $R^{19}$, tri-substituted with $R^{18}$, $R^{19}$ and $R^{20}$, or tetra-substituted with $R^{18}$, $R^{19}$, $R^{20}$ and $R^{21}$;

$R^5$ is independently selected from:
1) hydrogen,
2) halogen,
3) CN,
4) $C(O)N(R^{49}R^{50})$,
5) $C(O)OR^{49}$,
6) $S(O)_{0-2}N(R^{49}R^{50})$,
7) $S(O)_{0-2}R^{62}$,
8) $C_1$-$C_6$ alkyl,
9) $C_3$-$C_{10}$ cycloalkyl,
10) $R^{82}$, said alkyl, aryl, and cycloalkyl is unsubstituted, mono-substituted with $R^{22}$, di-substituted with $R^{22}$ and $R^{23}$, tri-substituted with $R^{22}$, $R^{23}$ and $R^{24}$, or tetra-substituted with $R^{22}$, $R^{23}$, $R^{24}$ and $R^{25}$;

$R^6$, $R^{60}$ $R^{61}$, $R^{62}$ and $R^{63}$ are independently selected from:
1) $C_1$-$C_6$ alkyl,
2) aryl,
3) $R^{83}$, and
4) $C_3$-$C_{10}$ cycloalkyl;

said alkyl, aryl, and cycloalkyl is unsubstituted, mono-substituted with $R^{26}$, di-substituted with $R^{26}$ and $R^{27}$, tri-substituted with $R^{26}$, $R^{27}$ and $R^{28}$, or tetra-substituted with $R^{26}$, $R^{27}$, $R^{28}$ and $R^{29}$;

$R^7$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{70}$ are independently selected from:
1) $C_1$-$C_6$ alkyl,
2) halogen,
3) $OR^{51}$,
4) $CF_3$,
5) aryl,
6) $C_3$-$C_{10}$ cycloalkyl,
7) $R^{84}$,
8) $S(O)_{0-2}N(R^{51}R^{52})$,
9) $C(O)OR^{51}$,
10) $C(O)R^{51}$,
11) CN,
12) $C(O)N(R^{51}R^{52})$,
13) $N(R^{51})C(O)R^{52}$,
14) $S(O)_{0-2}R^{63}$,
15) $NO_2$, and
16) $N(R^{51}R^{52})$;

$R^{80}$, $R^{81}$, $R^{82}$, $R^{83}$ and $R^{84}$ are independently selected from a group of unsubstituted or substituted heterocyclic rings consisting of a 4-6 membered unsaturated or saturated monocyclic ring with 1, 2, 3 or 4 heteroatom ring atoms selected from the group consisting N, O and S, and a 9- or 10-membered unsaturated or saturated bicyclic ring with 1, 2, 3 or 4 heteroatom ring atoms selected from the group consisting or N, O or S;

n, p, q, r, s and t are independently 0, 1, 2, 3, 4, 5 or 6;
u is 0, 1 or 2; and
v is 0, 1 or 2.

In a class of compounds of the invention, or pharmaceutically acceptable salts thereof, A is a) an aryl ring selected from phenyl, unsubstituted or substituted as defined above, b) a heteroaryl ring, unsubstituted or substituted as defied above, selected from the group consisting of pyridine, pyrimidine, pyrazine, pyridazine, indole, pyrrolopyridine, benzimidazole, benzoxazole, benzothiazole, and benzoxadiazole, or c) a 4-, 5-, or 6-membered heterocyclic ring as defined above;

$R^2$, $R^8$, $R^9$ and $R^{10}$ are independently selected from the group consisting of:
1) hydrogen,
2) halogen,
3) $OR^{43}$, and
4) $(CR^eR^f)_pR^{43}$, or $R^2$ and $R^8$ are independently as defined above, and $R^9$ and $R^{10}$, together with the atoms to which they are attached, form the ring

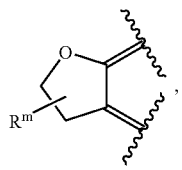

$R^m$ is $C_{1-6}$alkyl;

$R^1$ is independently selected from:
1) hydrogen,
2) halogen,
3) CN,
4) $OR^{40}$,
5) $N(R^{40}R^{41})$,
6) $C(O)OR^{40}$,
7) $R^{81}$,
8) $S(O)_{0-2}R^6$,
9) $N(R^{40})(CR^aR^b)_nR^6$, wherein $R^6$=$R^{83}$,
10) $N(R^{40})(CR^aR^b)_nN(R^{41}R^{42})$,

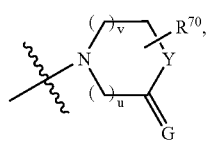

11)

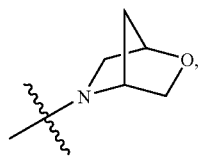

12)

13) $C(O)N(R^{41}R^{42})$, and
14) a 4-, 5-, or 6-membered heterocyclic ring containing 1 nitrogen atom, unsubstituted, or mono-, di- or tri-substituted with —OH.

In a subclass of the class of compounds, or pharmaceutically acceptable salts thereof, $R^2$, $R^8$, and $R^{10}$ are independently selected from hydrogen and halogen, and $R^9$ is $OCH_3$ or $OCHF_2$.

In a group of the subclass of compounds, or pharmaceutically acceptable salts thereof, $R^1$ is selected from the group consisting of hydrogen, —$SCH_3$, —$SO_2CH_3$, —$NH(CH_2)_3OH$, —$NH(CH_2)_2OH$, —$NH(CH_2)_2OCH_3$, —$NH(CH_2)_3OCH_3$, —$NH(CH_2)_2NH_2$, —$NH_2$, —$SO_2CH_2CH_3$, —CN, Cl, —$OCH_3$, —$OCH_2CHCH_2$, —$OCH_2CH(OH)CH_2OH$, —$NHCH_2CHCH_2$, —$CH_3$, —$CH_2CH_2OH$, —$O(CH_2)_2CHCH_2$, —$O(CH_2)_2CH(OH)(CH_2OH)$, —$NHCH(CH_2OH)_2$, —$NHCH_2CH(OH)CH_2OH$, —$NH(CH_2)_2CH(OH)CH_2OH$,

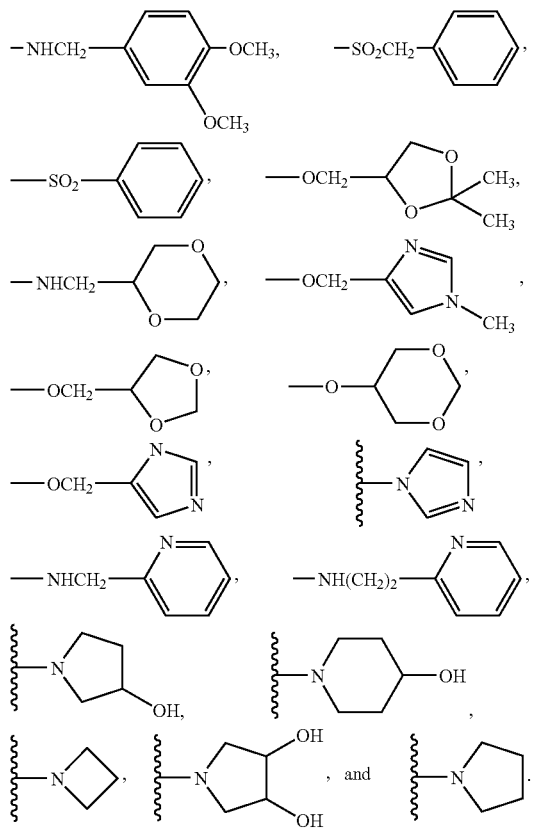

In a subgroup of the group of compounds, or pharmaceutically acceptable salts thereof, A is selected from the group consisting of
1) phenyl, wherein any stable ring atom is unsubstituted or substituted with halogen,
2) pyridinyl, wherein any stable C ring atom is unsubstituted or substituted with halogen,
3) indolyl, wherein any stable C or N ring atom is unsubstituted or substituted with halogen, and
4) a heterocyclic ring selected from the group consisting of pyrrolidine, piperidine, piperazine, and azetidine, unsubstituted, mono-substituted or di-substituted with $C_1$-$C_6$ alkyl.

In a family of the subgroup of compounds, or pharmaceutically acceptable salts thereof, $R^5$ is selected from the group consisting of CN and $C_1$-$C_6$ alkyl, wherein said alkyl is unsubstituted, mono-substituted with $R^{22}$, di-substituted with $R^{22}$ and $R^{23}$, tri-substituted with $R^{22}$, $R^{23}$ and $R^{24}$, or tetra-substituted with $R^{22}$, $R^{23}$, $R^{24}$ and $R^{25}$.

A preferred embodiment is a compound selected from the group consisting of [(6-methoxy-4-phenylisoquinolin-3-yl)methyl]dimethylamine,
1-(1-chloro-6-methoxy-4-phenylisoquinolin-3-yl)-N,N-dimethylmethanamine,
{[6-methoxy-1-(methylthio)-4-phenylisoquinolin-3-yl]methyl}dimethylamine,
[6-methoxy-1-(methylsulfonyl)-4-phenylisoquinolin-3-yl]methyl(dimethyl)amine oxide,
1-[6-methoxy-1-(methylsulfonyl)-4-phenylisoquinolin-3-yl]-N,N-dimethylmethanamine,
3-[(dimethylamino)methyl]-6-methoxy-4-phenylisoquinoline-1-carbonitrile,
2,3-Dimethyl-6-methoxy-4-phenylisoquinolinium hydroxide,
6-methoxy-1-(2-methoxyethoxy)-3-methyl-4-phenylisoquinoline,
{3-[(6-methoxy-3-methyl-4-phenylisoquinolin-1-yl)oxy]propyl}amine,
2-[(6-methoxy-3-methyl-4-phenylisoquinolin-1-yl)amino]ethanol,
6-methoxy-3-methyl-1-(methylsulfonyl)-4-phenylisoquinoline,
6-methoxy-N-(2-methoxyethyl)-3-methyl-4-phenylisoquinolin-1-amine,
N-(6-methoxy-3-methyl-4-phenylisoquinolin-1-yl)ethane-1,2-diamine,
6-methoxy-3-methyl-4-phenylisoquinoline,
N-(3,4-dimethoxybenzyl)-6-methoxy-3-methyl-4-phenylisoquinolin-1-amine,
6-methoxy-3-methyl-4-phenylisoquinolin-1-amine,
1-(ethylsulfonyl)-6-methoxy-3-methyl-4-phenylisoquinoline,
1-(benzylsulfonyl)-6-methoxy-3-methyl-4-phenylisoquinoline,
6-methoxy-3-methyl-4-phenyl-1-(phenylsulfonyl)isoquinoline,
6-methoxy-3-methyl-4-phenylisoquinoline-1-carbonitrile,
3-tert-butyl-6-methoxy-1-(2-methoxyethoxy)-4-phenylisoquinoline,
1-chloro-6-methoxy-4-phenylisoquinoline-3-carbonitrile,
6-methoxy-4-phenylisoquinoline-1,3-dicarbonitrile,
1-(allyloxy)-6-methoxy-4-phenylisoquinoline-3-carbonitrile,
1-(2,3-dihydroxypropoxy)-6-methoxy-4-phenylisoquinoline-3-carbonitrile,
(allylamino)-6-methoxy-4-phenylisoquinoline-3-carbonitrile,
(+/−)-1-[(2,3-dihydroxypropyl)amino]-6-methoxy-4-phenylisoquinoline-3-carbonitrile,
1-{[(2S)-2,3-dihydroxypropyl]amino}-6-methoxy-4-phenylisoquinoline-3-carbonitrile,
1-{[(2R)-2,3-dihydroxypropyl]amino}-6-methoxy-4-phenylisoquinoline-3-carbonitrile,
(+/−)-1-[(2,2-dimethyl-1,3-dioxolan-4-yl)methoxy]-6-methoxy-4-phenylisoquinoline-3-carbonitrile,
1-{[(4S)-2,2-dimethyl-1,3-dioxolan-4-yl]methoxy}-6-methoxy-4-phenylisoquinoline-3-carbonitrile,
1-{[(4R)-2,2-dimethyl-1,3-dioxolan-4-yl]methoxy}-6-methoxy-4-phenylisoquinoline-3-carbonitrile,
1-{[(2R)-2,3-dihydroxypropyl]oxy}-6-methoxy-4-phenylisoquinoline-3-carbonitrile,
1-{[(2S)-2,3-dihydroxypropyl]oxy}-6-methoxy-4-phenylisoquinoline-3-carbonitrile,
(+/−)-1-{[2,3-dihydroxypropyl]oxy}-6-methoxy-4-phenylisoquinoline-3-carbonitrile,
1-[(3R)-3-hydroxypyrrolidin-1-yl]-6-methoxy-4-phenylisoquinoline-3-carbonitrile,
1-[(3S)-3-hydroxypyrrolidin-1-yl]-6-methoxy-4-phenylisoquinoline-3-carbonitrile,
(+/−)-1-[3-hydroxypyrrolidin-1-yl]-6-methoxy-4-phenylisoquinoline-3-carbonitrile,
1-[cis-3,4-diydroxypyrrolidin-1-yl]-6-methoxy-4-phenylisoquinoline-3-carbonitrile,
6-methoxy-4phenyl-1-pyrrolidin-1-ylisoquinoline-3-carbonitrile,
6-methoxy-1-(methylsulfonyl)-4-phenylisoquinoline-3-carbonitrile,
6-methoxy-4-phenylisoquinoline-3-carbonitrile,
1,6-dimethoxy-4-phenylisoquinoline-3-carbonitrile, 1-chloro-4-(3-fluorophenyl)-6-methoxyisoquinoline-3-carbonitrile,
4-(3-fluorophenyl)-6-methoxyisoquinoline-3-carbonitrile,
4-(3-fluorophenyl)-6-methoxy-1-methylisoquinoline-3-carbonitrile,
4-(3-fluorophenyl)-1-[(2-hydroxyethyl)amino]-6-methoxyisoquinoline-3-carbonitrile,
1-amino-4-(3-fluorophenyl)-6-methoxyisoquinoline-3-carbonitrile,
4-(3-fluorophenyl)-1-[(3-hydroxypropyl)amino]-6-methoxyisoquinoline-3-carbonitrile,
1-(but-3-enyloxy)-4-3-fluorophenyl)-6-methoxyisoquinoline-3-carbonitrile,
(+/−)-1-2,3-dihydroxypropoxy)-4-3-fluorophenyl)-6-methoxyisoquinoline-3-carbonitrile,
1-[(2R)-2,3-dihydroxypropoxy]-4-(3-fluorophenyl)-6-methoxyisoquinoline-3-carbonitrile,
1-[(2S)-2,3-dihydroxypropoxy]-4-(3-fluorophenyl)-6-methoxyisoquinoline-3-carbonitrile,
(+/−)-1-(3,4-dihydroxybutoxy)-4-(3-fluorophenyl)-6-methoxyisoquinoline-3-carbonitrile,
(+/−)-1-[(3R)-3,4-dihydroxybutoxy]-4-(3-fluorophenyl)-6-methoxyisoquinoline-3-carbonitrile,
1-[(3S)-3,4-dihydroxybutoxy]-4-(3-fluorophenyl)-6-methoxyisoquinoline-3-carbonitrile,
(+/−)-1-[(1,4-dioxan-2-ylmethyl)amino]-4-(3-fluorophenyl)-6-methoxyisoquinoline-3-carbonitrile,
1-[(1,4-dioxan-(2R)-2-ylmethyl)amino]-4-(3-fluorophenyl)-6-methoxyisoquinoline-3-carbonitrile,
1-[(1,4-dioxan-(2S)-2-ylmethyl)amino]-4-(3-fluorophenyl)-6-methoxyisoquinoline-3-carbonitrile,
4-(3-fluorophenyl)-6-methoxy-1-[(1-methyl-1H-imidazol-4-yl)methoxy]isoquinoline-3-carbonitrile,
(+/−)-1-(1,3-dioxolan-4-ylmethoxy)-4-(3-fluorophenyl)-6-methoxyisoquinoline-3-carbonitrile,
1-1,3-dioxolan-(4R)-4-ylmethoxy)-4-(3-fluorophenyl)-6-methoxyisoquinoline-3-carbonitrile,
1-(1,3-Dioxolan-(4S)-4-ylmethoxy)-4-(3-fluorophenyl)-6-methoxyisoquinoline-3-carbonitrile,
1-(1,3-dioxan-5-yloxy)-4-(3-fluorophenyl)-6-methoxyisoquinoline-3-carbonitrile,
4-(3-fluorophenyl)-1-{[2-hydroxy-1-(hydroxymethyl)ethyl]amino}-6-methoxyisoquinoline-3-carbonitrile,
4-3-fluorophenyl)-1-(1H-imidazol-5-ylmethoxy)-6-methoxyisoquinoline-3-carbonitrile,
1-{[(2R)-2,3-dihydroxypropyl]amino}-4-(3-fluorophenyl)-6-methoxyisoquinoline-3-carbonitrile,
1-{[(2S)-2,3-dihydroxypropyl]amino}-4-(3-fluorophenyl)-6-methoxyisoquinoline-3-carbonitrile,
(+/−)-1-{[2,3-dihydroxypropyl]amino}-4-(3-fluorophenyl)-6-methoxyisoquinoline-3-carbonitrile,
1-(1H-imidazol-1-yl)-6-methoxy-4-phenylisoquinoline-3-carbonitrile,
6-methoxy-4-phenyl-1-[(pyridin-2-ylmethyl)amino]isoquinoline-3-carbonitrile,
6-methoxy-4-phenyl-1-[(2-pyridin-2-ylethyl)amino]isoquinoline-3-carbonitrile,
(+/−)-1-[(3,4-dihydroxybutyl)amino]-4-(3-fluorophenyl)-6-methoxyisoquinoline-3-carbonitrile,
1-[(3R)-(3,4-dihydroxybutyl)amino]-4-(3-fluorophenyl)-6-methoxyisoquinoline-3-carbonitrile,
1-[(3S)-(3,4-dihydroxybutyl)amino]-4-(3-fluorophenyl)-6-methoxyisoquinoline-3-carbonitrile,
1-chloro-4-(2-fluorophenyl)-6-methoxyisoquinoline-3-carbonitrile,
4-(2-fluorophenyl)-6-methoxyisoquinoline-3-carbonitrile,
(+/−)-1-[(2,3-dihydroxypropyl)amino]-4-(2-fluorophenyl)-6-methoxyisoquinoline-3-carbonitrile,
1-[(2S)-(2,3-dihydroxypropyl)amino]-4-(2-fluorophenyl)-6-methoxyisoquinoline-3-carbonitrile,
1-[(2R)-(2,3-dihydroxypropyl)amino]-4-(2-fluorophenyl)-6-methoxyisoquinoline-3-carbonitrile,
(+/−)-6-(difluoromethoxy)-1-{[2,3-dihydroxypropyl]amino}-4-(3-fluorophenyl)isoquinoline-3-carbonitrile,
6-(difluoromethoxy)-1-{[(2S)-2,3-dihydroxypropyl]amino}-4-(3-fluorophenyl)isoquinoline-3-carbonitrile,
6-(difluoromethoxy)-1-{[(2R)-2,3-dihydroxypropyl]amino}-4-(3-fluorophenyl)isoquinoline-3-carbonitrile,
(+/−)-6-(difluoromethoxy)-1-{[2,3-dihydroxypropyl]oxy}-4-(3-fluorophenyl)isoquinoline-3-carbonitrile,
6-(difluoromethoxy)-1-{[(2S)-2,3-dihydroxypropyl]oxy}-4-(3-fluorophenyl)isoquinoline-3-carbonitrile,
6-(difluoromethoxy)-1-{[(2R)-2,3-dihydroxypropyl]oxy}-4-(3-fluorophenyl)isoquinoline-3-carbonitrile,
1-(4-hydroxypiperidin-1-yl)-6-methoxy-4-phenylisoquinoline-3-carbonitrile,
1-azetidin-1-yl-6-methoxy-4-phenylisoquinoline-3-carbonitrile,
(+/−)-1-[trans-3,4-dihydroxypyrrolidin-1-yl]-6-methoxy-4-phenylisoquinoline-3-carbonitrile,
1-[(3R,4R)-3,4-dihydroxypyrrolidin-1-yl]-6-methoxy-4-phenylisoquinoline-3-carbonitrile,
1-[(3S,4S)-3,4-dihydroxypyrrolidin-1-yl]-6-methoxy-4-phenylisoquinoline-3-carbonitrile, and
6-methoxy-N-(3-methoxypropyl)-3-methyl-4-phenylisoquinolin-1-amine or a pharmaceutically acceptable salt thereof.

The above-listed compounds are active in one or more of the assays for Kv1.5 described below.

Another embodiment of the invention is a method of treating or preventing a condition in a mammal, the treatment or prevention of which is effected or facilitated by Kv1.5 inhibition, which comprises administering an amount of a compound of Formula I that is effective at inhibiting Kv1.5.

A preferred embodiment is a method of treating or preventing cardiac arrhythmias, e.g. atrial fibrillation, atrial flutter, atrial arrhythmia, and supraventricular tachycardia, in a mammal, which comprises administering a therapeutically effective amount of a compound of Formula I.

Another preferred embodiment is a method of preventing thromboembolic events, such as stroke.

Another preferred embodiment is a method of preventing congestive heart failure.

Another preferred embodiment is a method of treating or preventing immunodepression or a disorder involving immunodepression, such as AIDS, cancer, senile dementia, trauma (including wound healing, surgery and shock) chronic bacterial infection, certain central nervous system disorders, and conditions including resistance by transplantation of organs or tissue, graft-versus-host diseases brought about by medulla ossium transplantation. Within this embodiment is a method for treating or preventing immunodepression by administering a compound of the invention with an immunosuppressant compound.

Another preferred embodiment is a method of treating or preventing gliomas including those of lower and higher malignancy, preferably those of higher malignancy.

Another preferred embodiment is a method for inducing in a patient having atrial fibrillation, a condition of normal sinus rhythm, in which the induced rhythm corresponds to the rhythm that would be considered normal for an individual sharing with the patient similar size and age characteristics, which comprises treating the patient with a compound of the invention.

Another preferred embodiment is a method for treating tachycardia, (i.e., rapid heart rate e.g. 100 beats per minute) in a patient which comprises treating the patient with an antitachycardia device (e.g. a defibrillator or a pacemaker) in combination with a compound of Claim 1.

The present invention also encompasses a pharmaceutical formulation comprising a pharmaceutically acceptable carrier and the compound of Formula I or a pharmaceutically acceptable crystal form or hydrate thereof. A preferred embodiment is a pharmaceutical composition of the compound of Formula I, comprising, in addition, a second agent.

The compounds of the present invention may have asymmetric centers or asymmetric axes, and this invention includes all of the optical isomers and mixtures thereof. Unless specifically mentioned otherwise, reference to one isomer applies to both isomers.

In addition compounds with carbon-carbon double bonds may occur in Z- and E-forms with all isomeric forms of the compounds being included in the present invention.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkoxy" represents a linear or branched alkyl group of indicated number of carbon atoms attached through an oxygen bridge.

The term "alkenyl" includes both branched and straight chain unsaturated hydrocarbon groups containing at least two carbon atoms joined by a double bond. The alkene ethylene is represented, for example, by "$CH_2CH_2$" or alternatively, by "$H_2C=CH_2$". "$C_{2-5}$ alkenyl" (or "$C_2$-$C_5$ alkenyl") for example, means linear or branched chain alkenyl groups having from 2 to 5 carbon atoms and includes all pentenyl isomers as well as 1-butenyl, 2-butenyl, 3-butenyl, 1-propenyl, 2-propenyl, and ethenyl (or ethylenyl). Similar terms such as "$C_{2-3}$ alkenyl" have an analogous meaning.

The term "alkynyl" includes both branched and straight chain unsaturated hydrocarbon groups containing at least two carbon atoms joined by a triple bond. The alkyne acetylene is represented, for example, by "CHCH" or alternatively, by "HC≡CH". "$C_{2-5}$ alkynyl" (or "$C_2$-$C_5$ alkynyl") for example, means linear or branched chain alkynyl groups having from 2 to 5 carbon atoms and includes all of the pentynyl isomers as well as 1-butynyl, 2-butynyl, 3-butynyl, 1-propynyl, 2-propynyl, and ethynyl (or acetylenyl). Similar terms such as "$C_{2-3}$ alkynyl" have an analogous meaning.

Unless otherwise noted, alkyl, alkenyl and alkynyl groups are unsubstituted or substituted with 1 to 3 substituents on each carbon atom, with halo, $C_1$-$C_{20}$ alkyl, $CF_3$, $NH_2$, $N(C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl)S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "$C_0$" as employed in expressions such as "$C_{0-6}$ alkyl" means a direct covalent bond. Similarly, when an integer defining the presence of a certain number of atoms in a group is equal to zero, it means that the atoms adjacent thereto are connected directly by a bond. For example, in the structure

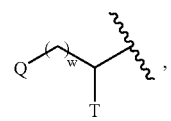

wherein w is an integer equal to zero, 1 or 2, the structure is

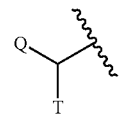

when w is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "$C_{1-6}$ haloalkyl" (which may alternatively be referred to as "$C_1$-$C_6$ haloalkyl" or "halogenated $C_1$-$C_6$ alkyl") means a $C_1$ to $C_6$ linear or branched alkyl group as defined above with one or more halogen substituents. The term "$C_{1-4}$ haloalkyl" has an analogous meaning. The term "$C_{1-6}$ fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

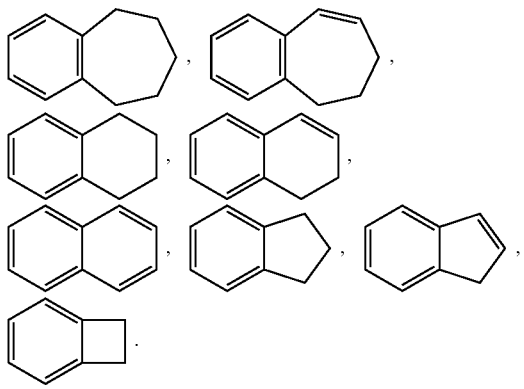

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, and biphenylenyl.

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. The heterocyclic ring may be attached at any heteroatom or carbon atom, provided that attachment results in the creation of a stable structure. When the heterocyclic ring has substituents, it is understood that the substituents may be attached to any atom in the ring, whether a heteroatom or a carbon atom, provided that a stable chemical structure results.

As used herein, the terms "substituted $C_3$-$C_{10}$ cycloalkyl", "substituted aryl" and "substituted heterocycle" are intended to include the cyclic group containing from 1 to 3 substituents in addition to the point of attachment to the rest of the compound. Preferably, the substituents are selected from the group which includes, but is not limited to, halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) $S(O)_{0-2}$—, ($C_0$-$C_6$ alkyl)$S(O)_{0-2}$($C_0$-$C_6$ alkyl)-, ($C_0$-C6 alkyl)C(O)NH—, $H_2N$—C(NH)—, —O($C_1$-$C_6$ alkyl)$CF_3$, ($C_0$-$C_6$ alkyl)C(O)—, ($C_0$-$C_6$ alkyl) OC(O)—, ($C_0$-$C_6$alkyl)O($C_1$-$C_6$ alkyl)-, ($C_0$-$C_6$ alkyl)C$(O)_{1-2}$($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e., (i.e., 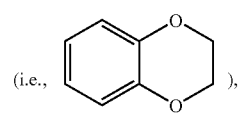 ), imidazo(2,1-b)(1,3)thiazole, (i.e., (i.e., 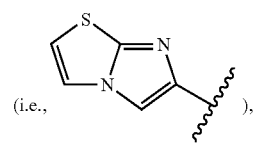 ), and benzo-1,3-dioxolyl (i.e., (i.e., 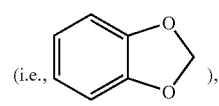 ), In certain contexts herein,

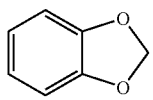

is alternatively referred to as phenyl having as a substituent methylenedioxy attached to two adjacent carbon atoms.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

In compounds of the invention having pyridyl N-oxide moieties, the pyridyl-N-oxide portion is structurally depicted using conventional representations such as which have equivalent meanings.

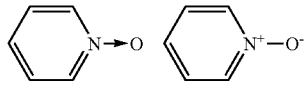

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

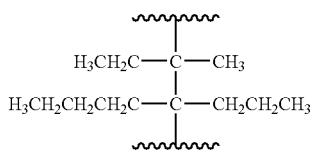

Pharmaceutically acceptable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hydro-scopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

Methods for preparing the compounds of this invention are illustrated in the following schemes. Other synthetic protocols will be readily apparent to those skilled in the art.

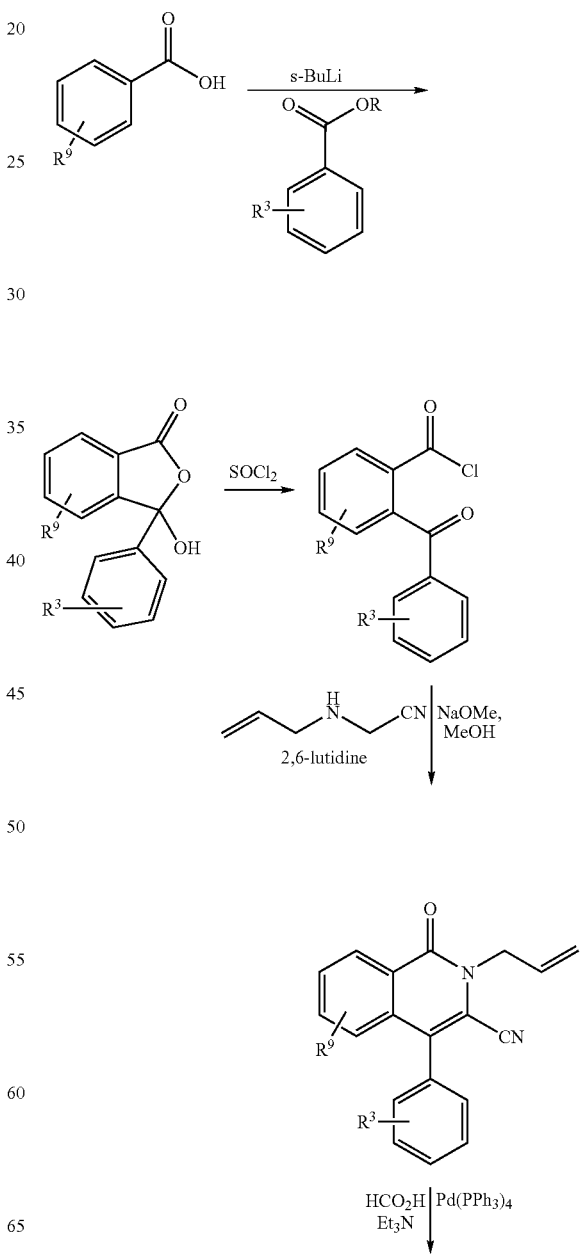

Scheme 1

-continued
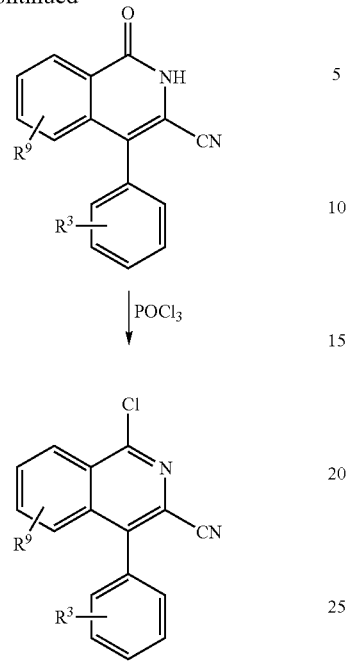
wherein $R^9$ is as defined above, and $R^3$ is a substituent on ring A as defined above where A is an aryl ring.
Scheme 2
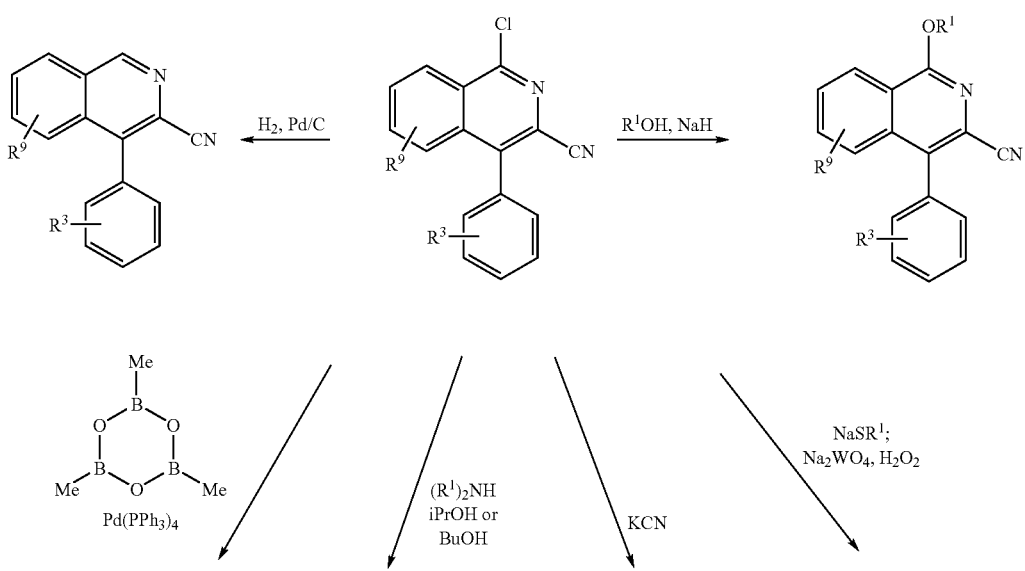

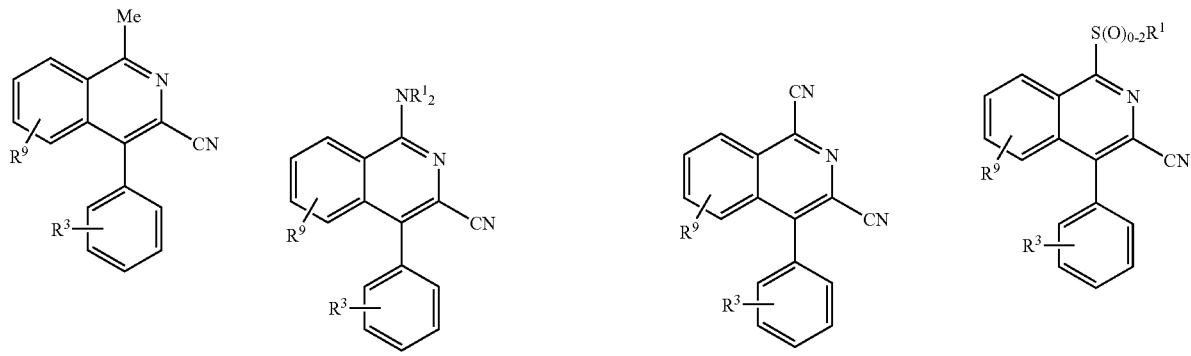
wherein $R^1$ in each instance is independently defined as above, $R^9$ is as defined above, and $R^3$ is a substituent on ring A as defined above where A is an aryl ring.
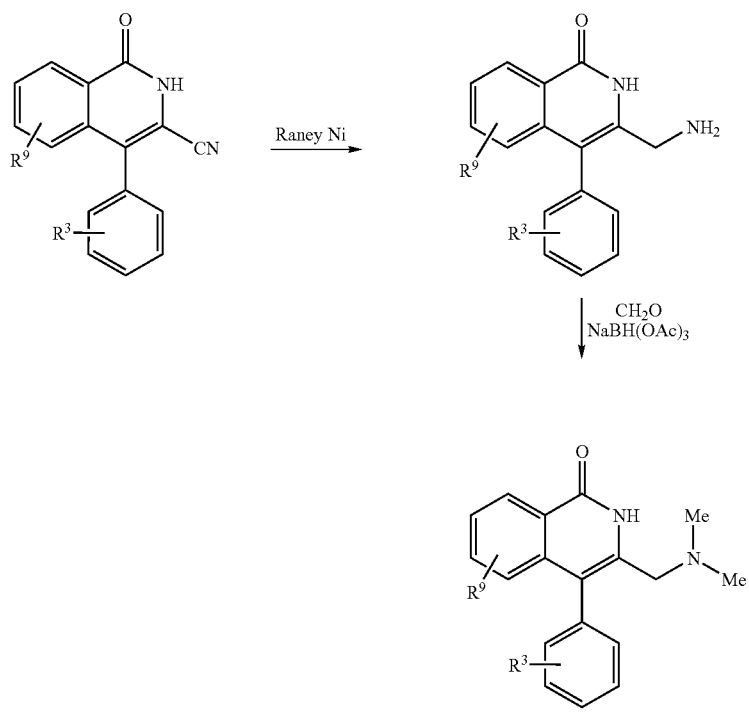

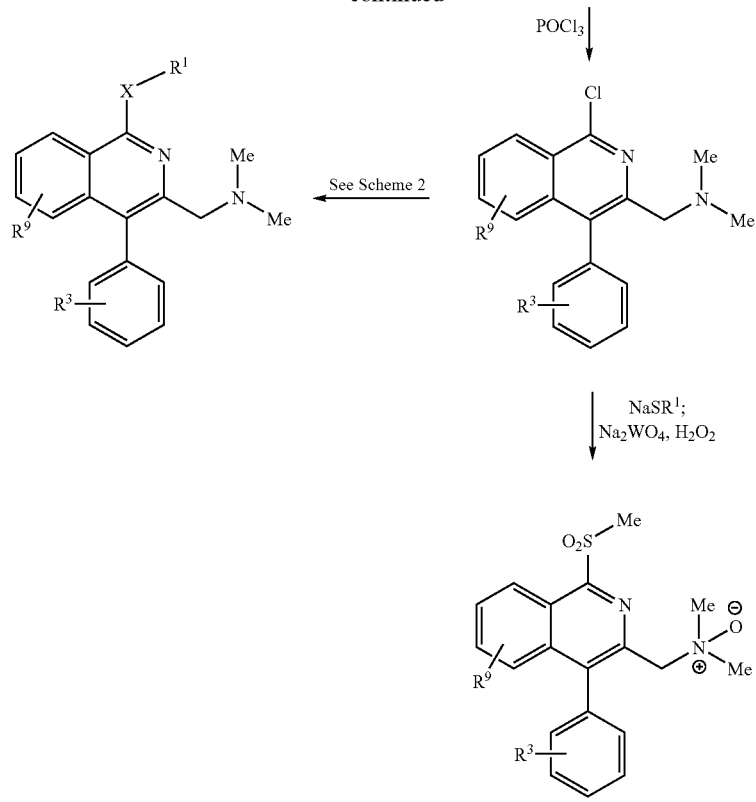

wherein $R^1$ is defined as above, $R^9$ is as defined above, and $R^3$ is a substituent on ring A as defined above where A is an aryl ring.

The following examples illustrate the preparation of the compounds of Formula I and as such are not to be considered as limiting the invention set forth in the claims appended hereto.

EXAMPLE 1

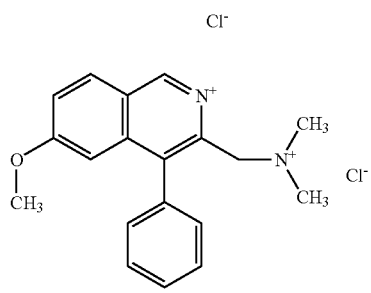

3-[(dimethylammonio)methyl]-6-methoxy-4-phenyl-isoquinolinium dichloride

Step A

To a solution of 1-chloro-6-methoxy-4-phenylisoquinoline-3-carbonitrile (150 mg) in 20 mL absolute EtOH and 5 ml aqueous NH$_4$OH was added 150 mg of Raney Ni. The reaction was shaken under 12 (40 psi) for 18 h. Filtration and concentration of the reaction gave 85 mg of 1-(6-methoxy-4-phenylisoquinolin-3-yl)methanamine.

Step B

To a solution of 1-(6-methoxy-4-phenylisoquinolin-3-yl) methanamine (80 mg) in 4 mL methanol were added formaldehyde (0.130 ml of a 37% aqueous solution) and sodium cyanoborohydride (1.30 ml of a 1 M THF solution). The reaction was stirred at room temp for 1 h, then quenched with aqueous KHSO4. The pH was adjusted to 7, and the mixture was extracted with EtOAc. Flash chromatography of the concentrated organic solution (5% MeOH (10% NH$_4$OH) in CH$_2$Cl$_2$) provided an oil, which was exposed to HCl to provide the titled compound.

M+H calcd: 293; found: 293 (ES)

EXAMPLE 2

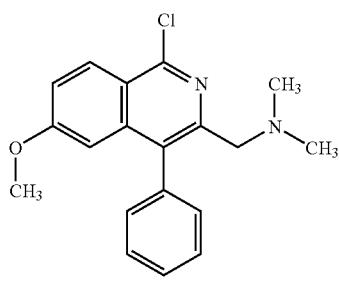

1-(1-chloro-6-methoxy-4-phenylisoquinolin-3-yl)-N,N-dimethylmethanamine

Step A

To a solution of 6-methoxy-1-oxo-4-phenyl-1,2-dihydroisoquinoline-3-carbonitrile (200 mg) in 40 mL ethanol were added Raney Ni and 4 mL of 2 M ammonia in methanol. The reaction was shaken under 50 psi $H_2$ pressure overnight. The reaction was filtered and concentrated to give 178 mg of 3-(aminomethyl)-6-methoxy-4-phenylisoquinolin-1(2H)-one.

Step B

To a solution of 3-(aminomethyl)-6-methoxy-4-phenylisoquinolin-1(2H)-one (100 mg) in 2 mL $CH_2Cl_2$ were added formaldehyde (0.115 mL of a 37% aqueous solution) and sodium triacetoxyborohydride (300 mg). The reaction was stirred overnight at room temperature, then partitioned between EtOAc and aqueous $KHSO_4$. Concentration of the organic solution and flash chromatography (5% MeOH (10% $NH_4OH$) in $CH_2Cl_2$) provided 58 mg of 3-[(dimethylamino)methyl]-6-methoxy-4-phenylisoquinolin-1(2H)-one.

Step C

3-[(dimethylamino)methyl]-6-methoxy-4-phenylisoquinolin-1(2H)-one (50 mg) was combined with 0.600 mL of POCl3, and the reaction was stirred at 90 C for 1 h. After cooling, the reaction was partitioned between saturated aqueous sodium bicarbonate and EtOAc. The organic solution was dried over $Na_2SO_4$ and concentrated. Flash chromatography (3% MeOH in $CH_2Cl_2$) gave the titled compound.

M+H calcd: 327; found: 327 (FAB)

EXAMPLE 3

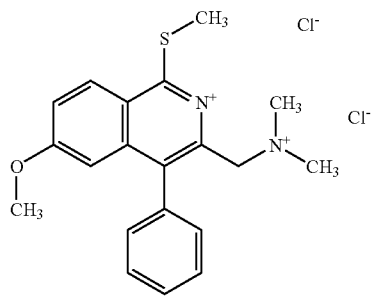

3-[(dimethylammonio)methyl]-6-methoxy-1-(methylthio)-4-phenylisoquinolinium dichloride To a solution of 1-(1-chloro-6-methoxy-4-phenylisoquinolin-3-yl)-N,N-dimethylmethanamine (158 mg) in DMF was added NaSMe (41 mg), and the reaction was stirred at room temp for 1 h. The mixture was partitioned between saturated aqueous sodium bicarbonate and EtOAc. The organic solution was dried over Na2SO4 and concentrated. Flash chromatography (3-10% MeOH in $CH_2Cl_2$) gave a solid which was dissolved in EtOAc and treated with excess HCl. The resulting solid was isolated by filtration to give the titled compound.

M+H calcd: 339; found: 339 (FAB)

EXAMPLE 4

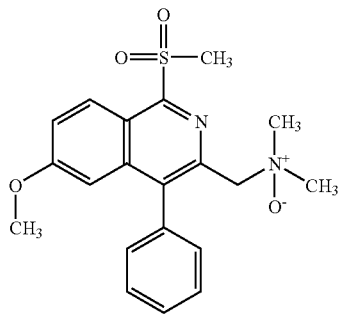

[6-methoxy-1-(methylsulfonyl)-4-phenylisoquinolin-3-yl]methyl(dimethyl)amine oxide To the free base of 3-[(dimethylammonio)methyl]-6-methoxy-1-(methylthio)-4-phenylisoquinolinium dichloride (85 mg) was added 5 mL of EtOAc and 1 mL of methanol. Hydorgen peroxide (30% aqueous, 0.120 mL) and sodium tungstate hydrate (17 mg) were added, and the reaction was heated to reflux for 3 h. After cooling, the reaction was partitioned between saturated aqueous sodium bicarbonate and EtOAc. The organic solution was dried over $Na_2SO_4$ and concentrated. Flash chromatography (5-10% MeOH (10% $NH_4OH$) in $CH_2Cl_2$) gave the titled compound.

M+H calcd: 387; found: 387 (FAB),

EXAMPLE 5

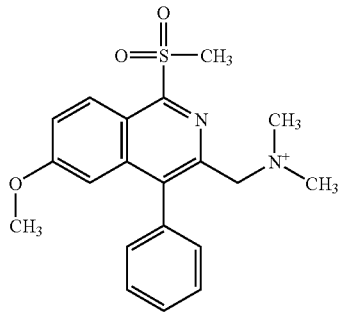

1-[6-methoxy-1-(methylsulfonyl)-4-phenylisoquinolin-3-yl]-N,N-dimethylmethanamine A mixture of 1-(1-chloro-6-methoxy-4-phenylisoquinolin-3-yl)-N,N-dimethylmethanamine (75 mg), 1 mL DMF, and $MeSO_2Na$ (41 mg) was stirred at 80 C for 48 h, then at 100 C for 96 h. The solution was cooled and purified directly by reverse-phase HPLC to give the titled compound.

M+H calcd: 371; found: 371 (FAB)

EXAMPLE 6

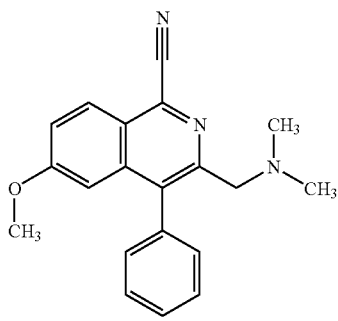

3-[(dimethylamino)methyl]-6-methoxy-4-phenyliso-
quinoline-1-carbonitrile

A mixture of 1-(1-chloro-6-methoxy-4-phenylisoquino-lin-3-yl)-N,N-dimethylmethanamine (31 mg), 1 mL DMSO, and 16 mg CuCN was stirred at 140 C for 3 h. The solution was cooled and purified directly by reverse-phase HPLC to give the titled compound.

M+H calcd: 318; found: 318 (FAB)

EXAMPLE 7

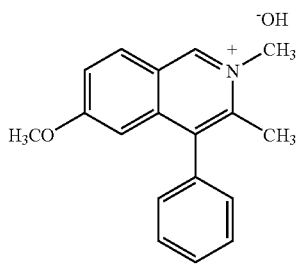

2,3-Dimethyl-6-methoxy-4-phenylisoquinolinium
hydroxide

To a stirred solution of 2,3-dimethyl-6-methoxy4-phenyl-2H-isoquinolin-1-one (prepared using the synthetic procedure previously described in WO 2002024655, 250 mg, 0.896mmol) in tetrahydrofuran (10 mL) at room temperature under argon was added by dropwise addition a solution of lithium aluminum hydride (1.0 M, 0.896 mL, 0.896 mmol). The contents of the reaction flask were heated to reflux for 0.5 h, cooled to room temperature and carefully poured onto ice. Saturated sodium bicarbonate was added and the resulting mixture extracted with ethyl acetate (3×). The combined organic extracts were washed with brine and then dried with sodium sulfate (anh.). Filtration followed by removal of the solvent in vacuo gave a brown oil which was subjected to flash column chromatography (hexane:ethyl acetate 90:10). Evaporation of fractions containing product gave a tan oil which was triturated with hot toluene to afford the title compound as a tan solid.

$^1$HNMR (CHCl$_3$, 300 MHz) δ 11.20 (s, 1H); 8.63 (d, 1H); 7.65-7.55 (m, 3H); 7.40 (m, 1H), 7.28 (m, 2H); 6.60 (m, 1H); 4.71 (s, 3H); 3.69 (s, 3H); 2.57 (s, 3H)

HRMS for C$_{18}$H$_{18}$NO$^+$ theoretical mass: 264.137 measured mass: 264.137.

EXAMPLE 8

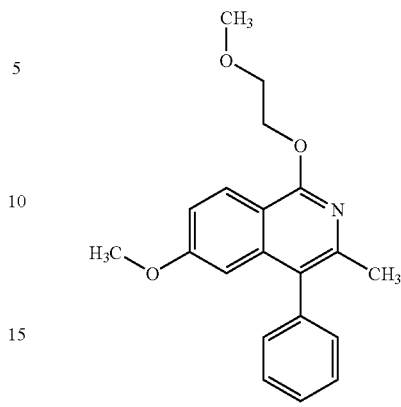

6-methoxy-1-(2-methoxyethoxy)-3-methyl-4-phe-
nylisoquinoline

Step A

To a solution of 2-benzyl-4-methoxybenzoic acid (14.2 g) in 600 mL CH$_2$Cl$_2$ was added a catalytic amount of DMF, followed by a solution of oxalyl chloride (8.7 g) in 100 mL of CH$_2$Cl$_2$. The reaction was stirred at room temp overnight, then concentrated and azeotroped with toluene (2×). The residue was dissolved in 700 mL CH$_2$Cl$_2$ and cooled to 0 C. Tert-butyl amine (13.9 g) was added, and the reaction was warmed to room temp. After 1.5 h, the reaction was quenched with 5% aqueous KHSO$_4$. The organic solution was separated, washed once with saturated aqueous sodium bicarbonate, dried (Na$_2$SO$_4$) and concentrated to give 15.9 g of 2-benzyl-N-(tert-butyl)-4-methoxybenzamide.

Step B

A solution of 2-benzyl-N-(tert-butyl)-4-methoxybenzamide (3.1 g) in 50 mL THF was sparged with Ar for 10 min. The solution was cooled to −78 C, and n-BuLi (10 mL of a 2.5 M hexanes solution) was added dropwise. After stirring for 1 h at −78 C, acetyl chloride (0.99 g) was added dropwise. The reaction was stirred for 10 min at −78 C, then for 1 h at room temp, then quenched with saturated aqueous NH$_4$Cl. The mixture was extracted with EtOAc (3×), then the combined organic solutions were washed with brine (1×), dried (Na$_2$SO$_4$) and concentrated. The residue was combined with 25 mL of 80% H$_3$PO$_4$ and heated to 100 C for 3 h. The reaction was poured into ice, then extracted with CHCl$_3$ (3×). The organic solutions were washed with saturated aqueous sodium bicarbonate, dried (Na$_2$SO$_4$) and concentrated. Trituration with diethyl ether provided 1.6 g of 6-methoxy-3-methyl-4-phenylisoquinolin-1(2H)-one.

Step C

A combination of 6-methoxy-3-methyl-4-phenylisoquinolin-1(2H)-one (0.85 g) and sodium hydride (60% dispersion in mineral oil, 240 mg) in 25 mL of DMF was heated at 60 C for 30 min, then cooled to room temp. 4-bromo-1-methoxyethane (1 mL) was added via syringe, and the reaction was stirred at room temp overnight, then quenched by addition of saturated aqueous NH$_4$Cl. The mixture was extracted with EtOAc (3×). The combined organic solutions were washed with water (1×) and brine (1×), then dried (Na$_2$SO$_4$) and concentrated. Flash chromatography (20% EtOAc/hexanes) gave a solid which was triturated with diethyl ether to provide the titled compound.

M+H calcd: 324; found: 324 (FAB)

EXAMPLE 9

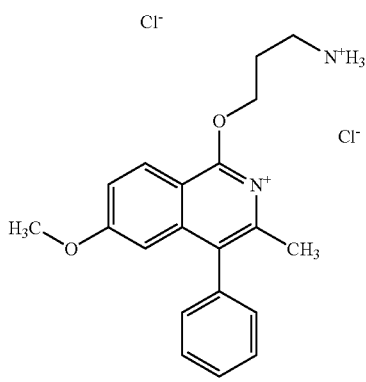

1-(3-ammoniopropoxy)-6-methoxy-3-methyl-4-phenylisoquinolinium dichloride

Step A
Following the Step C procedure for 6-methoxy-1-(2-methoxyethoxy)-3-methyl-4-phenylisoquinoline, using 3-phthalimido-1-bromopropane in place of 4-bromo-1-methoxyethane, 6-methoxy-1-(3-phthalimido-propoxy)-3-methyl-4-phenylisoquinoline was prepared.

Step B
To a mixture of 6-methoxy-1-(3-phthalimido-propoxy)-3-methyl-4-phenylisoquinoline (400 mg) in 30 mL methanol was added hydrazine (0.04 mL). The reaction was stirred overnight at room temp. 0.08 mL of additional hydrazine was added, and the reaction was heated overnight at 50 C, then poured into water and extracted with EtOAc (3×).). The combined organic solutions were washed with brine (1×), then dried ($Na_2SO_4$) and concentrated. Flash chromatography (50% EtOAc/hexanes) gave a solid which was treated with HCl in diethyl ether to provide the titled compound.

M+H calcd: 323; found: 323 (FAB)

EXAMPLE 10

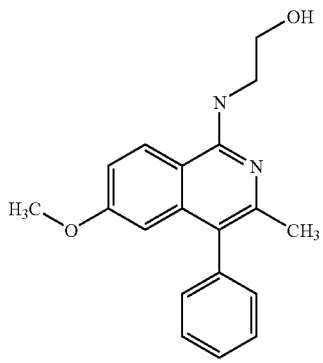

2-[(6-methoxy-3-methyl-4-phenylisoquinolin-1-yl)amino]ethanol

Step A
A mixture of 6-methoxy-3-methyl-4-phenylisoquinolin-1(2H)-one (3.0 g) and 12 mL of $POCl_3$ was heated to reflux for 1 h, then cooled to room temp and poured into ice. The mixture was extracted with EtOAc (3×). The combined organic solutions were washed with brine (1×) and saturated aqueous sodium carbonate (1×), then dried ($Na_2SO_4$) and concentrated. Flash chromatography (10% EtOAc/hexanes) gave 2.6 g of 1-chloro6-methoxy-3-methyl-4-phenylisoquinoline.

Step B
1-chloro-6-methoxy-3-methyl-4-phenylisoquinoline (0.29 g) was combined with 10 mL of ethanolamine and heated at 120 C for 5 h, then cooled to room temp. The reaction was poured into saturated aqueous sodium carbonate and extracted with EtOAc (3×). The combined organic solutions were washed with water (1×), then dried ($Na_2SO_4$) and concentrated. Flash chromatography (10% $MeOH/CHCl_2$) gave a solid which was recrystallized from ether/hexanes to give the titled compound.

Elemental analysis calcd for $C_{19}H_{20}N_2O_2$-0.25H2O: C, 72.93; H, 6.60; N, 8.95; N, 8.95; Found: C, 73.01; H, 6.56; N, 8.99.

EXAMPLE 11

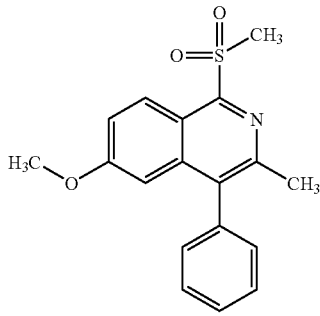

6-methoxy-3-methyl-1-(methylsulfonyl)-4-phenylisoquinoline

Step A
A mixture of 6-methoxy-3-methyl-4-phenylisoquinolin-1(2H)-one (0.7 g) and Lawesson's reagent (1.3 g) in 7 mL toluene was heated to reflux for 12 h. After cooling, the reaction was subjected directly to flash chromatography (5% $MeOH/CH_2Cl_2$) to give a solid, which was triturated with diethyl ether to provide 1.1 g of 6-methoxy-3-methyl-4-phenylisoquinoline-1(2H)-thione.

Step B
6-methoxy-3-methyl-4-phenylisoquinoline-1(2H)-thione (0.9 g) was combined with 20 mL DMF and 0.33 g of NaH (60% dispersion in mineral oil). The reaction was heated to 60 C and stirred for 30 min. Iodomethane (0.33 mL) was added, and the reaction was stirred overnight at 60 C, then poured into saturated aqueous $NH_4Cl$. The mixture was extracted with EtOAc (3×), then the combined organic solutions were washed with water (1×) and brine (1×), dried ($Na_2SO_4$) and concentrated to give 6-methoxy-3-methyl-1-(methylthio)-4phenylisoquinoline, which was used directly in the next step.

Step C
To a solution of 6-methoxy-3-methyl-1-(methylthio)-4-phenylisoquinoline (0.95 g) in 35 mL EtOAc and 7 mL methanol were added sodium tungstate (210 mg) and 30% aqueous hydrogen peroxide (1.5 mL). The reaction was heated to reflux overnight, then cooled and quenched with saturated aqueous sodium bisulfite. The mixture was extracted with EtOAc (3×), then the combined organic solutions were washed with brine (1×), dried (Na$_2$SO$_4$) and concentrated. The residue was triturated with diethyl ether/hexanes to give the titled compound.

Elemental analysis calcd for C$_{18}$H$_{17}$NO$_3$S: C, 66.03; H, 5.23; N, 4.27; Found: C, 66.17; H, 5.18; N, 4.20.

EXAMPLE 12

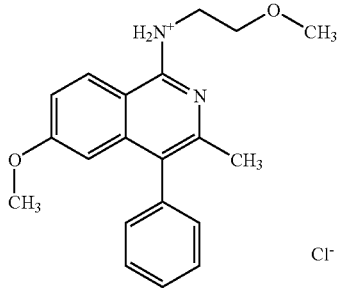

6-methoxy-N-(2-methoxyethyl)-3-methyl-4-phenyl-isoquinolin-1-ammonium chloride

Following the procedure for 2-[(6-methoxy-3-methyl-4-phenylisoquinolin-1-yl)amino]ethanol, using (in Step B) 2-methoxy-1-aminoethane in place of ethanolamine, the free base of the titled compound was synthesized. Treatment with excess HCl in EtOAc and trituration provided the titled compound.

Elemental analysis calcd for C$_{20}$H$_{22}$N$_2$O$_2$-HCl-0.25 H$_2$O: C, 66.10; H, 6.52; N, 7.71; Found: C, 66.22; H, 6.19; N, 7.73.

EXAMPLE 13

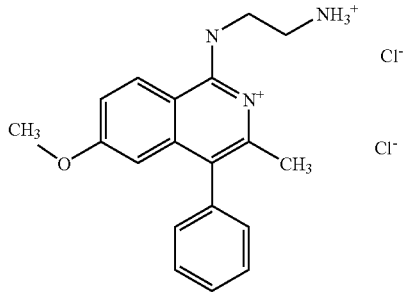

1-[(2-ammonioethyl)amino]-6-methoxy-3-methyl-4-phenylisoquinolinium dichloride

Step A

Following the procedure for 2-[(6-methoxy-3-methyl-4-phenylisoquinolin-1-yl)amino]ethanol, using (in Step B) tert-butyl-2-aminoethylcarbamate in place of ethanolamine, tert-butyl 2-[(6-methoxy-3-methyl-4-phenylisoquinolin-1-yl)amino]ethylcarbamate was synthesized.

Step B

Tert-butyl 2-[(6-methoxy-3-methyl-4-phenylisoquinolin-1-yl)amino]ethylcarbamate (0.61 g) was treated with 100 mL of HCl-saturated EtOAc. The reaction was stirred at 0 C for 30 min, then at room temp for 3.5 h, then concentrated to dryness. Recrystallization from methanol/EtOAc provided the titled compound.

M+H calcd: 307; found: 307 (FAB)

EXAMPLE 14

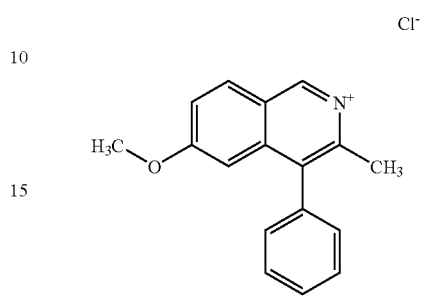

6-methoxy-3-methyl-4-phenylisoquinolinium chloride 1-chloro-6-methoxy-3-methyl-4-phenylisoquinoline (0.55 g) in 25 mL EtOH was treated with 120 mg KOH and 30 mg Pd—C (10%). The reaction was shaken under an H$_2$ atmosphere (50 psi) for 20 h. The reaction was filtered through celite and concentrated to dryness, then dissolved in isopropanol and treated with excess HCl. Crystallization from isopropanol/diethyl ether gave the titled compound.

Elemental analysis calcd for C$_{17}$H$_{15}$NO—HCl-0.5 H$_2$O: C, 69.26; H, 5.81; N, 4.75; Found: C, 69.10; H, 6.06; N, 4.63.

EXAMPLE 15

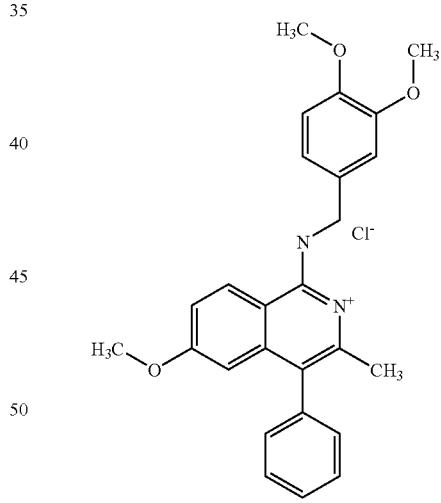

1-[(3,4-dimethoxybenzyl)amino]-6-methoxy-3-methyl-4-phenylisoquinolinium chloride Following the procedure for 2-[(6-methoxy-3-methyl-4-phenylisoquinolin-1-yl)amino]ethanol, using (in Step B) 3,4-dimethoxybenzylamine in place of ethanolamine, the free base of the titled compound was synthesized. Treatment with excess HCl in diethyl ether and trituration provided the titled compound Elemental analysis calcd for C$_{26}$H$_{26}$N$_2$O$_3$-HCl: C, 69.25; H, 6.04; N, 6.21; Found: C, 69.56; H, 6.32; N, 6.06. .

EXAMPLE 16

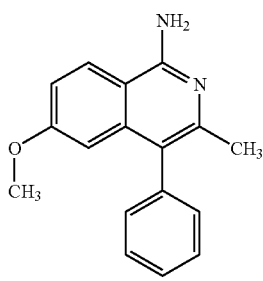

6-methoxy-3-methyl-4-phenylisoquinolin-1-amine

The free base of 1-[(3,4-dimethoxybenzyl)amino]-6-methoxy-3-methyl-4-phenylisoquinolinium chloride was treated with 5 mL of $CH_2Cl_2$ and 10 mL of trifluoroacetic acid. The reaction was stirred at room temp for 2 h, then concentrated to dryness. The residue was combined with saturated aqueous sodium carbonate, and the mixture was extracted with EtOAc (3×). The combined organic solutions were dried ($Na_2SO_4$) and concentrated. Recrystallization from EtOAc/hexanes gave a solid which was further purified by flash chromatography (0-1% MeOH/ammonia-saturated $CHCl_3$). The solid thus obtained was triturated with hexanes to give the titled compound.

Elemental analysis calcd for $C_{17}H_{16}N_2O$-0.25 $H_2O$: C, 75.95; H, 6.19; N, 10.42; Found: C, 76.13; H, 6.14; N, 10.13.

EXAMPLE 17

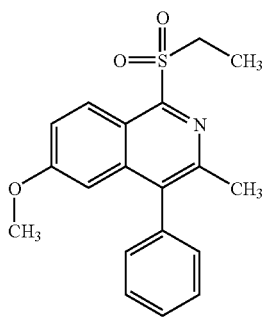

1-(ethylsulfonyl)-6-methoxy-3-methyl-4-phenylisoquinoline

Following the procedure 6-methoxy-3-methyl-1-(methylsulfonyl)-4-phenylisoquinoline, using (in Step B) iodoethane in place of iodomethane, the titled compound was synthesized.

Elemental analysis calcd for $C_{19}H_{19}NO_3S$: C, 66.84; H, 5.61; N, 4.10; Found: C, 66.93; H, 5.82; N, 4.01.

EXAMPLE 18

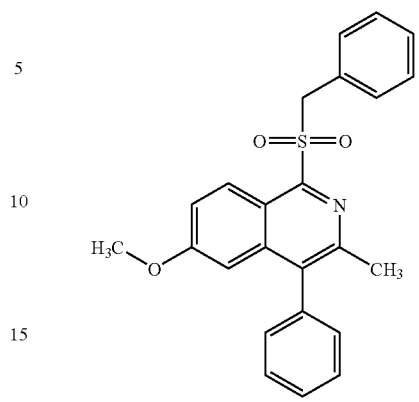

1-(benzylsulfonyl)-6-methoxy-3-methyl-4-phenyl-isoquinoline

Following the procedure 6-methoxy-3-methyl-1-(methylsulfonyl)-4-phenylisoquinoline, using (in Step B) benzyl bromide in place of iodomethane, the titled compound was synthesized.

Elemental analysis calcd for $C_{24}H_{21}NO_3S$-0.25 $H_2O$: C, 70.65; H, 5.31; N, 3.43; Found: C, 70.88; H, 5.20; N, 3.40.

EXAMPLE 19

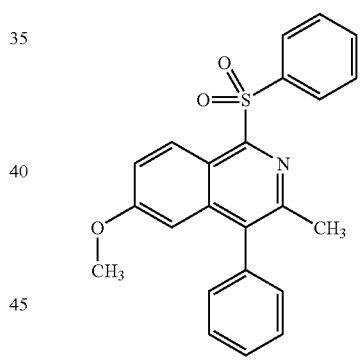

6-methoxy-3-methyl-4-phenyl-1-(phenylsulfonyl) isoquinoline

To a solution of 1-chloro-6-methoxy-3-methyl-4-phenyl-isoquinoline (0.24 g) in 20 mL DMF was added benzenesulfinic acid, sodium salt dihydrate (0.60 g). The reaction was heated at 120 C overnight, then poured into water and extracted with EtOAc (3×). The combined organic solutions were washed with water (1×) and brine (1×), dried ($Na_2SO_4$) and concentrated. To a solution of the residue in 20 mL DMF was added benzenesulfinic acid, sodium salt dihydrate (0.74 g). The reaction was heated at 160 C overnight, then poured into water and extracted with EtOAc (3×). The combined organic solutions were washed with water (1×) and brine (1×), dried ($Na_2SO_4$) and concentrated. The residue was recrystallized from ethyl ether/hexanes, then further purified by flash chromatography (5% to 30% EtOAc/hexanes). A second recrystallization from ethyl ether/hexanes gave the titled compound.

Elemental analysis calcd for $C_{23}H_{19}NO_3S \cdot 0.25\ H_2O$: C, 70.11; H, 4.99; N, 3.56; Found: C, 70.20; H, 5.06; N, 3.57.

EXAMPLE 20

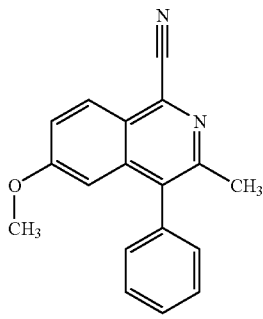

6-methoxy-3-methyl-4-phenylisoquinoline-1-carbonitrile

To a solution of 1-chloro-6-methoxy-3-methyl-4-phenylisoquinoline (0.35 g) in 20 mL DMF was added potassium cyanide (0.25 g). The reaction was heated at 60 C for 5 h, then at 120 C overnight, then at 140 C for a second overnight period. The reaction was poured into water and extracted with EtOAc (3×). The combined organic solutions were washed with water (1×) and brine (1×), dried ($Na_2SO_4$) and concentrated. Flash chromatography (5% to 10% EtOAc/hexanes) gave a solid which was recrystallized from hexanes to give the titled compound.

M+H calcd: 275; found: 275 (FAB)

EXAMPLE 21

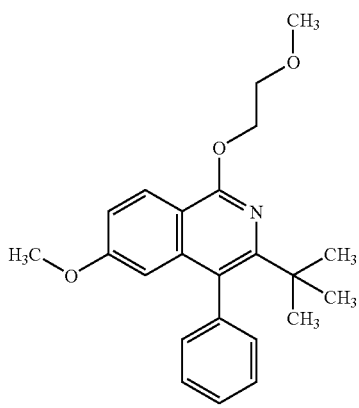

3-tert-butyl-6-methoxy-1-(2-methoxyethoxy)-4-phenylisoquinoline

Following the procedure for 6-methoxy-1-(2-methoxyethoxy)-3-methyl-4-phenylisoquinoline, using (in Step B) pivaoyl chloride in place of acetyl chloride, the title compound was synthesized.

Elemental analysis calcd for $C_{23}H_{27}NO_3 \cdot 0.25$ Hexane: C, 76.03; H, 7.94; N, 3.62; Found: C, 76.41; H, 8.02; N, 3.82.

EXAMPLE 22

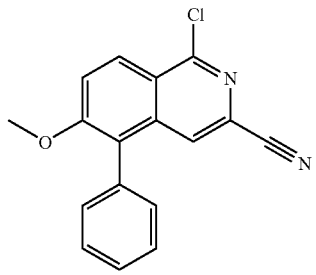

1-chloro-6-methoxy-4-phenylisoquinoline-3-carbonitrile

A mixture of 6-methoxy-1-oxo-4-phenyl-1,2-dihydroisoquinoline-3-carbonitrile (200 mg) and $POCl_3$ (10 mL) was heated to 90 C for 18 h. The reaction was concentrated, and the residue was dissolve in EtOAc, cooled to 0 C, and quenched by careful addition of saturated aqueous sodium bicarbonate. The mixture was partitioned between saturated aqueous sodium bicarbonate and EtOAc. The aqueous solution was washed twice with EtOAc. The combined organic solutions were dried ($Na_2SO_4$) and concentrated. Flash chromatography (25 g silica, 3-30% EA/hex) gave a white solid.

HRMS(ES) calcd: 295.0633; found: 295.0625

EXAMPLE 23

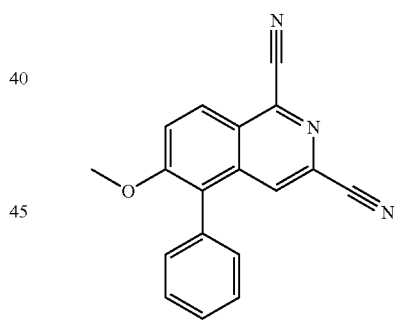

6-methoxy-4-phenylisoquinoline-1,3-dicarbonitrile

To a solution of 100 mg of 1-chloro-6-methoxy-4-phenylisoquinoline-3-carbonitrile in 6.9 mL of propionitrile and 0.36 mL of water were added 25 mg NaCN and 8 mg DMAP. The reaction was heated at 97 C for 17 h, then at 107 C for 4 h. An additional 157 mg NaCN and 23 mg DMAP were added, and the reaction was heated at 100 C for 20 h. The reaction was cooled to room temperature and partitioned between EtOAc and saturated aqueous sodium bicarbonate. The organic solution was washed once with brine, dried (Na2SO4) and concentrated. Flash chromatography (10-40% EA/hexanes, 35 g silica) gave a pale yellow solid.

HRMS(ES) calcd: 286.0975; found: 286.0974.

EXAMPLE 24

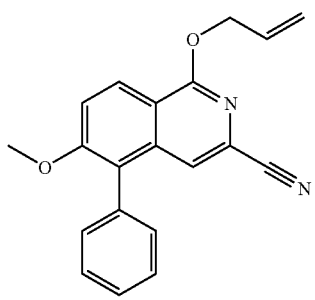

1-(allyloxy)-6-methoxy-4-phenylisoquinoline-3-carbonitrile

To a suspension of NaH (60% in mineral oil, 14 mg) in 2 mL TEF was added 23 uL of allyl alcohol. The mixture was stirred for 15 min at room temp, then 100 mg of 1-chloro-6-methoxy-4-phenylisoquinoline-3-carbonitrile in 1.5 ml THF was added via cannula. The reaction was heated to 66 C for 16 h, then cooled to room temp, quenched with saturated aqueous NH4Cl, and partitioned between EtOAc and saturated aqueous sodium bicarbonate. The organic solution was washed once with brine, then dried (Na2SO4) and concentrated. Flash chromatography (35 g silica, 3-25% EA/hex) gave a white solid.

HRMS(ES) calcd: 317.1285; found: 317.1280

EXAMPLE 25

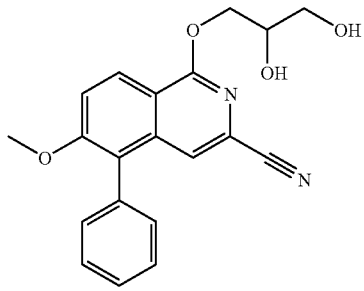

1-(2,3-dihydroxypropoxy)-6-methoxy-4-phenylisoquinoline-3-carbonitrile 1-(allyloxy)-6-methoxy-4-phenylisoquinoline-3-carbonitrile was suspended in 2.4 mL acetone and 1 mL water. 0.24 ml of OsO4 soln (2.5% in 2-Me-2-propanol) was added, followed by 28 mg of NMO and 1.5 mL of additional acetone. The reaction was stirred at room temp for 17 h, then diluted with 1:1 saturated aqueous sodium bicarbonate:saturated aqueous $Na_2SO_3$. The mixture was partitioned between EtOAc and saturated aqueous sodium bicarbonate, and the aqueous solution was extracted once with EtOAc. The organic solutions were dried ($Na_2SO_4$) and concentrated. Flash chromatography (60-100% EA/hexanes, 40 g silica) gave a white solid.

HRMS(ES) calcd: 357.1339; found: 357.1333

EXAMPLE 26

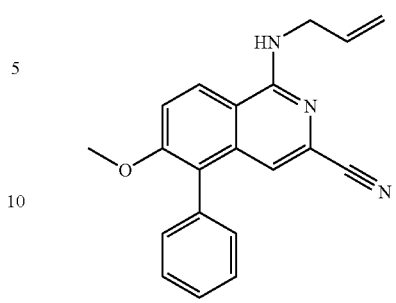

(allylamino)-6-methoxy-4-phenylisoquinoline-3-carbonitrile

To a suspension of 104 mg of 1-chloro-6-methoxy-4-phenylisoquinoline-3-carbonitrile in nBuOH was added 252 uL of allylamine. The reaction was heated at 210 C in a microwave reactor for 1 h, then partitioned between EA and saturated aqueous sodium bicarbonate. The organic solution was washed with brine once, then dried (Na2SO4) and concentrated. Flash chromatography (540% EA/hex, Gilson, 40 g silica) gave a pink solid.

HRMS(ES) calcd: 316.1444; found: 316.1440

EXAMPLE 27

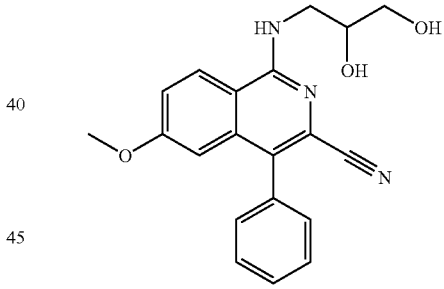

1-[(2,3-dihydroxypropyl)amino]-6-methoxy-4-phenylisoquinoline-3-carbonitrile

To a solution of 95 mg of (allylamino)-6-methoxy-4-phenylisoquinoline-3-carbonitrile in 9 ml, acetone and 3.5 mL water were added 0.36 ml $OsO_4$ soln (2.5% in 2-Me-2-propanol) and 42 mg of NMO. The reaction was stirred at room temp for 19 h, then diluted with 1:1 saturated aqueous sodium bicarbonate:saturated aqueous $Na_2SO_3$. The mixture was partitioned between EA and saturated aqueous sodium bicarbonate, and the organic solution was washed once with brine. The combined aqueous solution were extracted once with EtOAc. The combined organic solutions were dried ($Na_2SO_4$) and concentrated. Flash chromatography (0-4% MeOH(10% NH4OH)/EA, 40 g silica) gave a tan solid.

HRMS(ES) calcd: 350.1499; found: 350.1494

EXAMPLE 28

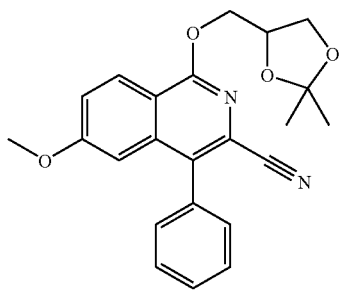

1-[(2,2-dimethyl-1,3-dioxolan-4-yl)methoxy]-6-methoxy-4-phenylisoquinoline-3-carbonitrile Following the procedure for 1-(allyloxy)-6-methoxy-4-phenylisoquinoline-3-carbonitrile, using solketal in place of allyl alcohol, the title compound was synthesized.

HRMS(ES) calcd: 391.1653; found: 391.1652

EXAMPLE 29

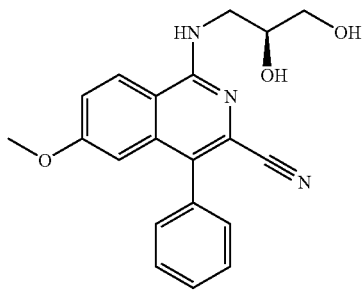

1-{[(2S)-2,3-dihydroxypropyl]amino}-6-methoxy-4-phenylisoquinoline-3-carbonitrile Following the procedure for 1-(allylamino)-6-methoxy-4-phenylisoquinoline-3-carbonitrile, using 2S-3-amino-1,2-propanediol in place of allylamine, the title compound was synthesized.

HRMS(ES) calcd: 350.1499; found: 350.1485

EXAMPLE 30

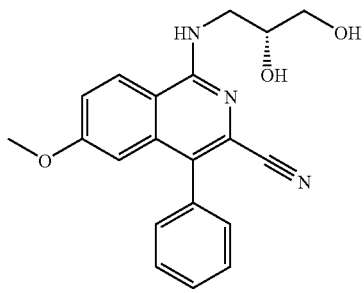

1-{[(2R)-2,3-dihydroxypropyl]amino}-6-methoxy-4-phenylisoquinoline-3-carbonitrile Following the procedure for 1-(allylamino)-6-methoxy-4-phenylisoquinoline-3-carbonitrile, using 2R-3-amino-1,2-propanediol in place of allylamine, the title compound was synthesized.

$^1$H NMR (500 MHz, DMSO-d6) δ 8.38 (d, J=9 Hz, 1H); 7.77 (t, J=Hz, 1H); 7.59-7.51 (m, 3H); 7.46 (d, J-7 Hz, 2H); 7.37 (dd, J=9.3 Hz, 1H); 6.71 (d, J=3 Hz, 1H); 4.90 (d, J=5 Hz, 1H); 4.63 (t, J=6 Hz, 1H); 3.86-3.81 (m, 1H); 3.71 (s, 3H); 3.61 (dt, J=13, 5 Hz, 1H); 3.46-3.39 (m, 3H).

EXAMPLE 31

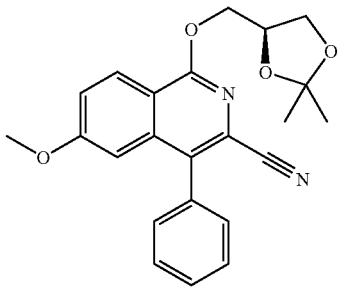

1-{[(4S)-2,2-dimethyl-1,3-dioxolan-4-yl]methoxy}-6-methoxy4-phenylisoquinoline-3-carbonitrile Following the procedure for 1-(allyloxy)-6-methoxy-4-phenylisoquinoline-3-carbonitrile, using (S)-(+)-2,2,-dimethyl-1,3-dioxolane-4-methanol in place of allyl alcohol, the title compound was synthesized.

HRMS(ES) calcd: 391.1653; found: 391.1665

EXAMPLE 32

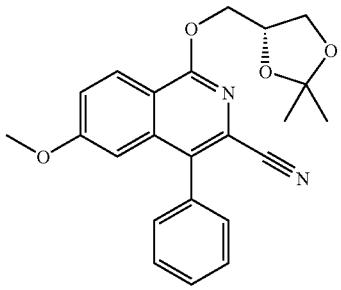

1-{[(4R)-2,2-dimethyl-1,3-dioxolan-4-yl]methoxy}-6-methoxy-4-phenylisoquinoline-3-carbonitrile Following the procedure for 1-(allyloxy)-6-methoxy-4-phenylisoquinoline-3-carbonitrile, using (R)-(−)-2,2,-dimethyl-1,3-dioxolane-4-methanol in place of allyl alcohol, the title compound was synthesized.

HRMS(ES) calcd: 391.1653; found: 391.1665

EXAMPLE 33

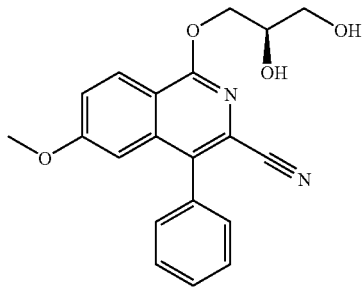

1-{[(2R)-2,3-dihydroxypropyl]oxy}-6-methoxy-4-phenylisoquinoline-3-carbonitrile

A round-bottomed flask containing 162 mg of 1-{[(4S)-2,2-dimethyl-1,3-dioxolan-4-yl]methoxy}-6-methoxy-4-phenylisoquinoline-3-carbonitrile was cooled to 0 C. A 0 C solution composed of 3 mL THF/1 mL conc HCl was added, and the reaction was stirred at 0 C for exactly 10 min. 20 mL of 10% aqueous $K_2CO_3$ was added as quickly as possible (vigorous). The resulting mixture was extracted once with EtOAc. The organics were dried ($Na_2SO_4$) and concentrated. Flash chromatography (40 g silica, 60-100% EA/hexanes) gave a white solid.

$^1$H NMR (500 MHz, CDCl3) δ 8.27 (d, J=9 Hz, 1H); 7.59-7.52 (m, 3H); 7.45 (dd, J=8, 1 Hz, 2H); 7.31 (dd, J=9, 2 Hz, 1H); 6.89 (d, J=2 Hz, 1H); 4.73 (dd, J=12, 4 Hz, 1H); 4.69 (dd, J=12, 6 Hz, 1H); 4.25-4.20 (m, 1H); 3.88-3.83 (m, 1H); 3.80-3.75 (m, 1); 3.77 (s, 3H); 3.20 (d, J=5 Hz, 1H); 2.31 (t, J=6 Hz, 1H).

EXAMPLE 34

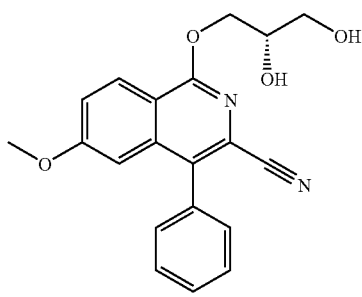

1-{[(2S)-2,3-dihydroxypropyl]oxy}-6-methoxy-4-phenylisoquinoline-3-carbonitrile

Following the procedure for 1-{[(2R-2,3-dihydroxypropyl]oxy}-6-methoxy-4-phenylisoquinoline-3-carbonitrile, using 1-{[(4R)-2,2-dimethyl-1,3-dioxolan-4-yl]methoxy}-6-methoxy-4-phenylisoquinoline-3-carbonitrile in place of 1-{[(4S)-2,2-dimethyl-1,3-dioxolan-4-yl]methoxy}-6-methoxy-4-phenylisoquinoline-3-carbonitrile, the title compound was synthesized.

$^1$H NMR (500 MHz, CDCl3) δ 8.27 (d, J=9 Hz, 1H); 7.59-7.52 (m, 3H); 7.45 (dd, J=8, 1 Hz, 2H); 7.31 (dd, J=9, 2 Hz, 1H); 6.89 (d, J=2 Hz, 1H); 4.73 (dd, J=12, 4 Hz, 1); 4.69 (dd, J=12, 6 Hz, 1H); 4.25-4.20 (m, 1H); 3.88-3.83 (m, 1H); 3.80-3.75 (m, 1H); 3.77 (s, 3H); 3.20 (d, J=5 Hz, 1H); 2.31 (t, J=6 Hz, 1H).

EXAMPLE 35

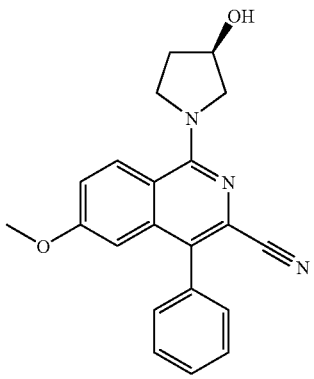

1-[(3R)-3-hydroxypyrrolidin-1-yl]-6-methoxy-4-phenylisoquinoline-3-carbonitrile

Following the procedure for 1-(allylamino)-6-methoxy-4-phenylisoquinoline-3-carbonitrile, using (R)-3-pyrrolidinol in place of allylamine, the title compound was synthesized.
HRMS(ES) calcd: 346.1550; found: 346.1554

EXAMPLE 36

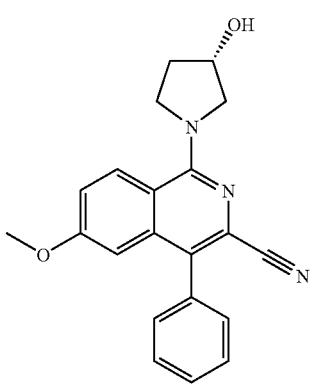

1-[(3S)-3-hydroxypyrrolidin-1-yl]-methoxy-4-phenylisoquinoline-3-carbonitrile

Following the procedure for 1-(allylamino)-6-methoxy-4-phenylisoquinoline-3-carbonitrile, using (S)-3-pyrrolidinol in place of allylamine, the title compound was synthesized.
HRMS(ES) calcd: 346.1550; found: 346.1553

EXAMPLE 37

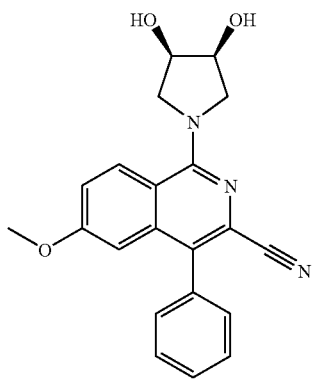

1-[cis-3,4-dihydroxypyrrolidin-1-yl]6-methoxy-4-phenylisoquinoline-3-carbonitrile

EXAMPLE 38

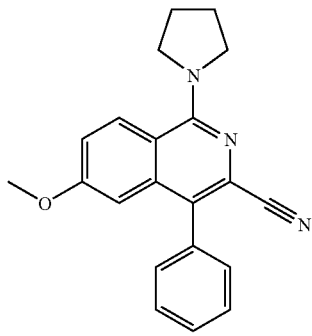

6-methoxy-4-phenyl-1-pyrrolidin-1-ylisoquinoline-3-carbonitrile

Step A

Mixture of 6-methoxy-4-phenyl-1-(3-pyrroline)-1-ylisoquinoline-3-carbonitrile and 6-methoxy-4-phenyl-1-pyrrolidin-1-ylisoquinoline-3-carbonitrile.

To a suspension of 100 mg of 1-chloro-6-methoxy-4-phenylisoquinoline-3-carbonitrile in nBuOH was added 260 uL of a 65:35 mixture of 3-pyrroline:pyrrolidine. The reaction was heated at 210 C in a microwave reactor for 1 h, then partitioned between EA and saturated aqueous sodium bicarbonate. The organic solution was washed with brine once, then dried ($Na_2SO_4$) and concentrated. Flash chromatography (5-30% EA/hex, 40 g silica) gave 86 mg of a white solid.

HRMS(ES) calcd: 316.1444; found: 316.1440

Step B

To a suspension of 86 mg of the mixture of 6-methoxy-4-phenyl-1-(3-pyrroline)-1-ylisoquinoline-3-carbonitrile and 6-methoxy-4-phenyl-1-pyrrolidin-1-ylisoquinoline-3-carbonitrilein in 4.8 mL acetone and 2 mL water were added 0.32 ml $OsO_4$ soln (2.5% in 2-Me-2-propanol) and 37 mg of NMO. The reaction was stirred at room temp for 5 h, after which 0.32 ml additional $OsO_4$ solution was added. After stirring for an additional 16 h, the reaction was diluted with 1:1 saturated aqueous sodium bicarbonate:saturated aqueous $Na_2SO_3$. The mixture was partitioned between EA and saturated aqueous sodium bicarbonate, and the organic solution was washed once with brine. The combined aqueous solution were extracted once with EtOAc. The combined organic solutions were dried ($Na_2SO_4$) and concentrated. Flash (5/95/0 to 99/0/1 EA/hex/MeOH, 40 g silica) gave 38 mg of 1-[cis-3,4-dihydroxypyrrolidin-1-yl]-6-methoxy-4-phenylisoquinoline-3-carbonitrile as a tan solid. HRMS(ES) calcd: 362.1499; found: 362.1500. Further purification by reverse phase HPLC gave 6-methoxy-4-phenyl-1-pyrrolidin-1-ylisoquinoline-3-carbonitrile as a white solid. HRMS(ES) calcd: 330.1601; found: 330.1603.

EXAMPLE 39

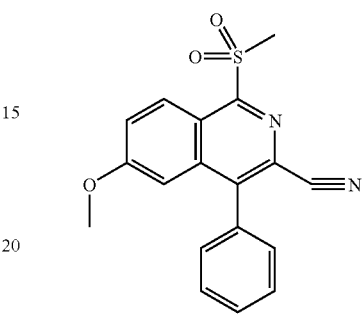

6-methoxy-1-(methylsulfonyl)-4-phenylisoquinoline-3-carbonitrile

Step A

To a solution of 1-chloro-6-methoxy-4-phenylisoquinoline-3-carbonitrile (577 mg) in 12 mL DMF was added 95% $NaSCH_3$ (173 mg). The reaction was stirred at room temp for 1 h, then quenched with saturated aqueous $KHSO_4$. Aqueous workup gave 610 mg of 6-methoxy-1-(methylthio)-4-phenylisoquinoline-3-carbonitrile, which was used directly in the next reaction.

Step B

To a mixture of 6-methoxy-1-(methylthio)-4-phenylisoquinoline-3-carbonitrile (550 mg) and 21 mL EtOAc were added methanol (4 mL), sodium tungstate dihydrate (118 mg), and 30% hydrogen peroxide solution (0.850 mL). The reaction was heated at reflux for 6 h, then stirred at 50 C overnight. The reaction was cooled, then diluted with EtOAc and washed with water (1×) and brine (1×). The organic solution was dried over sodium sulfate and purified by flash chromatography (30% EtOAc/hexanes) to give a solid which was crystallized from diethyl ether to give the titled compound.

M+H calcd: 339; found: 339 (FAB)

EXAMPLE 40

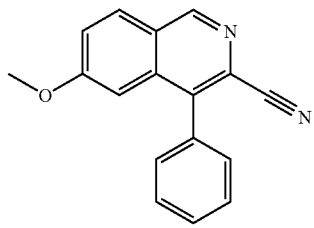

6-methoxy-4-phenylisoquinoline-3-carbonitrile

A mixture of 1-chloro-6-methoxy-4-phenylisoquinoline-3-carbonitrile (200 mg), 5% Pd/$BaSO_4$ (50 mg), and 20 mL methanol was stirred under 1 atm hydrogen for 18 h. 5 mL of CH$_2$Cl$_2$ was then added, as was an additional 50 mg Pd/BaSO$_4$. After stirring overnight, the reaction was filtered, concentrated, and purified by flash chromatography (30% EtOAc/hexanes) to give the titled compound.

M+H calcd: 261; found: 261 (FAB)

EXAMPLE 41

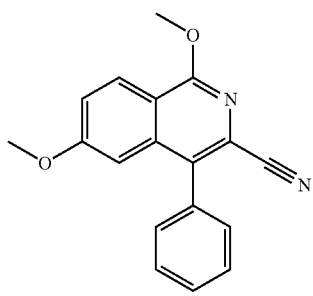

1,6-dimethoxy-4-phenylisoquinoline-3-carbonitrile

To a solution of 1-chloro-6-methoxy-4-phenylisoquinoline-3-carbonitrile (50 mg) in 1 mL of DMF was added NaOMe (3 equivalents). The reaction was stirred at room temp overnight, then concentrated and purified by flash chromatography (30% EtOAc/hexanes). Trituration (ether/hexanes) of the concentrated material gave the titled compound.

M+H calcd: 291; found: 291 (FAB)

EXAMPLE 42

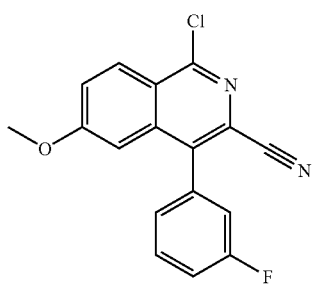

1-chloro-4-(3-fluorophenyl)-6-methoxyisoquinoline-3-carbonitrile 42 mg of 6-methoxy-1-oxo-4-(3-fluorophenyl)-1,2-dihydroisoquinoline-3-carbonitrile in 3 mL POCl3 was heated from room temp to 80 C. After 2 h, the temperature was raised to 90 C, and heating was continued for 20 h. The reaction was concentrated, redissolved in EtOAc, cooled to 0 C, and saturated aqueous sodium bicarbonate was added dropwise to quench the remaining reagent. The mixture was separated, and the aqueous solution was extracted with EtOAc (3×). The combined organic solutions were dried over MgSO4 and concentrated. Flash chromatography (3% to 30% EtOAc in hexanes) gave a white solid.

HRMS(ES) found: 313.0553; calcd: 313.0539

EXAMPLE 43

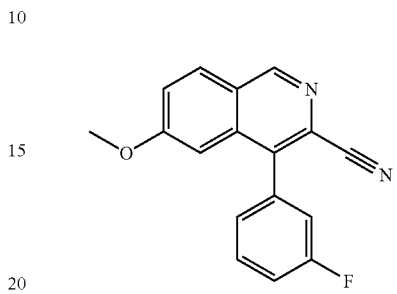

4-3-fluorophenyl)-6-methoxyisoquinoline-3-carbonitrile 18 mg of chloro-4-(3-fluorophenyl)-6-methoxyisoquinoline-3-carbonitrile was dissolved in 4 mL EtOH, and 230 uL of 1 N NaOH was added followed by 15 mg of 10% Pd on Carbon catalyst. The reaction was stirred under H$_2$ at atmospheric pressure for 6 h, then filtered through celite, concentrated and purified by reverse phase HPLC to give a white solid.

HRMS(ES) found: 279.0916; calcd: 279.0928

EXAMPLE 44

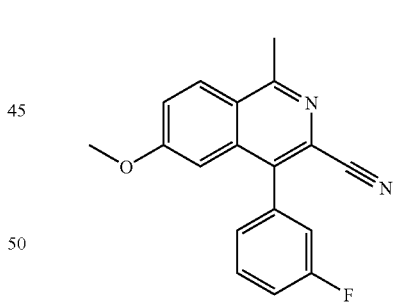

4-3-fluorophenyl)-6-methoxy-1-methylisoquinoline-3-carbonitrile

A mixture of 1-chloro-4-(3-fluorophenyl)-6-methoxyisoquinoline-3-carbonitrile (50 mg), trimethylboroxine (20 mg), Pd(PPh$_3$)$_4$ (18 mg) and cesium carbonate (156 mg) in 1.5 mL dioxane was heated at 110 C overnight. The reaction was filtered through a celite pad, which was washed thoroughly with THF, and concentrated. Flash chromatography (3% to 40% EtOAc/hexanes) gave a white solid.

HRMS(ES) found: 293.1078; calcd: 293.1085

EXAMPLE 45

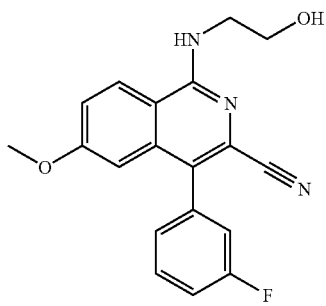

4-(3-fluorophenyl)-1-[(2-hydroxyethyl)amino]-6-methoxyisoquinoline-3-carbonitrile 2-aminoethanol (98 mg) was added to a suspension of 1-chloro-4-3-fluorophenyl)-6-methoxyisoquinoline-3-carbonitrile (50 mg) in 2 mL of isopropanol, and the mixture was heated at 85 C overnight. The reaction was cooled to room temp and concentrated. Flash chromatography (0% to 3% YieOk in EtOAc) gave a white solid.

HRMS(ES) found: 338.1297; calcd: 338.1299

EXAMPLE 46

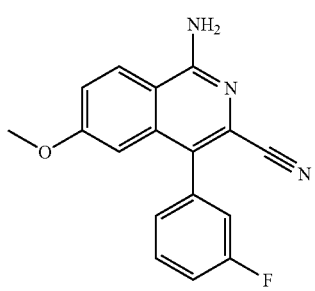

1-amino-4-(3-fluorophenyl)-6-methoxyisoquinoline-3-carbonitrile

A suspension of 1-chloro-4-(3-fluorophenyl)-6-methoxy-isoquinoline-3-carbonitrile in 1.5 mL of 2M NH$_3$ in isopropanol was heated in a sealed tube at 90 C overnight, then heated in a microwave reactor at 170 C for 24 h. The reaction was concentrated and purified by reverse-phase HPLC to give a white solid.

HRMS(ES) found: 294.1046; calcd: 294.1037

EXAMPLE 47

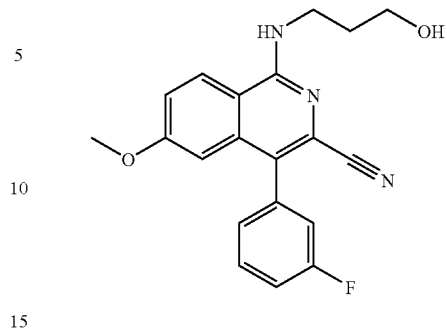

4-(3-fluorophenyl)-1-[(3-hydroxypropyl)amino]-6-methoxyisoquinoline-3-carbonitrile Following the procedure for 4-(3-fluorophenyl)-1-[(2-hydroxyethyl)amino]-6-methoxyisoquinoline-3-carbonitrile, using 3-amino-1-propanol in place of 2-aminoethanol, the title compound was synthesized.

HRMS(ES) found: 352.1464; calcd: 352.1456

EXAMPLE 48

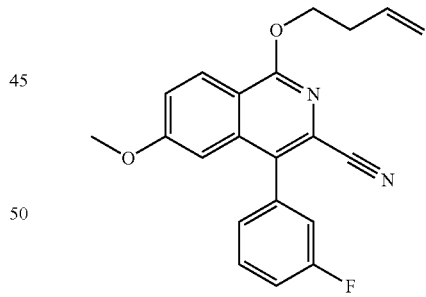

1-(but-3-enyloxy)-4-(3-fluorophenyl)-6-methoxyisoquinoline-3-carbonitrile

Following the procedure for 1-(allyloxy)-6-methoxy-4-phenylisoquinoline-3-carbonitrile, using 1-chloro-4-(3-fluorophenyl)-6-methoxyisoquinoline-3-carbonitrile in place of 1-chloro-6-methoxy-4-phenylisoquinoline-3-carbonitrile- and 1-buten-4-ol in place of allyl alcohol, the title compound was synthesized.

HRMS(ES) found: 349.1343; calcd: 349.1347

EXAMPLE 49

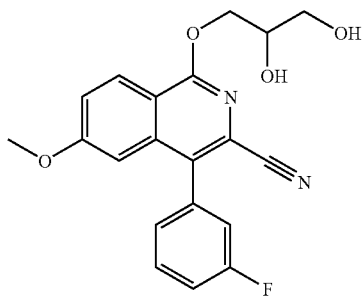

1-(2,3-dihydroxypropoxy)-4-(3-fluorophenyl)-6-methoxyisoquinoline-3-carbonitrile Step A Following the procedure for 1-(allyloxy)-6-methoxy-4-phenylisoquinoline-3-carbonitrile, using 1-chloro-4-(3-fluorophenyl)-6-methoxyisoquinoline-3-carbonitrile in place of 1-chloro-6-methoxy-4-phenylisoquinoline-3-carbonitrile, 1-(allyloxy)-6-methoxy-4-(3-fluorophenyl)isoquinoline-3-carbonitrile was synthesized.

Step B

Following the procedure for 1-(2,3-dihydroxypropoxy)-6-methoxy-4-phenylisoquinoline-3-carbonitrile, using 1-(allyloxy)-6-methoxy-4-(3-fluorophenyl)isoquinoline-3-carbonitrile in place of 1-(allyloxy)-6-methoxy-4-phenylisoquinoline-3-carbonitrile, the title compound was synthesized.

HRMS(ES) found: 369.1239; calcd: 369.1245

1-(2,3-dihydroxypropoxy)-4-(3-fluorophenyl)-4-methoxyisoquinoline-3-carbonitrile was resolved into its constituent enantiomers by chiral HPLC. The two pure enantiomers were identical to the racemic compound by HRMS and NMR.

EXAMPLE 50

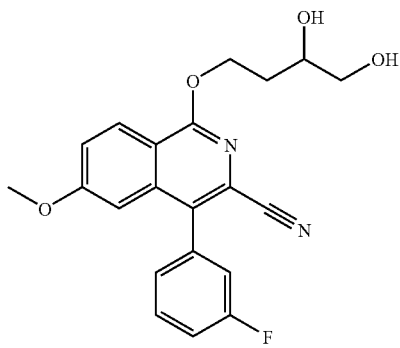

1-(3,4-dihydroxybutoxy)-4-(3-fluorophenyl)-6-methoxyisoquinoline-3-carbonitrile

Following the procedure for 1-(2,3-dihydroxypropoxy)-6-methoxy-4-phenylisoquinoline-3-carbonitrile, using 1-(but-3-enyloxy)-4-(3-fluorophenyl)-6-methoxyisoquinoline-3-carbonitrile in place of 1-(allyloxy)-6-methoxy-4-phenylisoquinoline-3-carbonitrile, the title compound was synthesized.

HRMS(ES) found: 383.1400; calcd: 383.1402

1-(3,4-dihydroxybutoxy)-4-(3-fluorophenyl)-6-methoxyisoquinoline-3-carbonitrile was resolved into its constituent enantiomers by chiral HPLC. The two pure enantiomers were identical to the racemic compound by HRMS and NMR.

EXAMPLE 51

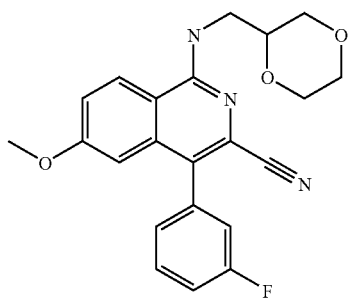

1-[(1,4-dioxan-2-ylmethyl)amino]-4-(3-fluorophenyl)-6-methoxyisoquinoline-3-carbonitrile Following the procedure for 4-(3-fluorophenyl)-1-[(2-hydroxyethyl)amino]-6-methoxyisoquinoline-3-carbonitrile, using 1,4-dioxan-2-ylmethylamine in place of 2-aminoethanol, the title compound was synthesized.

HRMS(ES) found: 394.1575; calcd: 394.1562

EXAMPLE 52

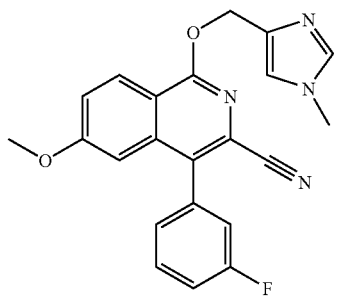

4-(3-fluorophenyl)-6-methoxy-1-[(1-methyl-1H-imidazol-4-yl)methoxy]isoquinoline-3-carbonitrile Following the procedure for 1-(allyloxy)-6-methoxy-4-phenylisoquinoline-3-carbonitrile, using 1-chloro-4-(3-fluorophenyl)-6-methoxyisoquinoline-3-carbonitrile in place of 1-chloro-6-methoxy-4-phenylisoquinoline-3-carbonitrile and (1-methyl-1H-imidazol-4-yl)methanol in place of allyl alcohol, the title compound was synthesized.

HRMS(ES) found: 389.1406; calcd: 389.1409

EXAMPLE 53

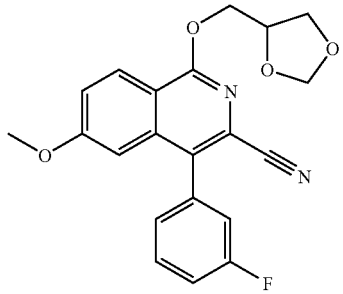

1-(1,3-dioxolan-4-ylmethoxy)-4-(3-fluorophenyl)-6-methoxyisoquinoline-3-carbonitrile

EXAMPLE 54

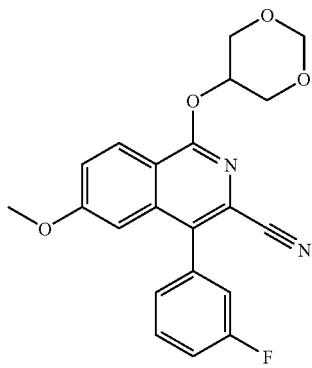

1-1,3-dioxan-5-yloxy)-4-(3-fluorophenyl)-6-methoxyisoquinoline-3-carbonitrile

Following the procedure for 1-(allyloxy)-6-methoxy-4-phenylisoquinoline-3-carbonitrile, using 1-chloro-4-(3-fluorophenyl)-6-methoxyisoquinoline-3-carbonitrile in place of 1-chloro-6-methoxy-4-phenylisoquinoline-3-carbonitrile and glycerol formal in place of allyl alcohol, the title compounds were synthesized.

1-(1,3-dioxolan-4-ylmethoxy)-4-(3-fluorophenyl)-6-methoxyisoquinoline-3-carbonitrile HRMS(ES) found: 381.1249; calcd: 381.1245

1-(1,3-dioxan-5-yloxy)-4-(3-fluorophenyl)-6-methoxyisoquinoline-3-carbonitrile

HRMS(ES) found: 381.1245; calcd: 381.1245

EXAMPLE 55

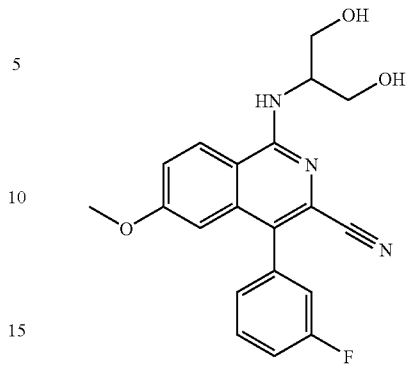

4-(3-fluorophenyl)-1-{[2-hydroxy-1-(hydroxymethyl)ethyl]amino}-6-methoxyisoquinoline-3-carbonitrile A suspension of 1-chloro-4-(3-fluorophenyl)-6-methoxyisoquinoline-3-carbonitrile (50 mg) and [2-hydroxy-1-(hydroxymethyl)ethyl]amine (146 mg) in 2 mL isopropanol was heated at 160 C in a microwave reactor for 8 h. The reaction was concentrated and purified by flash chromatography (0% to 5% MeOH in EtOAc) to give a white solid.

HRMS(ES) found: 368.1395; calcd: 368.1405

EXAMPLE 56

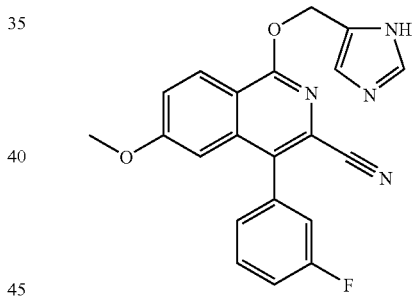

4-(3-fluorophenyl)-1-(1H-imidazol-5-ylmethoxy)-6-methoxyisoquinoline-3-carbonitrile Step A Following the procedure for 1-(allyloxy)-6-methoxy-4-phenylisoquinoline-3-carbonitrile, using 1-chloro-4-(3-fluorophenyl)-6-methoxyisoquinoline-3-carbonitrile in place of 1-chloro-6-methoxy-4-phenylisoquinoline-3-carbonitrile and using (1-trityl-1H-imidazol-5-yl)methanol in place of allyl alcohol, 4-(3-fluorophenyl)-6-methoxy-1-[(1-trityl-1H-imidazol-5-yl)methoxy]isoquinoline-3-carbonitrile was synthesized Step B 4-(3-fluorophenyl)-6-methoxy-1-[(1-trityl-1H-imidazol-5-yl)methoxy]isoquinoline-3-carbonitrile (255 mg) was dissolved in 4 mL of 5% TFA in $CH_2Cl_2$ at 0 C to give a bright yellow solution. The reaction was stirred at 0 C for 2.5 h, then at room temp for 1.5 h. MeOH was added, and the reaction

EXAMPLE 57

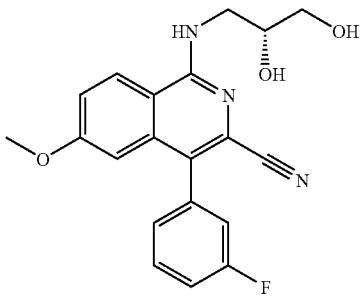

1-{[(2R)-2,3-dihydroxypropyl]amino}-4-(3-fluorophenyl)-6-methoxyisoquinoline-3-carbonitrile Following the procedure for 4-(3-fluorophenyl)-1-[(2-hydroxyethyl)amino]-6-methoxyisoquinoline-3-carbonitrile, using 2(R)-1-amino-2,3-propanediol in place of 2-aminoethanol, the title compound was synthesized.

HRMS(ES) found: 368.1406; calcd: 368.1405

EXAMPLE 58

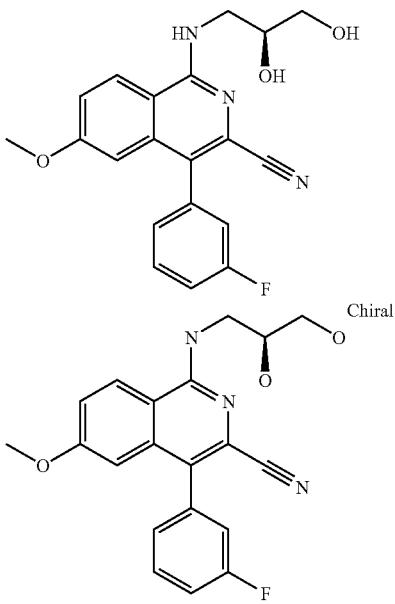

1-{[(2S)-2,3-dihydroxypropyl]amino}-4-(3-fluorophenyl)-6-methoxyisoquinoline-3-carbonitrile Following the procedure for 4-(3-fluorophenyl)-1-[(2-hydroxyethyl)amino]-6-methoxyisoquinoline-3-carbonitrile, using 2(S)-1-amino-2,3-propanediol in place of 2-aminoethanol, the title compound was synthesized.

HRMS(ES) found: 368.1401; calcd: 368.1405

EXAMPLE 59

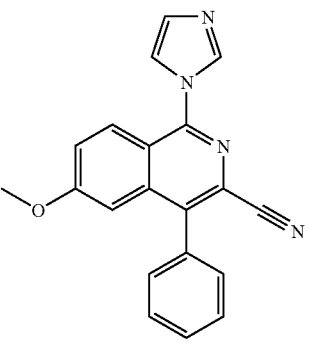

1-(1H-imidazol-1-yl)-6-methoxy-4-phenylisoquinoline-3-carbonitrile

To a solution of imidazole (15 mg) in 2 mL DME was added NaH (12 mg, 60% dispersion in mineral oil); a precipitate formed immediately. The mixture was stirred at room temp for 5 min, then heated to 75 C. A solution of 1-chloro-4-phenyl-6-methoxyisoquinoline-3-carbonitrile (60 mg) in 1 mL DME was added via cannula. Heating continued at 75 C for 45 min. The reaction was cooled to room temp and quenched by adding a few drops of water, then partitioned between saturated aqueous sodium bicarbonate and EtOAc. The organic solution was washed with brine (1×), dried over MgSO$_4$ and concentrated. Flash chromatography (0% to 10% MeOH (10% NH4OH) in EtOAc) gave a white solid.

HMS(ES) found: 327.1250; calcd: 327.1240

EXAMPLE 60

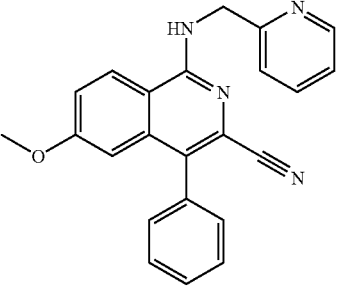

6-methoxy-4-phenyl-1-[(pyridin-2-ylmethyl)amino]isoquinoline-3-carbonitrile

Following the procedure for 1-(allylamino)-6-methoxy-4-phenylisoquinoline-3-carbonitrile, using (pyridin-2-ylmethyl)amine in place of allylamine and heating for 35 min instead of 1 h, the title compound was synthesized.

HRMS(ES) found: 367.1555; calcd: 367.1553

EXAMPLE 61

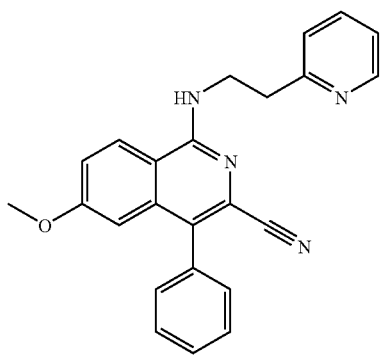

6-methoxy-4-phenyl-1-[(2-pyridin-2-ylethyl)amino]isoquinoline-3-carbonitrile

Following the procedure for 1-(allylamino)-6-methoxy-4-phenylisoquinoline-3-carbonitrile, using (2-pyridin-2-ylethyl)amine in place of allylamine and heating for 35 min instead of 1 h, the title compound was synthesized.

HRMS(ES) found: 381.1711; calcd: 381.1710

EXAMPLE 62

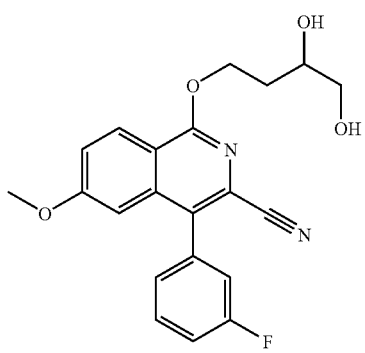

1-[(3,4-dihydroxybutyl)amino]-4-(3-fluorophenyl)-6-methoxyisoquinoline-3-carbonitrile Step A To a suspension of 1-chloro-4-(3-fluorophenyl)-6-methoxyisoquinoline-3-carbonitrile (150 mg) in 15 mL isopropanol was added to 6 mL of a 0.81 M solution of 4-amino-1-butene. The mixture was heated to reflux for 4 days, then cooled to room temp and partitioned between EtOAc and saturated aqueous sodium bicarbonate. The organic solutions were washed with brine (1×), dried over MgSO$_4$, and concentrated. Flash chromatography (3% to 50% EtOAc in hexanes) provided 146 mg of 1-(but-3-enylamino)-4-(3-fluorophenyl)-6-methoxyisoquinoline-3-carbonitrile as a tan solid.

Step B

Following the procedure for 1-(2,3-dihydroxypropoxy)-6-methoxy-4-phenylisoquinoline-3-carbonitrile, using 1-(but-3-enylamino)-4-(3-fluorophenyl)-6-methoxyisoquinoline-3-carbonitrile in place of 1-(allyloxy)-6-methoxy-4-phenylisoquinoline-3-carbonitrile, the title compound was synthesized.

HRMS(ES) found: 382.1556; calcd: 382.1562

EXAMPLE 63

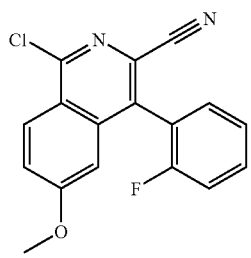

1-chloro-4-(2-fluorophenyl)-6-methoxyisoquinoline-3-carbonitrile

Following the procedure for 1-chloro-6-methoxy-4-phenylisoquinoline-3-carbonitrile, using 6-methoxy-1-oxo-4-(2-fluorophenyl)-1,2-dihydroisoquinoline-3-carbonitrile in place of 6-methoxy-1-oxo-4-phenyl-1,2-dihydroisoquinoline-3-carbonitrile, the title compound was synthesized.

HRMS(ES) calcd: 313.0539; found: 313.0533

EXAMPLE 64

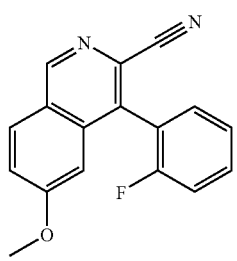

4-(2-fluorophenyl)-6-methoxyisoquinoline-3-carbonitrile

Following the procedure for 4-(3-fluorophenyl)-6-methoxyisoquinoline-3-carbonitrile, using 1-chloro-4-(2-fluorophenyl)-6-methoxyisoquinoline-3-carbonitrile in place 1-chloro-4-(3-fluorophenyl)-6-methoxyisoquinoline-3-carbonitrile, the title compound was synthesized.

HRMS(ES) calcd: 279.0928; found: 279.0923

EXAMPLE 65

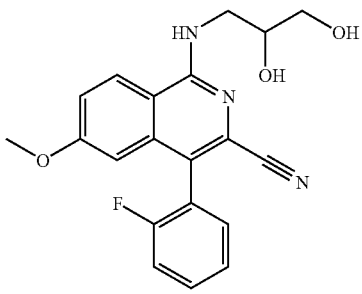

1-[(2,3-dihydroxypropyl)amino]-4-(2-fluorophenyl)-6-methoxyisoquinoline-3-carbonitrile Following the procedure for 4-(3-fluorophenyl)-1-[(2-hydroxyethyl)amino]-6-methoxyisoquinoline-3-carbonitrile, using 1-chloro-4-(2-fluorophenyl)-6-methoxyisoquinoline-3-carbonitrile in place of 1-chloro-4-(3-fluorophenyl)-6-methoxyisoquinoline-3-carbonitrile, and using racemic 1-amino-2,3-propanediol in place of 2-aminoethanol, the title compound was synthesized.

HRMS(ES) calcd: 368.1405; found: 368.1398

EXAMPLE 66

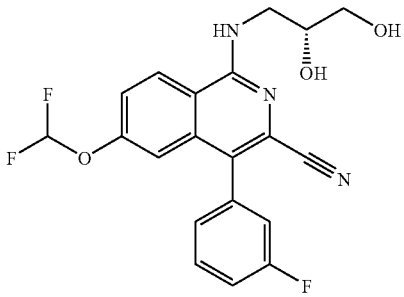

6-(difluoromethoxy)-1-{[(2S)-2,3-dihydroxypropyl]amino}-4-(3-fluorophenyl)isoquinoline-3-carbonitrile Step A To a solution of 2-allyl-4-(3-fluorophenyl)-6-methoxy-1-oxo-1,2-dihydroisoquinoline-3-carbonitrile (2.0 g) in 24 mL DMSO was added NaCN (1.47 g). The reaction was heated to 150 C for 6.5 h, then diluted with 1N NaOH and extracted with EtOAc (2×). The organic solutions were extracted once with 1N NaOH. The combine aqueous solutions were acidified with conc. HCl and extracted with EtOAc (3×). All organic solutions were combined and dried (MgSO$_4$), then concentrated to give a dark solid. The solid was suspended in CH$_2$Cl$_2$ and filtered to give 1.04 g of 2-allyl-4-3-fluorophenyl)-6-hydroxy-1-oxo-1,2-dihydroisoquinoline-3-carbonitrile, which was used without further purification.

To a solution of 2-allyl-4-(3-fluorophenyl)-6-hydroxy-1-oxo-1,2-dihydroisoquinoline-3-carbonitrile (1.04 g) in 7 mL DMF were added potassium carbonate (0.96 g) and methyl-1-1-difluoro-1-chloro-acetate (0.96 g). The reaction was heated to 80 C for 3 h, then diluted with EtOAc washed with 1 N NaOH (2×). The combined organic solutions were dried (MgSO4) and concentrated. Flash chromatography (2-40% EtOAc/hexanes, 40 g silica) provided 386 mg of 2-allyl-6-(difluoromethoxy)-4-(3-fluorophenyl)-1-oxo-1,2-dihydroisoquinoline-3-carbonitrile. The material was approximately 80% pure and was used without further purification.

Step C

To a solution of 2-allyl-6-(difluoromethoxy)-4-(3-fluorophenyl)-1-oxo-1,2-dihydroisoquinoline-3-carbonitrile in 10 mL dioxane were added triethylamine (0.363 mL) and formic acid (0.079 mL). The solution was sparged with argon for 10 min, then Pd(PPh$_3$)$_4$ was added, and the reaction was heated to 100 C for 2 h. The reaction was concentrated to dryness, then partitioned between CH$_2$Cl$_2$ and and 50% brine. The organic solution was dried (MgSO4) and concentrated to dry solid. Flash chromatography (5-45% EA/hex, 1% MeOH, 40 g silica) provided 110 mg of 6-(difluoromethoxy)-4-(3-fluorophenyl)-1-oxo-1,2-dihydroisoquinoline-3-carbonitrile. The material was approximately 80% pure and was used without further purification.

Step D

Following the procedure for 1-chloro-6-methoxy-4-phenylisoquinoline-3-carbonitrile, using 6-(difluoromethoxy)-4-(3-fluorophenyl)-1-oxo-1,2-dihydroisoquinoline-3-carbonitrile in place of 6-(methoxy)-4-(3-fluorophenyl)-1-oxo-1,2-dihydroisoquinoline-3-carbonitrile, 1-chloro-6-(difluoromethoxy)-4-(3-fluorophenyl)isoquinoline-3-carbonitrile was synthesized.

Step E

Following the procedure for 4-(3-fluorophenyl)-1-[(2-hydroxyethyl)amino]-6-methoxyisoquinoline-3-carbonitrile, using 1-chloro-6-(difluoromethoxy)-4-3-fluorophenyl)isoquinoline-3-carbonitrile in place 1-chloro-4-(3-fluorophenyl)-6-methoxyisoquinoline-3-carbonitrile, and using 2S-1-amino-2,3-propanediol in place of 2-aminoethanol, the title compound was synthesized.

HRMS(ES) calcd: 404.1217; found: 404.1223

EXAMPLE 67

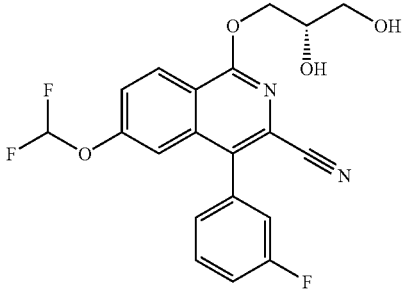

6-(difluoromethoxy)-1-{[(2S)-2,3-dihydroxypropyl]oxy}-4-(3-fluorophenyl)isoquinoline-3-carbonitrile Step A Following the procedure for 1-(allyloxy)-6-methoxy-4-phenylisoquinoline-3-carbonitrile, using (R)-(−)-2,2,-dimethyl-1,3-dioxolane-4-methanol in place of allyl alcohol, and using 1-chloro-6-(difluoromethoxy)-4-(3-fluorophenyl)isoquinoline-3-carbonitrile in place 1-chloro-4-phenyl-6-methoxyisoquinoline-3-carbonitrile, 1-{[(4R)-2,2-dimethyl-1,3-dioxolan-4-yl]methoxy}-6-(difluoromethoxy)-4-(3-fluorophenyl)isoquinoline-3-carbonitrile was synthesized.

Step B

Following the procedure for 1-{[(2R)-2,3-dihydroxypropyl]oxy}-6-methoxy-4-phenylisoquinoline-3-carbonitrile, using 1-{[(4R)-2,2-dimethyl-1,3-dioxolan-4-yl]methoxy}-6-(difluoromethoxy)-4-(3-fluorophenyl)isoquinoline-3-carbonitrile in place of 1-{[(4S)-2,2-dimethyl-1,3-dioxolan-4-yl]methoxy}-6-methoxy-4-phenylisoquinoline-3-carbonitrile, the title compound was synthesized.

HRMS(ES) calcd: 405.1057; found: 405.1061

EXAMPLE 68

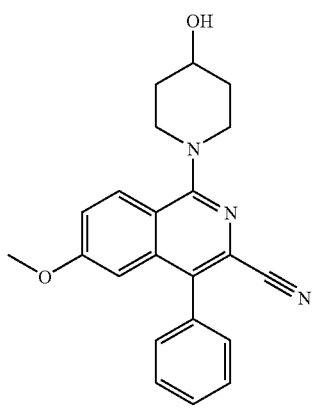

1-(4-hydroxypiperidin-1-yl)-6-methoxy-4-phenylisoquinoline-3-carbonitrile

Following the procedure for 1-(allylamino)-6-methoxy-4-phenylisoquinoline-3-carbonitrile, using 4-hydroxypiperidine in place of allylamine, the title compound was synthesized.

HRMS(ES) calcd: 360.1707; found: 360.1704

EXAMPLE 69

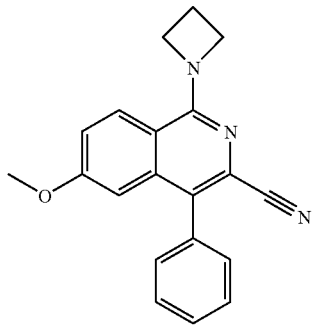

1-azetidin-1-yl-6-methoxy-4-phenylisoquinoline-3-carbonitrile

Following the procedure for 1-(allylamino)-6-methoxy-4-phenylisoquinoline-3-carbonitrile, using azetidine in place of allylamine, the title compound was synthesized.

HRMS(ES) calcd: 316.1445; found: 316.1448

EXAMPLE 70

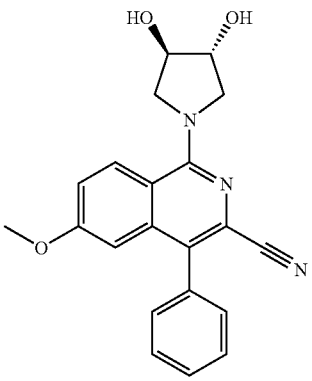

1-[(3R,4R)-3,4-dihydroxypyrrolidin-1-yl]-6-methoxy-4-phenylisoquinoline-3-carbonitrile Following the procedure for 1-(allylamino)-6-methoxy-4-phenylisoquinoline-3-carbonitrile, using (3R,4R)-3,4-dihydroxypyrrolidine in place of allylamine, the title compound was synthesized.

HRMS(ES) calcd: 362.1499; found: 362.1506

EXAMPLE 71

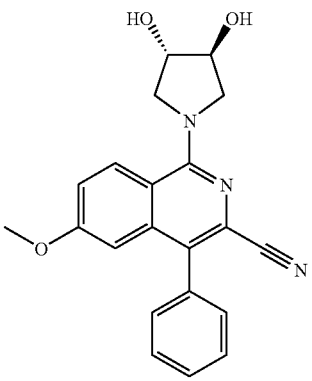

1-[(3S,4S)-3,4-dihydroxypyrrolidin-1-yl]-6-methoxy-4-phenylisoquinoline-3-carbonitrile Following the procedure for 1-(allylamino)-6-methoxy-4-phenylisoquinoline-3-carbonitrile, using (3S,4S)-3,4-dihydroxypyrrolidine in place of allylamine, the title compound was synthesized.

HRMS(ES) calcd: 362. 1499; found: 362.1511

EXAMPLE 72

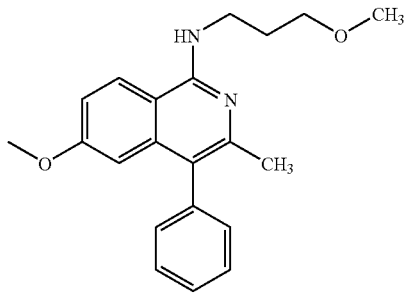

6-methoxy-N-(3-methoxypropyl)-3-methyl-4-phenylisoquinolin-1-amine

Following the procedure for 2-[(6-methoxy-3-methyl-4-phenylisoquinolin-1-yl)amino]ethanol, using (in Step B) 3-methoxy-1-aminopropane in place of ethanolamine, the titled compound was synthesized.

Elemental analysis calcd for $C_{21}H_{24}N_2O_2$: C, 74.97; H, 7.19; N, 8.33. Found: C, 74.77; H, 7.51; N, 8.42.

Using the methodologies described below, representative compounds of the invention were evaluated and found to exhibit activity in the Kv1.5 assays, thereby demonstrating and confirming the utility of the compounds of this invention as Kv1.5 inhibitors and antiarrhythmics. Compounds of this type may exhibit forward rate-dependence, blocking the outward $K^+$ currents to a greater extent or preferentially at faster rates of depolarization or heart rates. Such a compound could be identified in electrophysiological studies as described below. For example, during a train of depolarizations delivered at frequencies of 1 Hz and 3 Hz, the block is "rate-dependent" if the amount of block observed during a 10 second train at 3 Hz is greater than that at 1 Hz. A Kv1.5 blocker may also display use-dependence, during which the block of the outward $K^+$ currents increases with use, or during repetitive depolarization of a cardiac cell. Use dependence of block occurs to a greater extent with each successive depolarization in a train or sequence of pulses or depolarizations at a given rate or frequency. For example, during a train of 10 depolarizations at a frequency of 1 Hz, the block is "use-dependent" if the amount of block is greater for the $10^{th}$ pulse than for the $1^{st}$ pulse of the train. A Kv1.5 blocker may exhibit both use-dependence and rate-dependence.

A Kv1.5 blocker may also be identified through electrophysiological studies of native $I_{Kur}$ using cardiac myocytes or other tissue from various species including, but not limited to, human, rat, mouse, dog, monkey, ferret, rabbit, guinea pig, or goat. In native tissues Kv1.5 may exist as a homo-oligomer, or as a hetero-oligomer with other Kv family members, or may exist in a complex with a β-subunit. Compounds of this invention may block Kv1.5 homo- or hetero-oligomers or Kv1.5 in complexes with β-subunits.

EXAMPLE 73

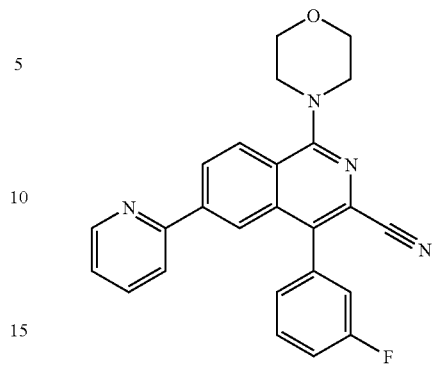

4-(3-fluorophenyl)-1-morpholin-4-yl-6-pyridin-2-ylisoquinoline-3-carbonitrile

Step A: 2-Allyl-4(3-fluorophenyl)-6-hydroxy-1-oxo-1,2-dihydroisoquinoline-3-carbonitrile Sodium cyanide (3.3 g, 67.2 mmol) was added to a suspension of 2-Allyl-4-(3-fluorophenyl)-6-methoxy-1-oxo-1,2-dihydroisoquinoline-3-carbonitrile (7.5 g, 22.4 mmol) in DMSO (100 mL). The reaction mixture was heated to 150° C. for 18 h. The reaction was cooled to room temperature and diluted with ice water (100 mL). This was acidified to a pH of 5 with 6M HCl. The brown precipitate was filtered and washed with ether to yield the title compound as a brown solid.

Step B: 2-Allyl-3-cyano-4-(3-fluorophenyl)-1-oxo-1,2-dihydroisoquinolin-6-yl trifluoromethansulfonate Diisopropylethylamine (6.3 mL, 36.2 mmol) was added to a solution of 2-Allyl-4-(3-fluorophenyl)-6-hydroxy-1-oxo-1,2-dihydroisoquinoline-3-carbonitrile (5.7 g, 17.8 mmol) in anhydrous DCM (100 mL) under Nitrogen. The reaction mixture was chilled to −78° C. with a dry ice/IPA bath. Triflic anhydride (6.1 mL, 36.2 mmol) was added and the resulting brown solution was stirred for 1 h at −78° C. The reaction was warmed to room temperature and diluted with DCM (100 mL). This was washed with sat'd $NaHCO_3$, dried ($MgSO_4$), filtered and concentrated. The residue was purified by flash chromatography (1:4 EtOAc/hexanes) to afford the title compound as beige crystals.

Step C: 2-allyl-4-(3-fluorophenyl)-1-oxo-6-(4,4,5,5-tetramethyl-1,3,2-dioxaborolan-2-yl)-1,2-dihydroisoquinoline-3-carbonitrile Bis(pinacolato)diboron (1.2 g, 4.9 mmol), $PdCl_2$(dppf) (181 mg, 0.22 mmol), dppf (123 mg, 0.22 mmol), KOAc (1.3 g, 13.3 mmol) were added to a solution of 2-Allyl-3-cyano4-(3-fluorophenyl)-1-oxo-1,2-dihydroisoquinolin-6-yl trifluoromethanesulfonate (2.0 g, 4.4 mmol) in anhydrous dioxane (24 mL) under Nitrogen in a high pressure tube. The tube was sealed and the reaction heated to 80° C. for 2 h. The reaction was cooled to room temperature, diluted with EtOAc, and filtered through Celite. The filtrate was washed with $H_2O$, dried (MgSO₄), filtered and concentrated. The black residue was purified by flash chromatography (1:2 EtOAc/hexanes) to yield the title compound as a white solid.

Step D: 2-allyl-4-(3-fluorophenyl)-1-oxo-6-pyridin-2-yl-1,2-dihydroisoquinoline-3-carbonitrile and 4-(3-fluorophenyl)-1-hydroxy-6-pyridin-2-ylisoquinoline-3-carbonitrile 2-Bromopyridine (158 mg, 1.0 mmol), Pd$_2$(dba)$_3$ (92 mg, 0.10 mmol), Cy$_3$P (56 mg, 0.20 mmol), Cs$_2$CO$_3$ (348 mg, 1.1 mmol) were added to a solution of 2-allyl-4-(3-fluorophenyl)-1-oxo-6-(4,4,5,5-tetramethyl-1,3,2-dioxaborolan-2-yl)-1,2-dihydroisoquinoline-3-carbonitrile (430 mg, 1.0 mmol) in anhydrous dioxane (2 mL) under Argon in a high pressure tube. The tube was sealed and the reaction heated to 120° C. for 18 h. The reaction was cooled to room temperature, diluted with EtOAc, and filtered through a Celite. The EtOAc was washed with H$_2$O, brine, dried (MgSO$_4$), filtered and concentrated. The green residue was purified by flash chromatography (1:2-1:1 EtOAc/hexanes) to yield the first title compound as an off-white solid and the second title compound as a yellow solid.

Step E: 1-chloro-4-(3-fluorophenyl)-6-pyridin-2-ylisoquinoline-3-carbonitrile POCl$_3$ (22 mg, 0.15 mmol) was added to 4-(3-fluorophenyl)-1-hydroxy-6-pyridin-2-ylisoquinoline-3-carbonitrile (50 mg, 0.15 mmol) neat. The resulting mixture was heated to 90° C. for 18 h. The reaction was cooled to room temperature and diluted with H$_2$O (10 mL). This was brought to a pH of 9 with NaHCO$_3$. The aqueous layer was extracted with EtOAc. The organic layer was washed with brine, dried (MgSO$_4$), filtered and concentrated to yield the title compound as a brown oil.

Step F: 4-(3-fluorophenyl)-1-morpholin-4-yl-6-pyridin-2-ylisoquinoline-3-carbonitrile Morpholine (36 mg, 0.42 mmol) was added to a solution of 1-chloro-4-(3-fluorophenyl)-6-pyridin-2-ylisoquinoline-3-carbonitrile (15 mg, 0.04 mmol) in n-BuOH (1.0 mL) in a microwave tube. The tube was sealed and heated to 220° C. for 1 h in the microwave. The reaction was diluted with CHCl$_3$ and washed with sat'd NaHCO$_3$, brine, dried (MgSO$_4$), filtered and concentrated. The residue was purified via flash chromatography (1:3-1:1 EtOAc/hexanes) to yield the title compound as a beige solid.

$^1$H NMR (CDCl$_3$) δ 8.71 (s, 1H), 8.35-8.38 (m, 1H), 8.24-8.26 (m, 1H), 8.14 (s, 1H), 7.76-7.80 (m, 1H), 7.67 (m, 1H), 7.52-7.59 (m, 1H), 7.19-7.31 (m, 4H), 3.99-4.01 (m, 4H), 3.56-3.58 (m, 4H); MS (M+H)$^+$=411.2

Examples 73-1 to 73-3 in the following table were prepared using the procedures detailed above. Unless completely shown, compounds have the following general structure with variable XX defined in the table.

| Example | Compound | Name | MS (M + H)$^+$ |
|---|---|---|---|
| 73-1 | XX is 4-methylimidazol-1-yl | 4-(3-fluorophenyl)-1-(4-methyl-1H-Imidazol-1-yl)-6-pyridin-2-ylisoquinoline-3-carbonitrile | 406.1457 |
| 73-2 | XX is 3-hydroxypyrrolidin-1-yl | (+/−)-4-(3-fluorophenyl)-1-(3-hydroxypyrrolidin-1-yl)-6-pyridin-2-ylisoquinoline-3-carbonitrile | 411.1627 |
| 73-3 | XX is (pyridin-2-ylmethyl)amino | 4-(3-fluorophenyl)-6-pyridin-2-yl-1-[(pyridin-2-ylmethyl)amino]-isoquinoline-3-carbonitrile | 432.1656 |

EXAMPLE 74

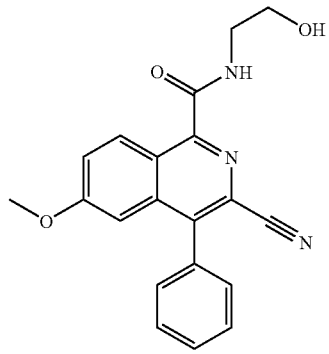

3-cyano-N-(2-hydroxyethyl)-6-methoxy-4-phenylisoquinoline-1-carboxamide

Step A 6-methoxy-4-phenylisoquinoline-1,3-dicarbonitrile. 1-chloro-6-methoxy-4-phenylisoquinoline-3-carbonitrile (3.393 mmol), Pd$_2$(dba)$_3$ (0.068 mmol), dppf (0.136 mmol), Zn(CN)$_2$ (6.786 mmol) and zinc powder(0.407 mmol) were combined in a r.b. flask, and the flask was purged with argon. 10 mL DMA was added, and the reaction was heated at 120° C. under a stream of Ar for 4.5 h, then cooled to rt and diluted with 100 mL EtOAc. The organic layer was washed with 2(N) aq NH₄OH (50 mL×1) and brine (1×), dried over Na₂SO₄ and concentrated to give a yellow solid which was purified by flash chromatography to provide a white solid (0.97 g).

Step B 3-cyano-6-methoxy-4-phenylisoquinoline-1-carboxylic acid. To a suspension of 6-methoxy-4-phenylisoquinoline-1,3-dicarbonitrile in 25 mL EtOH was added 2(N) aq NaOH (15 mL), and the reaction was stirred at 40° C. for 2 h. Then concentrated aq HCl (18 mL) and water (29 mL) were added to the reaction mixture and heated at 100° C. for 16 h. After cooling to rt, it was extracted with DCM (4×). The combined organic layers were dried over Na₂SO₄ and concentrated to a tan solid (470 mg, 85%). This crude product was used without further purification.

Step C 3-cyano-N-(2-hydroxyethyl)-6-methoxy-4-phenylisoquinoline-1-carboxamide. DMF was added to a vial containing 3-cyano-6-methoxy-4-phenylisoquinoline-1-carboxylic acid (0.072 g, 0.237 mmol), EDC (0.068 g, 0.355 mmol) and HOAt (0.048 g, 0.355 mmol). Ethanolamine (0.029 g, 0.473 mmol) and DIEA (0.153 g, 1.183 mmol) were added to this mixture, and the reaction stirred at rt overnight. The reaction mixture was filtered and purified by r.p. HPLC. White solid (0.038 g, 46%).

$^1$H NMR (500 MHz, CDCl₃): δ 9.68 (d, J=9.5 Hz, 1H), 8.51 (br, 1H), 7.63-7.58 (m, 3H), 7.49-7.43 (m, 3H1), 3.93 (t, J=4.4 Hz, 2H), 3.78 (s, 3H), 3.75-3.72 (m, 2H).

Examples 74-1 to 74-53 in the following table were prepared using the procedures detailed above. Unless completely shown, compounds have the following general structure with variable XX defined in the table.

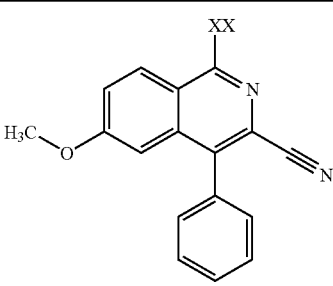

| | | | |
|---|---|---|---|
| 74-1 | XX is 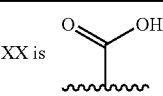 | 305.0927 | 3-cyano-6-methoxy-4-phenylisoquinoline-1-carboxylic acid |
| 74-2 | XX is 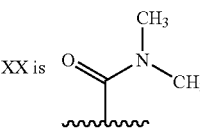 | 332.1409 | 3-cyano-6-methoxy-N,N-dimethyl-4-phenylisoquinoline-1-carboxamide |
| 74-3 | XX is 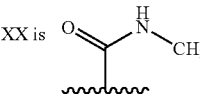 | 318.1257 | 3-cyano-6-methoxy-N-methyl-4-phenylisoquinoline-1-carboxamide |
| 74-4 | XX is 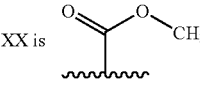 | 319.1088 | methyl 3-cyano-6-methoxy-4-phenylisoquinoline-1-carboxylate |
| 74-5 | XX is 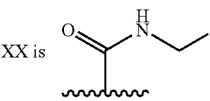 | 332.1399 | 3-cyano-N-ethyl-6-methoxy-4-phenylisoquinoline-1-carboxamide |
| 74-6 | XX is 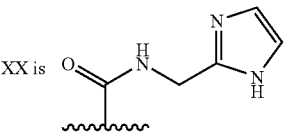 | 384.1446 | 3-cyano-N-(1H-imidazol-2-methoxy-4-phenylisoquinoline-1- |
| 74-7 | XX is 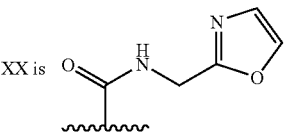 | 385.1284 | 3-cyano-6-methoxy-N-(1,3-oxazol-2-ylmethyl)-4-phenylisoquinoline-1-carboxamide |

-continued

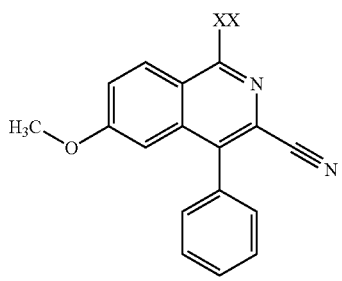

| | XX is | | |
|---|---|---|---|
| 74-8 | ![structure: C(=O)NHCH2C(=O)OCH3] | 399.1452 | 3-cyano-N-(1-isoxazol-5-ylethyl)-6-methoxy-4-phenylisoquinoline-1-carboxamide |
| 74-9 | ![structure: C(=O)NH-tetrahydrofuran-3-yl] | 374.1493 | 3-cyano-6-methoxy-4-phenyl-N-tetrahydrofuran-3-ylisoquinoline-1-carboxamide |
| 74-10 | ![structure: C(=O)NHCH2CH2CH3] | 346.1546 | 3-cyano-6-methoxy-4-phenyl-N-propylisoquinoline-1-carboxamide |
| 74-11 | ![structure: C(=O)NHCH(CH3)2] | 346.1558 | 3-cyano-N-isopropyl-6-methoxy-4-phenylisoquinoline-1-carboxamide |
| 74-12 | ![structure: C(=O)NHCH2-pyridin-2-yl] | 395.1505 | 3-cyano-6-methoxy-4-phenyl-N-(pyridine-2-ylmethyl)isoquinoline-1-carboxamide |
| 74-13 | ![structure: C(=O)NHCH2CH(OH)CH2OH] | 378.1436 | 3-cyano-N-(2,3-dihydroxypropyl)-6-methoxy-4-phenylisoquinoline-1-carboxamide |
| 74-14 | ![structure: C(=O)NH-(2-oxotetrahydrofuran-3-yl)] | 388.1314 | 3-cyano-6-methoxy-N-(2-oxotetrahydrofuran-3-yl)-4-phenylisoquinoline-1-carboxamide |
| 74-15 | ![structure: C(=O)NHCH2C(=O)OCH3] | 376.1267 | methyl N-[(3-cyano-6-methoxy-4-phenylisoquinolin-1-yl)carbonyl]glycinate |
| 74-16 | ![structure: C(=O)NHCH2CH2OCH2CH3] | 376.1636 | 3-cyano-N-(2-ethoxyethyl)-6-methoxy-4-phenylisoquinoline-1-carboxamide |

-continued

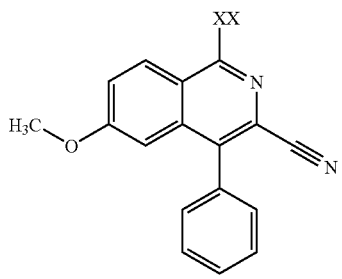

| | | | |
|---|---|---|---|
| 74-17 | XX is 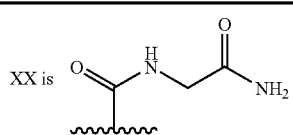 | 361.1274 | N-[(3-cyano-6-methoxy-4-phenylisoquinolin-1-yl)carbonyl]glycinamide |
| 74-18 | XX is 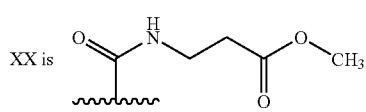 | 390.1422 | methyl N-[(3-cyano-6-methoxy-4-phenylisoquinolin-1-yl)carbonyl]-beta-alaninate |
| 74-19 | XX is 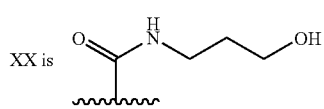 | 362.1478 | 3-cyano-N-(3-hydroxypropyl)-6-methoxy-4-phenylisoquinoline-1-carboxamide |
| 74-20 | XX is 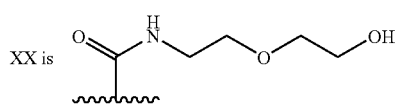 | 392.1587 | 3-cyano-N-[2-(2-hydroxyethoxy)ethyl]-6-methoxy-4-phenylisoquinoline-1-carboxamide |
| 74-21 | XX is 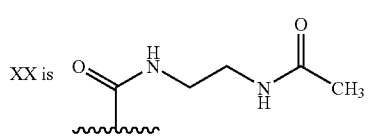 | 389.1617 | N-[2-(acetylamino)ethyl]-3-cyano-6-methoxy-4-phenylisoquinoline-1-carboxamide |
| 74-22 | XX is 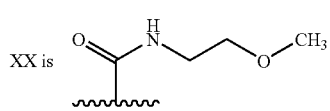 | 362.1509 | 3-cyano-6-methoxy-N-(2-methoxyethyl)-4-phenylisoquinoline-1-carboxamide |
| 74-23 | XX is 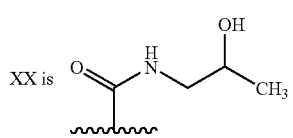 | 362.1515 | 3-cyano-N-(2-hydroxypropyl)-6-methoxy-4-phenylisoquinoline-1-carboxamide |
| 74-24 | XX is 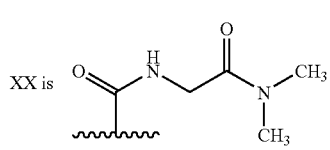 | 389.1621 | N-[(3-cyano-6-methoxy-4-phenylisoquinolin-1-yl)carbonyl]glycin(dimethyl)amide |
| 74-25 | XX is 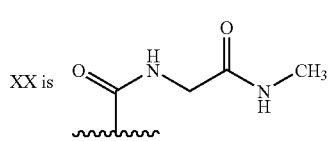 | 375.1468 | N-[(3-cyano-6-methoxy-4-phenylisoquinolin-1-yl)carbonyl]glycin(methyl)amide |
| 74-26 | XX is 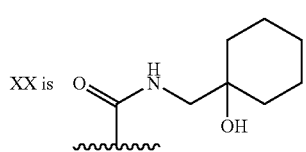 | 416.1986 | 3-cyano-N-[(1-hydroxycyclohexyl)methyl]-6-methoxy-4-phenylisoquinoline-1-carboxamide |

-continued

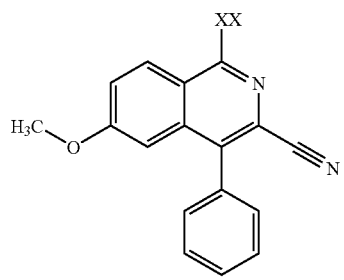

| | | | |
|---|---|---|---|
| 74-27 | XX is 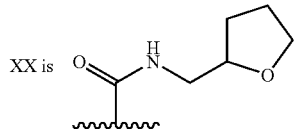 | 388.1667 | 3-cyano-6-methoxy-4-phenyl-N-(tetrahydrofuran-2-ylmethyl)isoquinoline-1-carboxamide |
| 74-28 | XX is 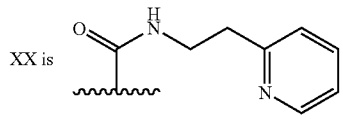 | 409.1668 | 3-cyano-6-methoxy-4-phenyl-N-(2-pyridin-2-ylethyl)isoquinoline-1-carboxamide |
| 74-29 | XX is 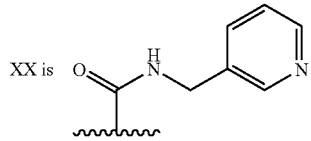 | 395.1520 | 3-cyano-6-methoxy-4-phenyl-N-(pyridin-3-ylmethyl)isoquinoline-1-carboxamide |
| 74-30 | XX is 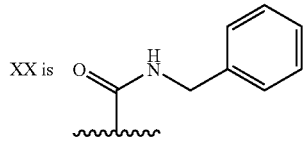 | 394.1658 | N-benzyl-3-cyano-6-methoxy-4-phenylisoquinoline-1-carboxamide |
| 74-31 | XX is 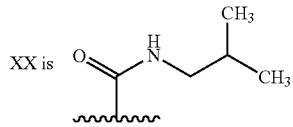 | 360.1722 | 3-cyano-N-isobutyl-6-methoxy-4-phenylisoquinoline-1-carboxamide |
| 74-32 | XX is 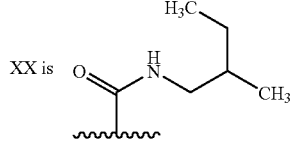 | 374.1883 | 3-cyano-6-methoxy-N-(2-methylbutyl)-4-phenylisoquinoline-1-carboxamide |
| 74-33 | XX is 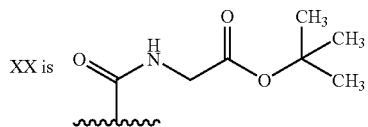 | 418.1761 | tert-butyl N-[(3-cyano-6-methoxy-4-phenylisoquinolin-1-yl)carbonyl]glycinate |
| 74-34 | XX is 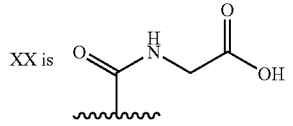 | 362.1137 | N-[(3-cyano-6-methoxy-4-phenylisoquinolin-1-yl)carbonyl]glycine |
| 74-35 | XX is 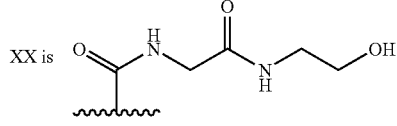 | 405.1554 | N-[(3-cyano-6-methoxy-4-phenylisoquinolin-1-yl)carbonyl]glycin-hydroxyethyl)amide |

-continued

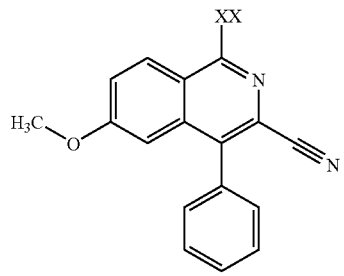

| | | | |
|---|---|---|---|
| 74-36 | XX is 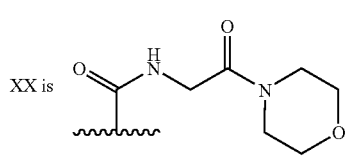 | 431.1714 | N-[(3-cyano-6-methoxy-4-phenylisoquinolin-1-yl)carbonyl]glycin-morpholine)amide |
| 74-37 | XX is 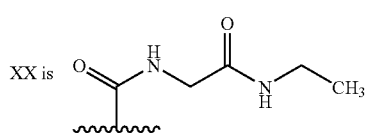 | 389.1613 | N-[(3-cyano-6-methoxy-4-phenylisoquinolin-1-yl)carbonyl]glycin(ethyl)amide |
| 74-38 | XX is 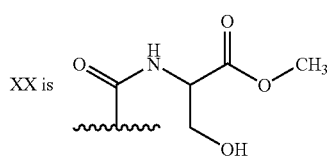 | 406.1396 | N-[(3-cyano-6-methoxy-4-phenylisoquinolin-1-yl)carbonyl]serine, methyl ester |
| 74-39 | XX is 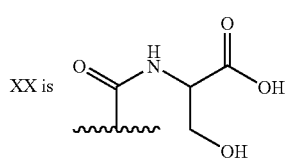 | 392.08 | N-[(3-cyano-6-methoxy-4-phenylisoquinolin-1-yl)carbonyl]serine |
| 74-40 | XX is 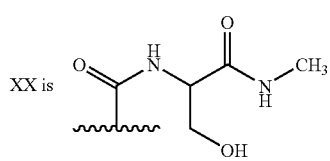 | 405.1552 | N-[(3-cyano-6-methoxy-4-phenylisoquinolin-1-yl)carbonyl]serin(methyl)amide |
| 74-41 | XX is 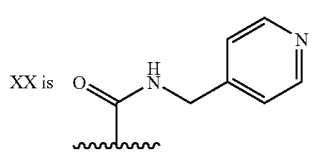 | 395.1490 | 3-cyano-6-methoxy-4-phenyl-N-(pyridin-4-ylmethyl)isoquinoline-1-carboxamide |
| 74-42 | XX is 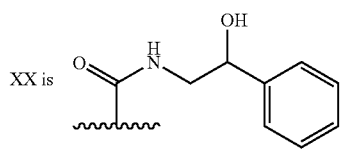 | 424.1632 | 3-cyano-N-(2-hydroxy-2-phenylethyl)-6-methoxy-4-phenylisoquinoline-1-carboxamide |
| 74-43 | XX is 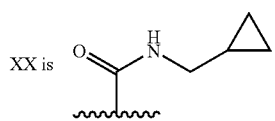 | 358.1540 | 3-cyano-N-(cyclopropylmethyl)-6-methoxy-4-phenylisoquinoline-1-carboxamide |

-continued

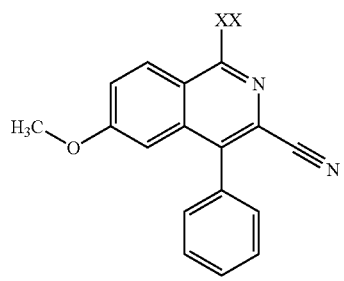

| | XX is | | Name |
|---|---|---|---|
| 74-44 | (1S,2R)-2-(aminocarbonyl)cyclopentyl amide group | 415.1759 | N-[(1S,2R)-2-(aminocarbonyl)cyclopentyl]-3-cyano-6-methoxy-4-phenylisoquinoline-1-carboxamide |
| 74-45 | (1S,2R,5R)-2-hydroxy-5-methylcyclopentyl amide group | 402.1799 | 3-cyano-N-[(1S,2R,5R)-2-hydroxy-5-methylcyclopentyl]-6-methoxy-4-phenylisoquinoline-1-carboxamide |
| 74-46 | (1S,2S)-2-hydroxycyclopentyl amide group | 388.1644 | 3-cyano-N-[(1S,2S)-2-hydroxycyclopentyl]-6-methoxy-4-phenylisoquinoline-1-carboxamide |
| 74-47 | (1S,2R,3S,4S)-2,3-dihydroxy-4-(hydroxymethyl)cyclopentyl amide group | 434.1693 | 3-cyano-N-[(1S,2R,3S,4S)-2,3-dihydroxy-4-(hydroxymethyl)cyclopentyl]-6-methoxy-4-phenylisoquinoline-1-carboxamide |
| 74-48 | 2-morpholin-4-ylethyl amide group | 417.1914 | 3-cyano-6-methoxy-N-(2-morpholin-4-ylethyl)-4-phenylisoquinoline-1-carboxamide |
| 74-49 | (3S,4S)-4-hydroxy-1,1-dioxidotetrahydrothien-3-yl amide group | 438.1104 | 3-cyano-N-[(3S,4S)-4-hydroxy-1,1-dioxidotetrahydrothien-3-yl]-6-methoxy-4-phenylisoquinoline-1-carboxamide |
| 74-50 | ethyl hydrogen sulfate amide group | 428.0917 | 2-{[(3-cyano-6-methoxy-4-phenylisoquinolin-1-yl)carbonyl]amino}ethyl hydrogen sulfate |
| 74-51 | (3S)-4-hydroxy-1,1-dioxidotetrahydrothien-3-yl amide group | 438.1113 | 3-cyano-N-[(3S)-4-hydroxy-1,1-dioxidotetrahydrothien-3-yl]-6-methoxy-4-phenylisoquinoline-1-carboxamide |

-continued

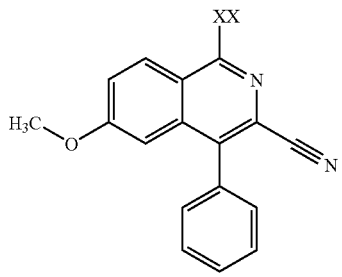

| 74-52 | XX is 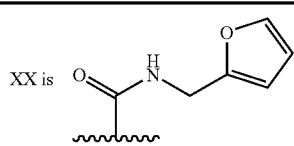 | 384.1332 | 3-cyano-N-(2-furylmethyl)-6-methoxy-4-phenylisoquinoline-1-carboxamide |
| --- | --- | --- | --- |
| 74-53 | 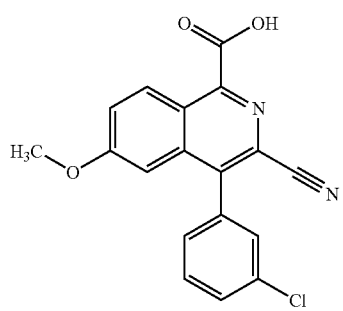 | 339.0526 | 4-(3-chlorophenyl)-3-cyano-6-methoxyisoquinoline-1-carboxylic acid |

EXAMPLE 75

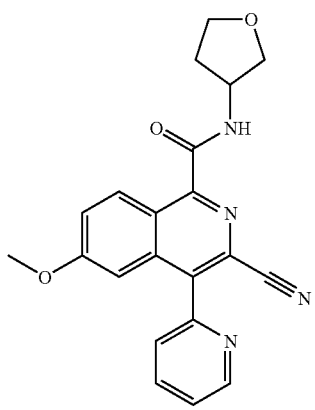

(+/−)-3-cyano-6-methoxy-4-pyridin-2-yl-N-(tetrahydrofuran-3-yl)isoquinoline-1-carboxamide Step A 3-cyano-6-methoxy-4-pyridin-2-yl-1,2-dihydroisoquinolin-1-trifluoromethanesulfonate. A solution of 6-methoxy-1-oxo-4-pyridin-2-yl-1,2-dihydroisoquinoline-3-carbonitrile (0.77 g, 2.777 mmol) in 20 mL dry pyridine was cooled to −10° C. and triflic anhydride was added to it in one portion. The cooling bath was removed, and the reaction was stirred at rt for 1 h. The reaction mixture was diluted with water and the aqueous layer was extracted with DCM (3×). Combined organic layers were dried over $Na_2SO_4$ and concentrated. Purified by flash chromatography: 10% to 80% EtOAc in hexanes. White solid (0.915 g, 80%).

Step B Methyl 3-cyano-6-methoxy-4-pyridin-2-ylisoquinoline-1-carboxylate. 3-cyano-6-methoxy-4-pyridin-2-yl-1,2-dihydroisoquinolin-1-yl trifluoromethanesulfonate (0.267 g, 0.652 mmol), DMF (3.5 mL), MeOH (1.75 mL) and H2O (0.012 mL, 0.652 mmol) were combined in a r.b. flask and bubbled CO through this mixture for 3 min. Triethylamine (0.132 g, 1.305 mmol), dppf (0.072 g, 0.13 mmol) and $Pd(OAc)_2$ (0.015 g, 0.065 mmol) were added to the above mixture and CO was bubbled for 1 min. Stirred under atmospheric CO at 70° C. for 2 h. Cooled to rt. Partitioned between EtOAc and water. The aqueous layer was extracted with EtOAc (2×). Combined organic layers were dried over $Na_2SO_4$ and concentrated. Purified by flash chromatography: 5% to 70% EA in hexanes. Tan solid (0.067 g, 32%).

Step C 3-cyano-6-methoxy-4-pyridin-2-ylisoquinoline-1-carboxylic acid. To a suspension of methyl 3-cyano-6-methoxy-4-pyridin-2-ylisoquinoline-1-carboxylate (0.04 g, 0.125 mmol) in 3 mL EtOH, was added 0.251 mL 1(N) aqueous NaOH and 1.16 mL water. The reaction was stirred at 0° C. for 4 h and then 1(N) aqueous HCl (0.251 mL) was added. The reaction was warmed up to rt and concentrated to a tan solid (used without further purification).

Step D (+/−)-3-cyano-6-methoxy-4-pyridin-2-yl-N-(tetrahydrofuran-3-yl)isoquinoline-1-carboxamide DMF was added to a vial containing 3-cyano-6-methoxy-4-pyridin-2-ylisoquinoline-1-carboxylic acid (0.028 g, 0.092 mmol), tetrahydrofuran-3-aminium chloride (0.068 g, 0.550 mmol), EDC (0.105 g, 0.550 mmol) and HOAT (0.0437 g, 0.275 mmol). DIEA (0.071 g, 0.550 mmol) was added to this mixture and stirred at rt overnight. Partitioned between half-saturated bicarb and EtOAc. The aqueous layer was extracted with EtOAc (3×). The combined organic layers were dried over Na$_2$SO$_4$ and concentrated, then purified by reverse phase HPLC to give a tan solid (0.019 g, 55%).

$^1$H NMR (500 MHz, CDCl$_3$): δ 9.70 (d, J=9.5 Hz, 1H), 8.92-8.90 (m, 1H), 8.28 (d, J=7.3 Hz, 1H), 8.01-7.93 (m, 1H), 7.67 (d, J=7.3 Hz, 1H), 7.55-7.52 (m, 1H), 7.46 (dd, J=9.5, 2.7 Hz, 1H), 7.03 (d, J=2.4 Hz, 1H), 4.78-4.73 (m, 1H), 4.11-4.02 (m, 2H), 3.95-3.86 (m, 2H), 3.80 (s, 3H), 2.47-2.39 (m, 1H), 2.08-2.02 (m, 1H).

Examples 75-1 to 75-11 in the following table were prepared using the procedures detailed above. Unless completely shown, compounds have the following general structure with variable XX$_1$ defined in the table.

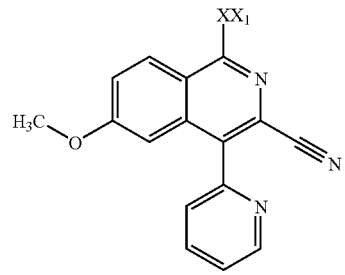

| | | | |
|---|---|---|---|
| 75-1 | XX$_1$ is 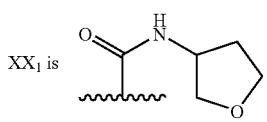 | 375.1446 | (+/−)-3-cyano-6-methoxy-4-pyridin-2-yl-N-tetrahydrofuran-3-ylisoquinoline-1-carboxamide |
| 75-2 | XX$_1$ is 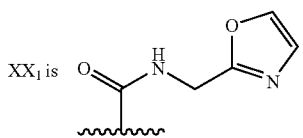 | 386.1239 | 3-cyano-6-methoxy-N-(1,3-oxazol-2-ylmethyl)-4-pyridin-2-ylisoquinoline-1-carboxamide |
| 75-3 | 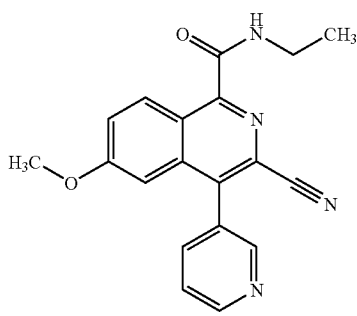 | 333.1343 | 3-cyano-N-ethyl-6-methoxy-4-pyridin-3-ylisoquinoline-1-carboxamide |
| 75-4 | 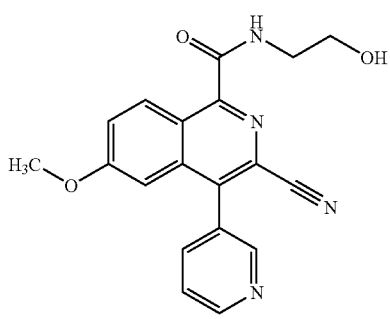 | 349.1291 | 3-cyano-N-(2-hydroxyethyl)-6-methoxy-4-pyridin-3-ylisoquinoline-1-carboxamide |

-continued

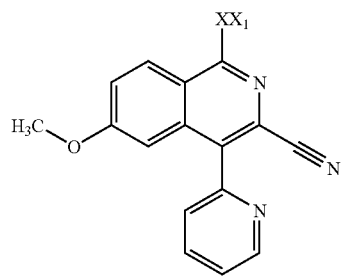

| | | | |
|---|---|---|---|
| 75-5 | 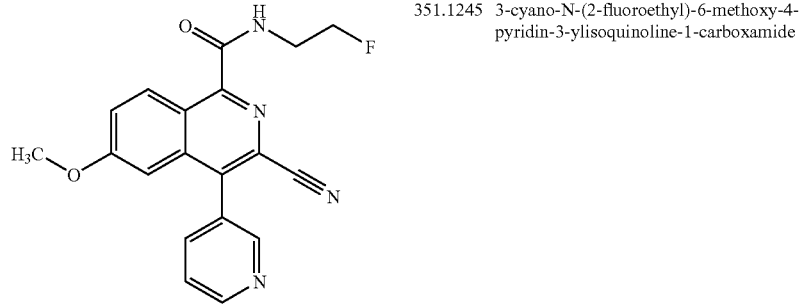 | 351.1245 | 3-cyano-N-(2-fluoroethyl)-6-methoxy-4-pyridin-3-ylisoquinoline-1-carboxamide |
| 75-6 | 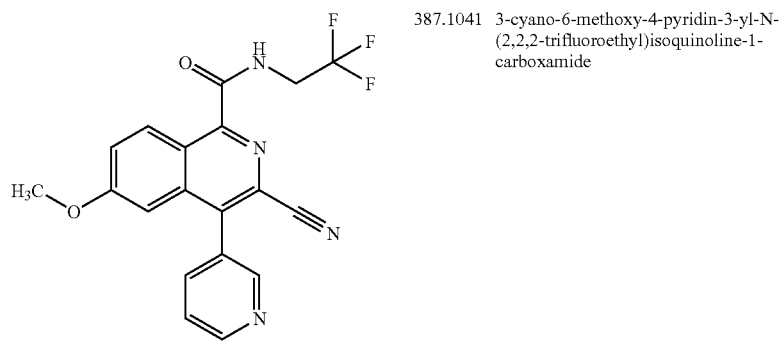 | 387.1041 | 3-cyano-6-methoxy-4-pyridin-3-yl-N-(2,2,2-trifluoroethyl)isoquinoline-1-carboxamide |
| 75-7 | 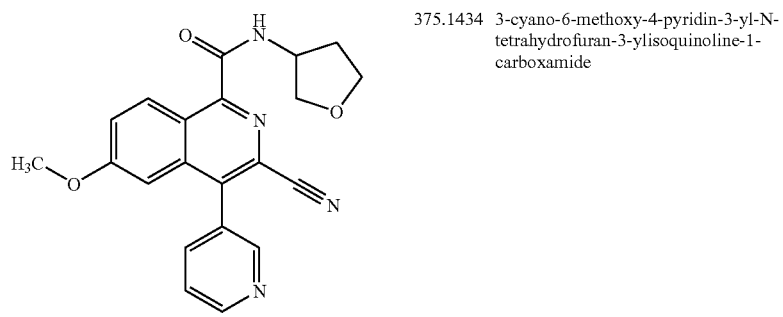 | 375.1434 | 3-cyano-6-methoxy-4-pyridin-3-yl-N-tetrahydrofuran-3-ylisoquinoline-1-carboxamide |
| 75-8 | $XX_1$ is 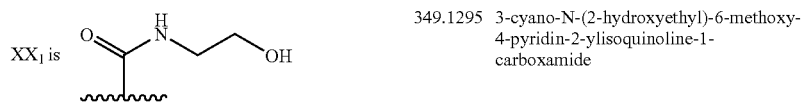 | 349.1295 | 3-cyano-N-(2-hydroxyethyl)-6-methoxy-4-pyridin-2-ylisoquinoline-1-carboxamide |
| 75-9 | $XX_1$ is 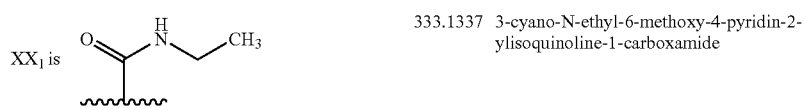 | 333.1337 | 3-cyano-N-ethyl-6-methoxy-4-pyridin-2-ylisoquinoline-1-carboxamide |
| 75-10 | $XX_1$ is 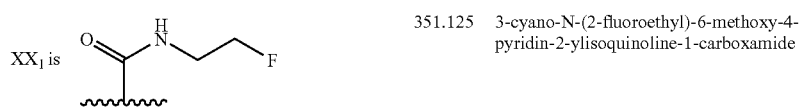 | 351.125 | 3-cyano-N-(2-fluoroethyl)-6-methoxy-4-pyridin-2-ylisoquinoline-1-carboxamide |

-continued

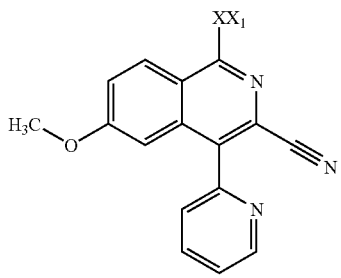

| 75-11 | 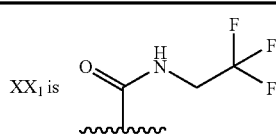<br>XX₁ is | 387.106 | 3-cyano-6-methoxy-4-pyridin-2-yl-N-(2,2,2-trifluoroethyl)isoquinoline-1-carboxamide |
|---|---|---|---|

EXAMPLE 76

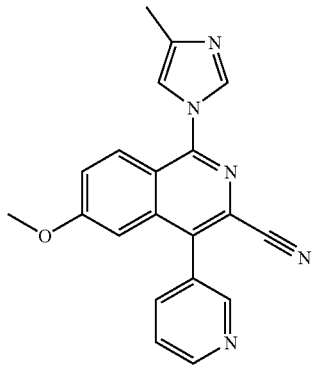

6-methoxy-1-(4-methyl-1H-imidazol-1-yl)-4-pyridin-3-ylisoquinoline-3-carbonitrile Step, A. 2-hydroxy-4-methoxybenzoyl chloride To a solution of 2-hydroxy-4-methoxybenzoic acid (20 g, 118.9 mmol) in 500 mL $CH_2Cl_2$ was added thionyl chloride (21.2 g, 178.4 mmol), followed by 0.4 mL DMF. After stirring at rt for 8 h, the reaction mixture was concentrated to a white solid (azeotroped twice from benzene). This material was used as is in the next step.

Step B. N-(cyanomethyl)-2-hydroxy-4-methoxy-N-methylbenzamide

To a solution of 2-hydroxy-4-methoxybenzoyl chloride (22.19 g, 118.9 mmol) in 500 $CH_2Cl_2$ were added (methylamino)acetonitrile (10 g, 142.7 mmol) and 2,6-lutidine (19.1 g, 178.4 mmol). The reaction was stirred at rt overnight. The reaction mixture was then partitioned between EtOAc and 1(N) aq HCl. Organic layer washed with 1(N) aq HCl (2×), dried over $Na_2SO_4$ and concentrated to light yellow viscous material (24.63 g, 94%). This material was used in the next step without further purification.

Step C. 2-{[(cyanomethyl)(methyl)amino]carbon}-5-methoxyphenyl trifluoromethanesulfonate Hunig's base (21.7 g, 167.6 mmol) was added to a solution of N-cyanomethyl)-2-hydroxy-4-methoxy-N-methylbenzamide (24.6 g, 111.7 mmol) in 300 mL. The mixture was then cooled to 0° C. N-Phenyltriflimide (59.9 g, 167.6 mmol) was added and stirred at rt over the weekend. The reaction mixture was concentrated and purified by flash chromatography (10% to 80% EtOAc in hexanes). Pale yellow viscous liquid, not completely pure (28.8 g, 73%).

Step D. Methyl 2-{[(canomethyl)(methyl)amino]carbonyl}-5-methoxybenzoate

To a solution of 2-{[(cyanomethyl)(methyl)amino]carbonyl}-5-methoxyphenyl trifluoromethanesulfonate (28.7 g, 81.5 mmol) in 100 mL DMSO and 50 mL MeOH was added triethylamine (18.9 g, 187.4 mmol). Carbon monoxide gas was bubbled through this solution for 5 min and then $Pd(OAc)_2$ (1.09 g, 4.89 mmol), followed by dppf (5.42 g, 9.78 mmol) were added. This mixture was heated under atmospheric CO-atmosphere at 70° C. for 18 h. Cooled to rt and partitioned between EtOAc and water. Aqueous layer was extracted with EtOAc (2×). Combined organic layers were washed with half-saturated brine, dried over $MgSO_4$ and concentrated. Purified by flash chromatography (10% to 70% EtOAc-MeOH (95:5 v/v) in hexanes. Red viscous liquid (10.3 g, 47%).

Step E. 4-hydroxy-6-methoxy-2-methyl-1-oxo-1,2-dihydroisoquinoline-3-carbonitrile A solution of methyl 2-{[(cyanomethyl)(methyl)amino]carbonyl}-5-methoxybenzoate (10.3 g, 39.27 mmol) in 60 mL MeOH was treated with 17.9 mL of 4.37 (M) methanolic NaOMe solution and heated at reflux for 3.5 h. The reaction mixture was then concentrated and 72 mL 1(M) HCl in ether was added to it. Concentrated again (azeotroped twice from benzene) to give a tan solid (13.5 g, contaminated with NaCl).

Step F. 1,4-dichloro-6-methoxyisoquinoline-3-carbonitrile 4-hydroxy-6-methoxy-2-methyl-1-oxo-1,2-dihydroisoquinoline-3-carbonitrile (1.35 g of crude material, 3.91 mmol), $POCl_3$ (7 mL) and 7 drops of DMF were taken in a sealed tube and heated at 90° C. for 25 h. Then 2 more drops of DMF added and heating at 90° C. continued for another 8 h. Cooled to rt and concentrated. The resulting residue was dissolved in $CH_2Cl_2$ and cooled to 0° C. Aqueous saturated $NaHCO_3$ solution was added slowly while stirring, until the aqueous layer became basic. Layers were separated. Aqueous layer was extracted with $CH_2Cl_2$ (3×). Combined organic layers were dried over $MgSO_4$ and concentrated. Flash chromatography (5% to 35% EtOAc in hexanes) gave 0.393 g of the titled compound as white solid and 0.3 g of monochlorinated intermediate. This intermediate was subjected to same reaction conditions at 110° C. for 40 h and worked up and purified as above to give 210 mg of the titled compound. Combined yield: 0.603 g (60%).

Step G. 4-chloro-6-methoxy-1-(4-methyl-1H-imidazol-1-yl)isoquinoline-3-carbonitrile 1,4-dichloro-6-methoxyisoquinoline-3-carbonitrile (0.25 g, 0.988 mmol) and 4-methylimidazole (0.324 g 3.951 mmol) and 4 mL isopropanol were taken in a sealed tube and heated at 150° C. for 2 h The resulting white solid was dissolved in hot EA-MeOH and dry loaded on a flash column. Flash chromatography (0% to 6% MeOH—NH3 in EA) gave the titled compound as a white solid.

Step H. 6-methoxy-1-(4-methyl-1H-imidazol-1-yl)-4-pyridin-3-ylisoquinoline-3-carbonitrile 4-chloro-6-methoxy-1-(4-methyl-1H-imidazol-1-yl)isoquinoline-3-carbonitrile (0.055 g, 0.184 mmol), 3-pyridylboronic acid (0.034 g, 0.276 mmol), Pd$_2$(dba)$_3$ (0.017 g, 0.018 mmol), tricyclohexylphosphene (0.015 g, 0.055 mmol) and K$_3$PO$_4$ (0.117 g, 0.552 mmol) were taken in 7 mL dry dioxane and heated at 100° C. under argon atmosphere for 22 h. The reaction mixture was filtered through celite and concentrated. To the resulting residue all of the above reagents and 6 mL dioxane were added and then the mixture was heated at 100° C. for 22 h. The reaction was cooled to rt, filtered through celite (washing with CH$_2$Cl$_2$) and the filtrate was concentrated, then purified by flash chromatography: 3% to 6% MeOH—NH$_4$OH (90:10, v/v) in EtOAc. Impure fractions from the flash chromatography were combined and purified by reverse phase HPLC to give a white solid (0.025 g, 40%).

$^1$H NMR (500 MHz, DMSO-d$_6$): δ 8.86 (dd, J=4.9, 1.5 Hz, 1H), 8.84 (d, J=1.9 Hz, 1H), 8.19-8.11 (m, 3H), 7.72 (dd, J=7.8, 4.9 Hz, 1H), 7.64 (dd, J=9.5, 2.7 Hz, 1H), 7.56 (s, 1H), 6.93 (d, J=2.4 Hz, 1H), 3.82 (s, 3H), 2.25 (s, 3H). HRMS 342.1334 (M+H)$^+$.

EXAMPLE 77

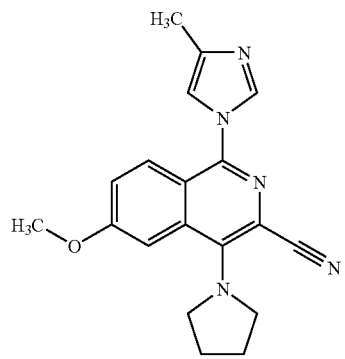

6-methoxy-1-(4-methyl-1H-imidazol-1-yl)-4-pyrrolidin-1-ylisoquinoline-3-carbonitrile 4-chloro-6-methoxy-1-(4-methyl-1H-imidazol-1-yl)isoquinoline-3-carbonitrile (0.010 g, 0.033 mmol) and pyrrolidine (0.048 g, 0.067 mmol) were combined in isopropanol (1 mL) in a sealed tube and heated at 160° C. in a microwave reactor for 1.5 h. Cooled to rt and partitioned between aqueous saturated NaHCO$_3$ and EtOAc. The organic layer was washed with brine (1×), dried over Na$_2$SO$_4$ and concentrated. Purified by r.p. HPLC. The titled compound was obtained as a tan solid (free base, 0.0065 g, 58%). $^1$H NMR (500 MHz, CDCl$_3$): δ 7.95 (d, J=9.0 Hz, 1H), 7.91 (s, 1H), 7.55 (d, J=2.7 Hz, 1H), 7.36 (dd, J=9.3, 2.7 Hz, 1H), 7.18(s, 1 H), 4.00 (s, 3H), 3.71-3.69 (m, 4H), 2.19-2.14 (m, 4H). HRMS 334.1666 (M+H)$^+$.

Examples 77-1 to 77-9 were prepared using the procedures detailed above. Unless completely shown, compounds have the following general structure with variable XX$_2$ defined in the table.

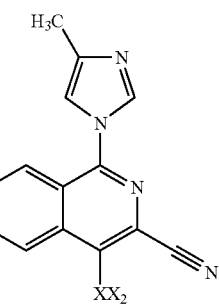

| | | | |
|---|---|---|---|
| 77-1 | 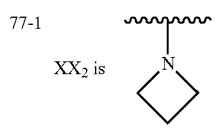 XX$_2$ is | 320.1508 | 4-azetidin-1-yl-6-methoxy-1-(4-methyl-1H-imidazol-1-yl)isoquinoline-3-carbonitrile |
| 77-2 | 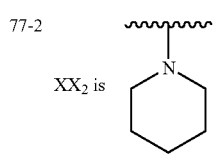 XX$_2$ is | 348.1819 | 6-methoxy-1-(4-methyl-1H-imidazol-1-yl)-4-piperidin-1-ylisoquinoline-3-carbonitrile |

-continued

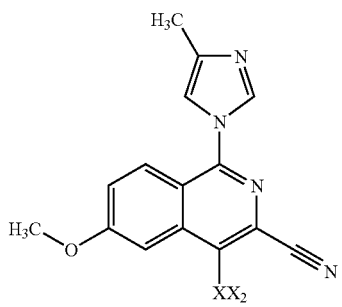

| | | | |
|---|---|---|---|
| 77-3 | XX$_2$ is (3,5-dimethylpiperazin-1-yl) | 377.2076 | 4-(3,5-dimethylpiperazin-1-yl)-6-methoxy-1-(4-methyl-1H-imidazol-1-yl)isoquinoline-3-carbonitrile |
| 77-4 | XX$_2$ is (4-methyl-1H-imidazol-1-yl) | 345.1457 | 6-methoxy-1,4-bis(4-methyl-1H-imidazol-1-yl)isoquinoline-3-carbonitrile |
| 77-5 | XX$_2$ is pyridin-4-yl | 342.134 | 6-methoxy-1-(4-methyl-1H-imidazol-1-yl)-4-pyridin-4-ylisoquinoline-3-carbonitrile |
| 77-6 | XX$_2$ is pyridin-2-yl | 342.1356 | 6-methoxy-1-(4-methyl-1H-imidazol-1-yl)-4-pyridin-2-ylisoquinoline-3-carbonitrile |
| 77-7 | XX$_2$ is 2-aminophenyl | 356.1505 | 4-(2-aminophenyl)-6-methoxy-1-(4-methyl-1H-imidazol-1-yl)isoquinoline-3-carbonitrile |
| 77-8 | XX$_2$ is pyrimidin-2-yl | 343.1304 | 6-methoxy-1-(4-methyl-1H-imidazol-1-yl)-4-pyrimidin-2-ylisoquinoline-3-carbonitrile |
| 77-9 | XX$_2$ is Cl | 299.0698 | 4-chloro-6-methoxy-1-(4-methyl-1H-imidazol-1-yl)isoquinoline-3-carbonitrile |

EXAMPLE 78

Examples 78-1 to 78-8 in the following table were prepared using the procedures above and employing mono-displacement of 1,4-dichloro-6-methoxyisoquinoline-3-carbonitrile with the appropriate alcohol under the conditions of, e.g., Example 24. Unless completely shown, compounds have the following general structure with variable XX$_3$ defined in the table.

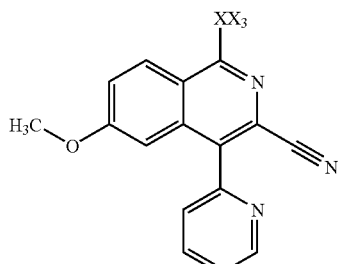
| | | | |
|---|---|---|---|
| 78-1 | XX₃ is 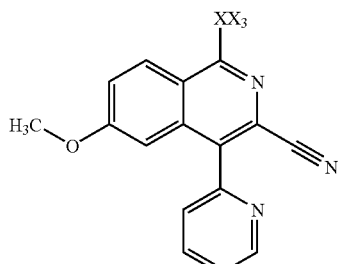 (O-CH₃) | 292.1071 | 1,6-dimethoxy-4-pyridin-2-ylisoquinoline-3-carbonitrile |
| 78-2 | 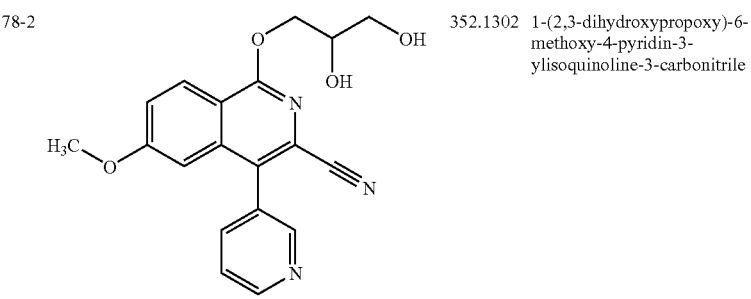 | 352.1302 | 1-(2,3-dihydroxypropoxy)-6-methoxy-4-pyridin-3-ylisoquinoline-3-carbonitrile |
| 78-3 | XX₃ is 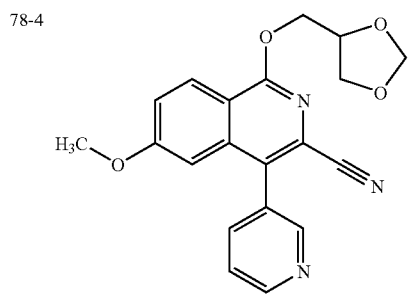 | 352.1304 | 1-(2,3-dihydroxypropoxy)-6-methoxy-4-pyridin-2-lisoquinoline-3-carbonitrile |
| 78-4 | 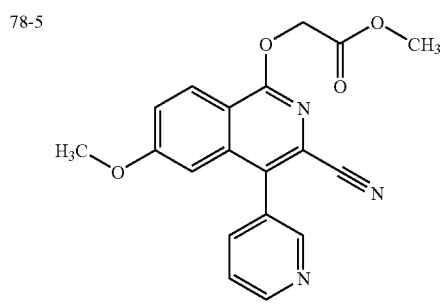 | 364.10 | 1-(1,3-dioxolan-4-ylmethoxy)-6-methoxy-4-pyridin-3-ylisoquinoline-3-carbonitrile |
| 78-5 | | 350.1132 | methyl [(3-cyano-6-methoxy-4-pyridin-3-ylisoquinolin-1-yl)oxy]acetate |

| | | | |
|---|---|---|---|
| | 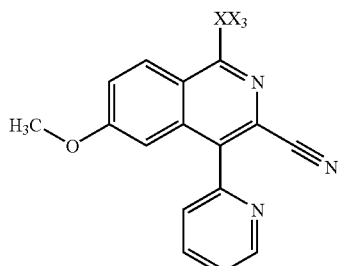 | | |
| 78-6 | 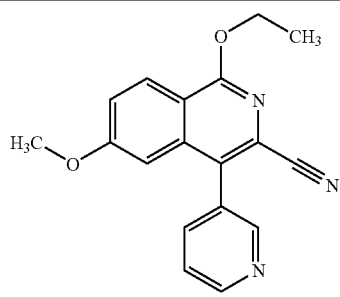 | 306.1235 | 1-ethoxy-6-methoxy-4-pyridin-3-ylisoquinoline-3-carbonitrile |
| 78-7 XX₃ is | 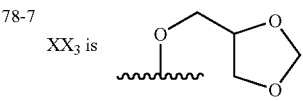 | 364.10 | 1-(1,3-dioxolan-4-ylmethoxy)-6-methoxy-4-pyridin-2-ylisoquinoline-3-carbonitrile |
| 78-8 XX₃ is | 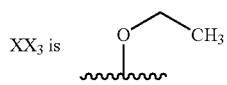 | 306.1233 | 1-ethoxy-6-methoxy-4-pyridin-2-ylisoquinoline-3-carbonitrile |

EXAMPLE 79

Examples 79-1 to 79-2 in the following table were prepared by Suzuki coupling or carbonylation of 1,4-dichloro-6-methoxyisoquinoline-3-carbonitrile according to standard procedures.

| | | | |
|---|---|---|---|
| 79-1 | 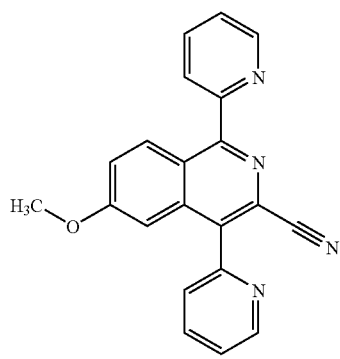 | 339.1249 | 6-methoxy-1,4-dipyridin-2-ylisoquinoline-3-carbonitrile |

| | | | -continued |
|---|---|---|---|
| 79-2 | 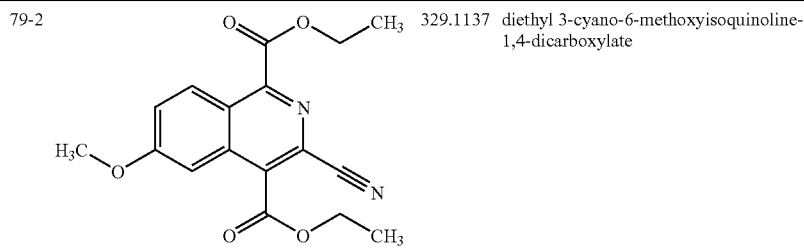 | 329.1137 | diethyl 3-cyano-6-methoxyisoquinoline-1,4-dicarboxylate |

EXAMPLE 80

Examples 80-1 to 80-42 in the following table were prepared using the procedures detailed in the Examples above. Unless completely shown, compounds have the following general structure with variable XX$_4$ defined in the table.

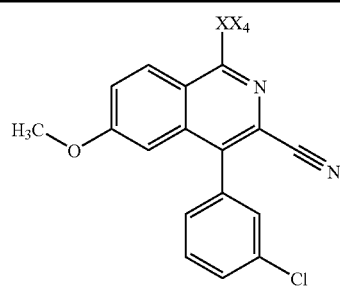

| 80-1 | 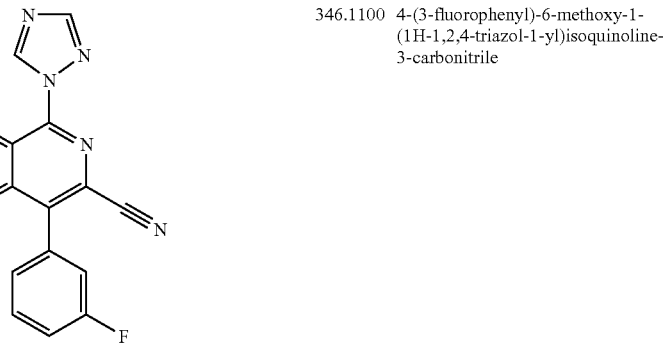 | 346.1100 | 4-(3-fluorophenyl)-6-methoxy-1-(1H-1,2,4-triazol-1-yl)isoquinoline-3-carbonitrile |
| 80-2 | XX$_4$ is 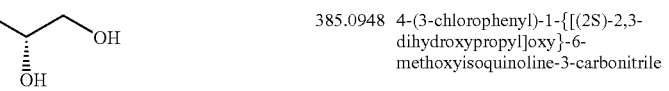 | 385.0948 | 4-(3-chlorophenyl)-1-{[(2S)-2,3-dihydroxypropyl]oxy}-6-methoxyisoquinoline-3-carbonitrile |
| 80-3 | 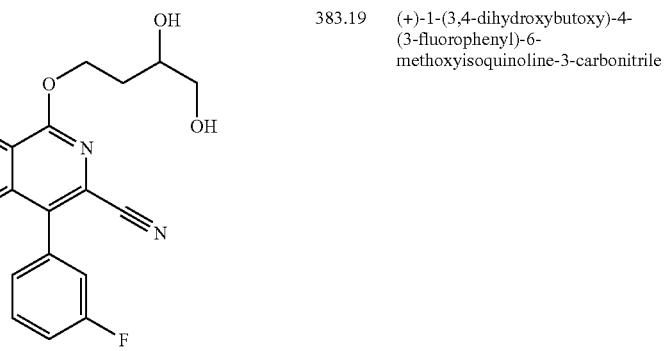 | 383.19 | (+)-1-(3,4-dihydroxybutoxy)-4-(3-fluorophenyl)-6-methoxyisoquinoline-3-carbonitrile |

-continued
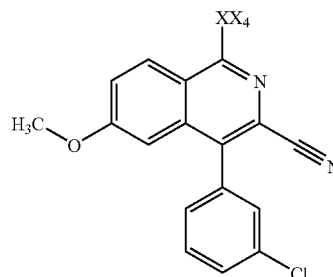
| 80-4 | 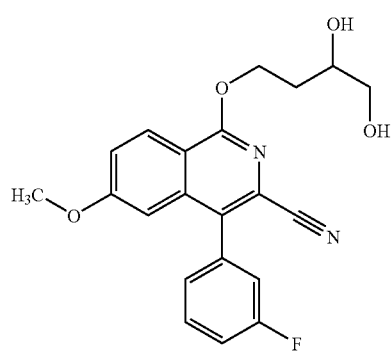 | 383.19 | (−)-1-(3,4-dihydroxybutoxy)-4-(3-fluorophenyl)-6-methoxyisoquinoline-3-carbonitrile |
| 80-5 | 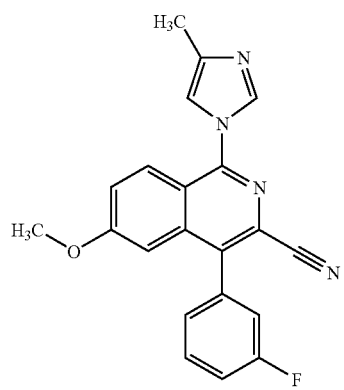 | 359.1301 | 4-(3-fluorophenyl)-6-methoxy-1-4-methyl-1H-imidazol-1-yl)isoquinoline-3-carbonitrile |
| 80-6 | 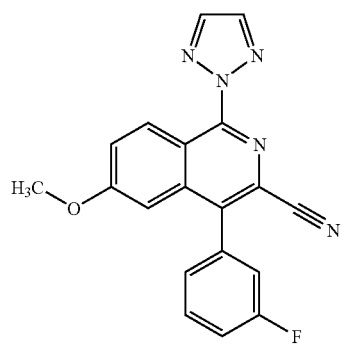 | 346.1115 | 4-(3-fluorophenyl)-6-methoxy-1-(2H-1,2,3-triazol-2-yl)isoquinoline-3-carbonitrile |

-continued
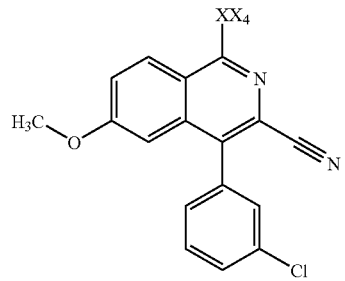
80-7 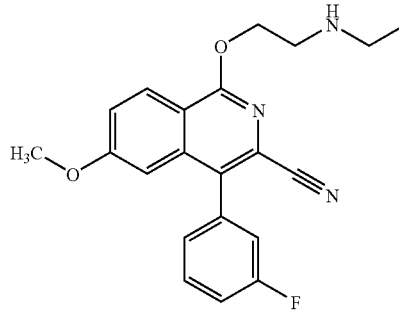 328.1571 4-(3-fluorophenyl)-1-{2-[(2-hydroxyethyl)amino]ethoxy}-6-methoxyisoquinoline-3-carbonitrile
80-8 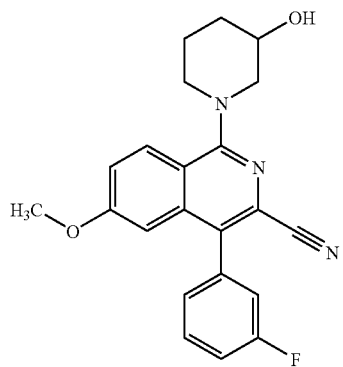 378.1608 4-(3-fluorophenyl)-1-(3-hydroxypiperidin-1-yl)-6-methoxyisoquinoline-3-carbonitrile
80-9 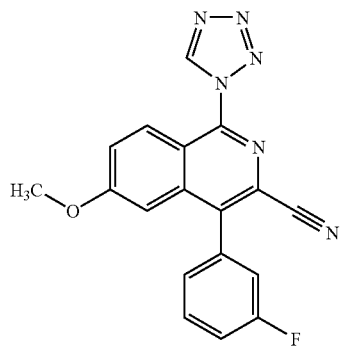 4-(3-fluorophenyl)-6-methoxy-1-(1H-tetraazol-1-yl)isoquinoline-3-carbonitrile
$^1$H NMR (500 MHz, DMSO-$d_6$):
δ 9.50 (s, 1H), 8.64 (d, J=8.8 Hz, 1H), 7.75–7.71 (m, 1H), 7.61 (dd, J=9.0, 2.6, 1H), 7.57–7.51 (m, 2H), 7.48 (d, J=7.6, 1H), 6.80 (d, J=2.44, 1H), 3.79 (s, 3H).

-continued
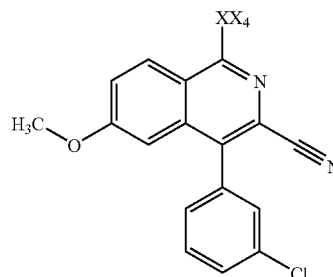
| 80-10 | 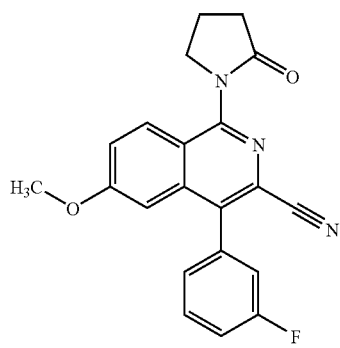 | 362.1298 | 4-(3-fluorophenyl)-6-methoxy-1-(2-oxopyrrolidin-1-yl)isoquinoline-3-carbonitrile |
| --- | --- | --- | --- |
| 80-11 | 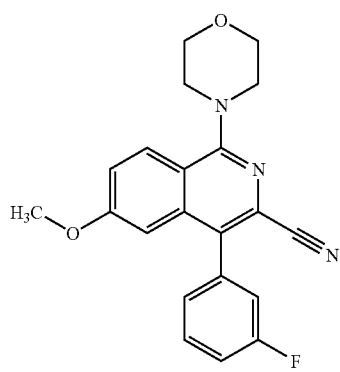 | 364.1453 | 4-(3-fluorophenyl)-6-methoxy-1-morpholin-4-ylisoquinoline-3-carbonitrile |
| 80-12 | XX₄ is 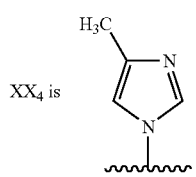 | 375.1 | 4-(3-chlorophenyl)-6-methoxy-1-(4-methyl-1H-imidazol-1-yl)isoquinoline-3-carbonitrile |
| 80-13 | 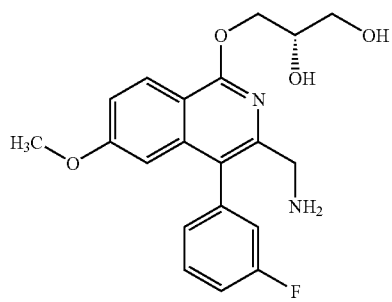 | 373.1561 | (2S)-3-{[3-(aminomethyl)-4-(3-fluorophenyl)-6-methoxyisoquinolin-1-yl]oxy}propane-1,2-diol |

-continued
| | | | |
|---|---|---|---|
| | 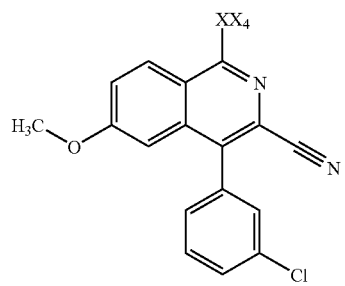 | | |
| 80-14 | 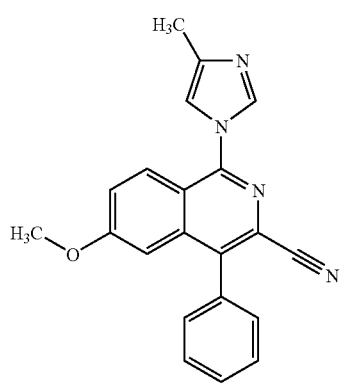 | 341.1387 | 6-methoxy-1-(4-methyl-1H-imidazol-1-yl)-4-phenylisoquinoline-3-carbonitrile |
| 80-15 | 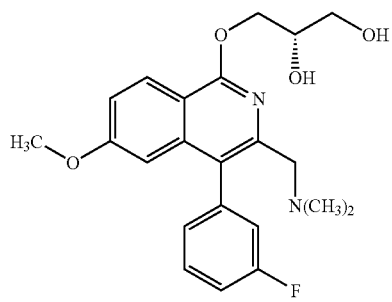 | 401.1864 | (2S)-3-{[3-[(dimethylamino)methyl]-4-(3-fluorophenyl)-6-methoxyisoquinolin-1-yl]oxy}propane-1,2-diol |
| 80-16 | XX$_4$ is 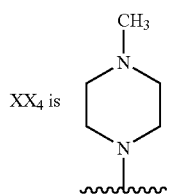 | 393.1469 | 4-(3-chlorophenyl)-6-methoxy-1-(4-methylpiperazin-1-yl)isoquinoline-3-carbonitrile |
| 80-17 | 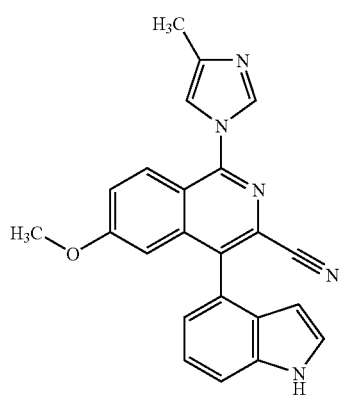 | 380.1493 | 4-(1H-indol-4-yl)-6-methoxy-1-(4-methyl-1H-imidazol-1-yl)isoquinoline-3-carbonitrile |

-continued

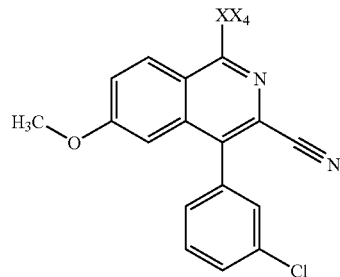

| | | | |
|---|---|---|---|
| 80-18 | XX$_4$ is 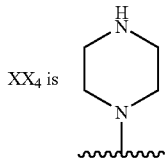 | 379.1309 | 4-(3-chlorophenyl)-6-hydroxy-1-piperazin-1-ylisoquinoline-3-carbonitrile |
| 80-19 | XX$_4$ is 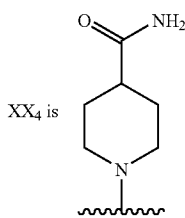 | 421.1423 | 1-[4-(3-chlorophenyl)-3-cyano-6-methoxyisoquinolin-1-yl]piperidine-4-carboxamide |
| 80-20 | XX$_4$ is 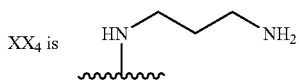 | 367.1322 | 1-[(3-aminopropyl)amino]-4-(3-chlorophenyl)-6-methoxyisoquinoline-3-carbonitrile |
| 80-21 | XX$_4$ is 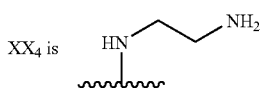 | 353.116 | 1-[(2-aminoethyl)amino]-4-(3-chlorophenyl)-6-methoxyisoquinoline-3-carbonitrile |
| 80-22 | XX$_4$ is 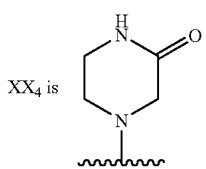 | 393.1115 | 4-(3-chlorophenyl)-6-methoxy-1-(3-oxopiperazin-1-yl)isoquinoline-3-carbonitrile |
| 80-23 | XX$_4$ is 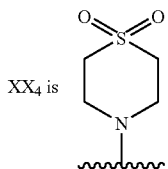 | 428.0831 | 4-(3-chlorophenyl)-1-(1,1-dioxidothiomorpholin-4-yl)-6-methoxyisoquinoline-3-carbonitrile |
| 80-24 | XX$_4$ is 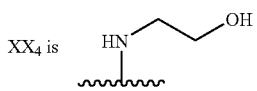 | 354.0991 | 4-(3-chlorophenyl)-1-[(2-hydroxyethyl)amino]-6-methoxyisoquinoline-3-carbonitrile |
| 80-25 | 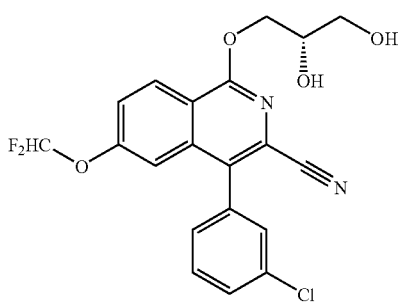 | 421.0771 | 4-(3-chlorophenyl)-6-(difluoromethoxy)-1-{[(2S)-2,3-dihydroxypropyl]oxy}isoquinoline-3-carbonitrile |

-continued

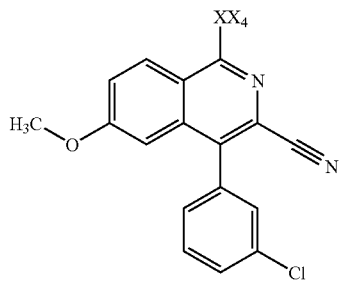

| | | | |
|---|---|---|---|
| 80-26 | XX₄ is 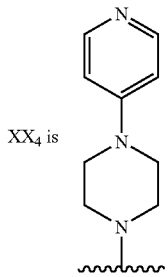 | 456.1580 | 4-(3-chlorophenyl)-6-methoxy-1-(4-pyridin-4-ylpiperazin-1-yl)isoquinoline-3-carbonitrile |
| 80-27 | XX₄ is 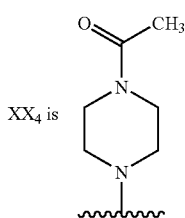 | 421.1419 | 1-(4-acetylpiperazin-1-yl)-4-(3-chlorophenyl)-6-methoxyisoquinoline-3-carbonitrile |
| 80-28 | XX₄ is 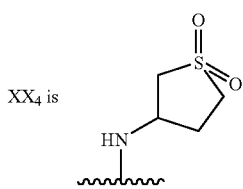 | 428.0800 | 4-(3-chlorophenyl)-1-[(1,1-dioxidotetrahydrothien-3-yl)amino]-6-methoxyisoquinoline-3-carbonitrile |
| 80-29 | XX₄ is 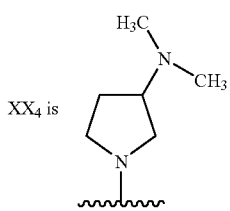 | 407.1628 | 4-(3-chlorophenyl)-1-[3-(dimethylamino)pyrrolidin-1-yl]-6-methoxyisoquinoline-3-carbonitrile |
| 80-30 | XX₄ is 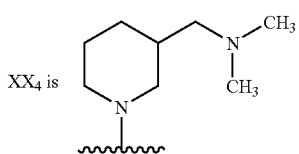 | 435.1942 | 4-(3-chlorophenyl)-1-{3-[(dimethylamino)methyl]piperidin-1-yl}-6-methoxyisoquinoline-3-carbonitrile |
| 80-31 | XX₄ is 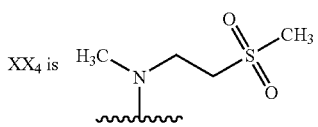 | 430.0977 | 4-(3-chlorophenyl)-6-methoxy-1-{methyl[2-(methylsulfonyl)ethyl]amino}isoquinoline-3-carbonitrile |
| 80-32 | XX₄ is 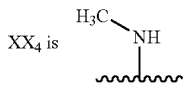 | 324.0889 | 4-(3-chlorophenyl)-6-methoxy-1-(methylamino)isoquinoline-3-carbonitrile |

-continued

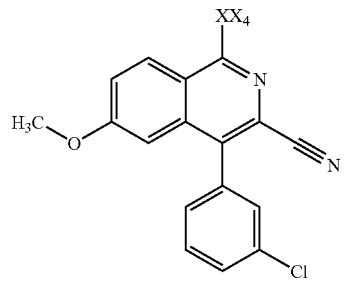

| | | | |
|---|---|---|---|
| 80-33 | XX$_4$ is 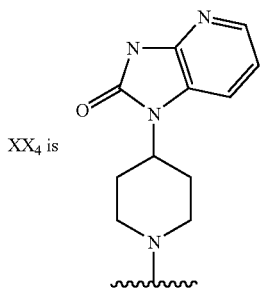 | 511.164 | 4-(3-chlorophenyl)-6-methoxy-1-[4-(2-oxo-2,3-dihydro-1H-imidazo[4,5-b]pyridin-1-yl)piperidin-1-yl]isoquinoline-3-carbonitrile |
| 80-34 | 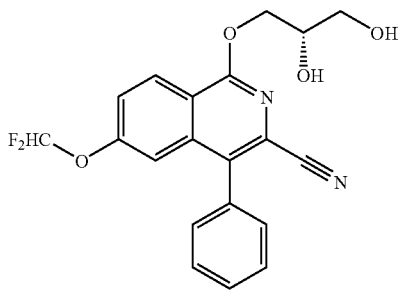 | 387.1133 | 6-(difluoromethoxy)-1-{[(2S)-2,3-dihydroxypropyl]oxy}-4-phenylisoquinoline-3-carbonitrile |
| 80-35 | XX$_4$ is 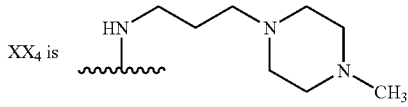 | 450.2054 | 4-(3-chlorophenyl)-6-methoxy-1-{[3-(4-methylpiperazin-1-yl)propyl]amino}isoquinoline-3-carbonitrile |
| 80-36 | XX$_4$ is 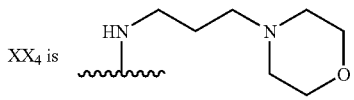 | 437.1738 | 4-(3-chlorophenyl)-6-methoxy-1-[(3-morpholin-4-ylpropyl)amino]isoquinoline-3-carbonitrile |
| 80-37 | XX$_4$ is 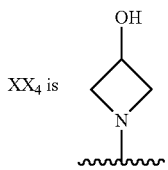 | 366.0995 | 4-(3-chlorophenyl)-1-(3-hydroxyazetidin-1-yl)-6-methoxyisoquinoline-3-carbonitrile |
| 80-38 | 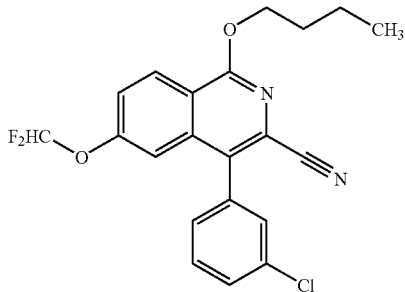 | 403.0998 | 1-butoxy-4-(3-chlorophenyl)-6-(difluoromethoxy)isoquinoline-3-carbonitrile |

-continued
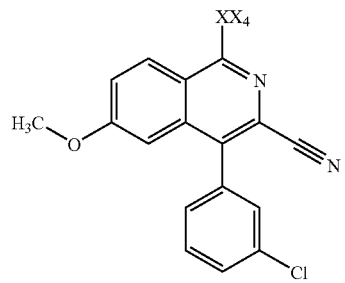
| 80-39 | 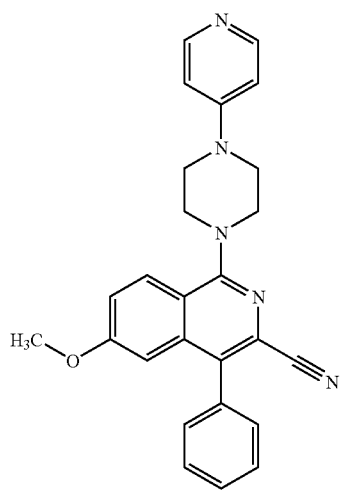 | 422.1949 | 6-methoxy-4-phenyl-1-(4-pyridin-4-ylpiperazin-1-yl)isoquinoline-3-carbonitrile |
| --- | --- | --- | --- |
| 80-40 | 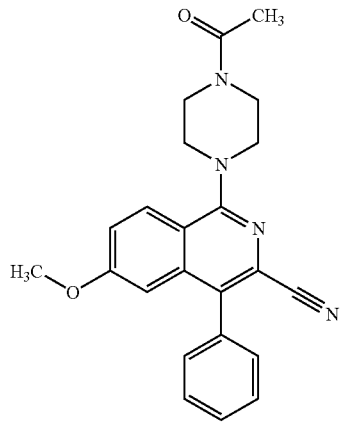 | 387.1821 | 1-(4-acetylpiperazin-1-yl)-6-methoxy-4-phenylisoquinoline-3-carbonitrile |
| 80-41 | 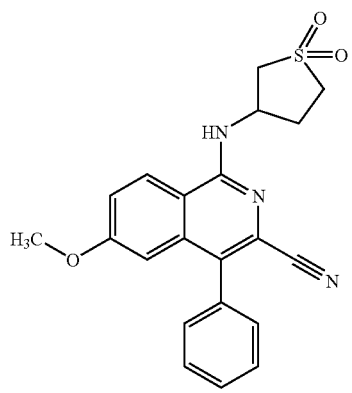 | 394.1228 | 1-[(1,1-dioxidotetrahydrothien-3-yl)amino]-6-methoxy-4-phenylisoquinoline-3-carbonitrile |

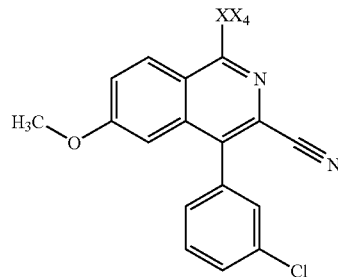

| 80-42 | 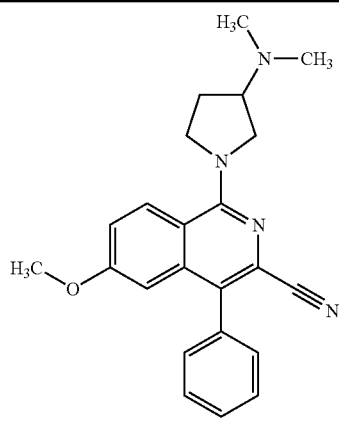 | 373.2022 | 1-[3-(dimethylamino)pyrrolidin-1-yl]-6-methoxy-4-phenylisoquinoline-3-carbonitrile |
|---|---|---|---|

Kv1.5 Assays

The high throughput Kv1.5 planar patch clamp assay is a systematic primary screen. It confirms activity and provides a functional measure of the potency of agents that specifically affect Kv1.5 potassium channels. Kiss et al. (Assay and Drug Dev. Tech., 1(1-2): 127-135,2003) and Schroeder et al. (J. of Biomol. Screen., 8(1);50-64, 2003) describe the use of this instrument for Kv1.5 as well as other voltage gated ion channels.

Chinese hamster ovary cells (CHO) stably expressing the human Kv1.5 potassium channel alpha subunit, cloned from human heart, are grown to 90-100% confluence in Ham's F12 medium supplemented with 10% FBS, 100 U/ml penicillin, 100 μg/ml streptomycin, 1000 μg/ml G-418 sulfate. Cells are subcultured by treatment with Versene, then suspended in phosphate-buffered saline (PBS) and centrifuged The cell pellet is resuspended in PBS and the resulting suspension placed in the cell reservoir of the IonWorks™ HT instrument.

Electrophysiological recordings are performed with intracellular solution containing (mM): K-gluconate 100, KCl 40, $MgCl_2$ 3.2, EGTA 3, N-2-hydroxylethylpiperazine-$N^1$-2-ethanesulphonic acid (HEPES) 5, adjusted to pH 7.3. Amphotericin (Sigma) is prepared as 30 mg/ml stock solution and diluted to a final working concentration of 0.1 mg/ml in internal buffer solution. The external solution is Dulbecco's PBS (Invitrogen) and contains (mM): $CaCl_2$ 0.90, KCl 2.67, $KPO_4$ 1.47, $MgCl_2$ 0.50, NaCl 138, $NaPO_4$ 8.10 and has a pH of 7.4. All compounds are prepared as 10 mM stock solutions in DMSO. Compounds are diluted into external buffer, then transferred from the drug plate to the Patchplate during the experiment (final DMSO concentration <0.66% vol.).

Kv1.5 ionic currents are recorded at room temperature. Membrane currents are amplified (RMS ~10 pA) and sampled at 10 kHz. Leak subtraction was performed in all experiments by applying a 160 ms hyperpolarizing (10 mV) pre-pulses 200 ms before the test pulses to measure leak conductance. The patch clamp stimulus protocol is as follows:

1. Patchplate wells are loaded with 3.5 μL of external buffer.
2. Planar micropipette hole resistances (Rp) is determined by applying a 10 mV, 160 ms potential difference across each hole (Hole test).
3. Cells are pipetted into the Patchplate and form high resistance seals with the 1-2 μm holes at the bottom of each Patchplate well. A seal test scan is performed to determine how many of the Patchplate wells have cells that have formed seals.
4. In order to gain electrical access to the cells, intracellular solution containing amphotericin is circulated for 4 minutes on the bottom side of the Patchplate.
5. Pre-compound addition test pulse is applied to each well on the Patchplate. Protocol: Cells are voltage clamped at a membrane holding potential of −80 mV for 15 seconds. This is followed by application of a 5 Hz stimulus train (27×150 ms depolarizations to +40 mV). The membrane potential steps to +40 mV evoke outward (positive) ionic currents.
6. Compound is added to each well of the Patchplate. Compounds are allowed to incubate for 5 minutes.
7. Post-compound addition test pulse protocol is applied. Protocol: Cells are voltage clamped at a membrane holding potential of −80 mV for 15 seconds. This is followed by application of a 5 Hz stimulus train (27×150 ms depolarizations to +40 mV).

Data analysis is conducted off-line. Paired comparisons between pre-drug and post-drug additions are used to determine the inhibitory effect of each compound. % inhibition of the peak control current during the $27^{th}$ depolarization to +40 mV (in the 5 Hz train) is plotted as a function of antagonist concentration. The concentrations of drug required to inhibit current by 50% ($IC_{50}$) are determined by fitting of the Hill equation to the concentration response data: % of Control=$100\times(1+([Drug]/IC_{50})^p)^{-1}$ For each cell four arithmetic metrics are obtained:
1) seal resistance
2) baseline metric (the mean current at −70 mV from 5 to 45 ms before the first depolarization to +40 mV)
3) current run up metric (pre-compound mean current amplitude during the $1^{st}$ depolarization to +40 mV minus the pre-compound mean current amplitude during the 27 h depolarization to +40 mV)
4) peak current (maximum current amplitude during the 27 h depolarization to +40 mV during the 5 Hz train).

All metrics are obtained during both the pre- and post-compound addition traces. Cells are eliminated from further analysis if:
1) seal resistance is <50 MΩ
2) baseline metric is >±100 pA during the pre-compound
3) current run up metric is >−0.2 nA
4) pre-read peak metric is <400 pA.

The above-listed compounds provide ≧50% inhibition at a concentration of 33 μM or less in the high throughput Kv1.5 planar patch clamp assay described above.

Atomic Absorption Spectroscopy Protocol:

This assay identifies agents that specifically block the human Kv1.5 $K^+$ channel heterologously expressed in CHO cells as measured by $Rb^+$ efflux using Flame Atomic Absorption Spectroscopy (FAAS). The application of FAAS for measuring ion channel activity was adapted from Terstappen et al, *Anal. Biochem.*, 272:149-155, 1999.

CHO cells expressing human Kv1.5 are cultured as described above, then harvested with trypsin-EDTA and washed with medium.
1. 40,000 cells per well are seeded in a 96-well cell culture plate (assay plate) and the cells are allowed to grow for 48 hours at 37° C.
2. The medium is removed and 200 μl of Rb Load Buffer (Aurora Biomed, Vancouver, BC) is added for 3 hours at 37° C. under 5% $CO_2$.
3. The cells are washed 5 times with 200 μl Hank's Balanced Salt Solution (HBSS) followed by the addition of 100 μl HBSS containing test compound or 0.5% DMSO.
4. After 10 min, 100 μl of HEPES-buffered saline containing 140 mM KCl is added and plate is incubated at RT for 5 min. with gentle shaking.
5. Immediately thereafter, 150 μl of supernatant is transferred to a fresh 96 well plate and the remaining supernatant aspirated.
6. 120 μl of Cell Lysis Buffer (Aurora Biomed, Vancouver, BC) is added to the assay plate and shaken for 10 min. prior to analysis.
7. Rb content is measured in samples of supernatant (SUP) and lysate (LYS) using an ICR-8000 automated AAS instrument (Aurora Biomed, Vancouver, BC).

% FLUX=100% *(SUP/(LYS+SUP)). % INH=100% *(1−(A−B)/(C−B)), where A is % FLUX in the presence of tested compound, B is % FLUX in the presence of 10 mM (6-methoxy-2-methyl-1-oxo-4-phenyl-1,2-dihydroisoquinolin-3-yl)-N,N-dimethylmethanaminium chloride, C is % FLUX in the presence of 0.25% DMSO.

The above-listed compounds provide ≧25% inhibition at a concentration of 25 μM or less in the AAS assay described above.

The compounds of this invention can be administered for the treatment or prevention of afflictions, diseases and illnesses according to the invention by any means that effects contact of the active ingredient compound with the site of action in the body of a warm-blooded animal. For example, administration, can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1-500 milligrams per day. Ordinarily, from 10 to 100 milligrams per day in one or more applications is effective to obtain desired results. These dosages are the effective amounts for the treatment and prevention of afflictions, diseases and illnesses described above, e.g., cardiac arrhythmias such as atrial fibrillation, atrial flutter, atrial arrhythmia, and supraventricular tachycardia, thromboembolic events such as stroke and congestive heart failure, and immunodepression.

The active ingredient can be administered orally in solid dosage forms, such as capsules, tablets, troches, dragees, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylve glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Compounds of the invention can be administered as the sole active ingredient or in combination with a second active ingredient, including other antiarrhythmic agents having Kv1.5 blocking activities such as quinidine, propafenone, ambasilide, amiodarone, flecainide, sotalol, bretylium, dofetilide, almokalant, bepridil, clofilium, other compounds having Kv1.5 blocking activities such as clotrimazole, ketoconazole, bupivacaine, erythromycin, verapamil, nifedipine, zatebradine, bisindolylmaleimide, or other cardiovascular agents such as, but not limited to, ACE inhibitors such as benazepril, captopril, enalapril, fosinopril, lisinopril, moexipril, perindopril erbumine, quinapril, ramipril, and trandolapril, angiotensin II antagonists such as candesartan, eprosartan, irbesartan, losartan, olmesartan, telmisartan, and valsartan, cardiac glycosides such as digoxin, L-type calcium channel blockers, T-type calcium channel blockers, selective and nonselective beta blockers, an immunosuppresant compound, endothelin antagonists, thrombin inhibitors, aspirin, nonselective NSAIDs other than aspirin such as naproxen, warfarin, factor Xa inhibitors, low molecular weight heparin, unfractionated heparin, clopidogrel, ticlopidine, IIb/IIIa receptor antagonists such as tirofiban, 5HT receptor antagonists, integrin receptor antagonists, thromboxane receptor antagonists, TAFI inhibitors and P2T receptor antagonists. Compounds of the invention can also be administered as the sole active ingredient or in combination with a pacemaker or defibrillator device.

What is claimed is:

1. A compound of formula I

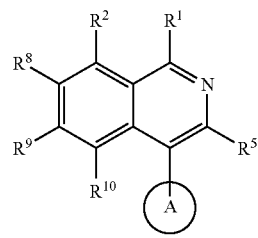

or a pharmaceutically acceptable salt, wherein:
A is
a) an aryl ring selected from phenyl, wherein any stable phenyl ring atom is independently unsubstituted or substituted with
1) halogen,
2) $NO_2$,
3) CN,
4) $CR^{46}=C(R^{47}R^{48})_2$,
5) $C\equiv CR^{46}$,
6) $(CR^iR^j)_rOR^{46}$,
7) $(CR^iR^j)_rN(R^{46}R^{47})$,
8) $(CR^iR^j)_rC(O)R^{46}$,
9) $(CR^iR^j)_rC(O)OR^{46}$,
10) $(CR^iR^j)_rR^{46}$,
11) $(CR^iR^j)_rS(O)_{0-2}R^{61}$,
12) $(CR^iR^j)_rS(O)_{0-2}N(R^{46}R^{47})$,
13) $OS(O)_{0-2}R^{61}$,
14) $N(R^{46})C(O)R^{47}$,
15) $N(R^{46})S(O)_{0-2}R^{61}$,
16) $(CR^iR^j)_rN(R^{46})R^{61}$,
17) $(CR^iR^j)_rN(R^{46})R^{61}OR^{47}$,
18) $(CR^iR^j)_rN(R^{46})(CR^kR^1)_sC(O)N(R^{47}R^{48})$,
19) $N(R^{46})(CR^iR^j)_rR^{61}$,
20) $N(R^{46})(CR^iR^j)_rN(R^{47}R^{48})$,
21) $(CR^iR^j)_rC(O)N(R^{47}R^{48})$,
22) oxo,
b) a heteroaryl ring selected from the group consisting of pyridine, pyrimidine, pyrazine, pyridazine, indole, pyrrolopyridine, benzimidazole, benzoxazole, benzothiazole, and benzoxadiazole
wherein any stable S heteroaryl ring atom is unsubstituted or mono- or di-substituted with oxo, and any stable C or N heteroaryl ring atom is independently unsubstituted or substituted with
1) halogen,
2) $NO_2$,
3) CN,
4) $CR^{46}=C(R^{47}R^{48})_2$,
5) $C \equiv CR^{46}$,
6) $(CR^iR^j)_rOR^{46}$,
7) $(CR^iR^j)_rN(R^{46}R^{47})$,
8) $(CR^iR^j)_rC(O)R^{46}$,
9) $(CR^iR^j)_rC(O)OR^{46}$,
10) $(CR^iR^j)_rR^{46}$,
11) $(CR^iR^j)_rS(O)_{0-2}R^{61}$,
12) $(CR^iR^j)_rS(O)_{0-2}N(R^{46}R^{47})$,
13) $OS(O)_{0-2}R^{61}$,
14) $N(R^{46})C(O)R^{47}$,
15) $N(R^{46})S(O)_xR^{61}$,
16) $(CR^iR^j)_rN(R^{46})R^{61}$,
17) $(CR^iR^j)_rN(R^{46})R^{61}OR^{47}$,
18) $(CR^iR^j)_rN(R^{46})(CR^kR^l)_sC(O)N(R^{47}R^{48})$,
19) $N(R^{46})(CR^iR^j)_rR^{61}$,
20) $N(R^{46})(CR^iR^j)_rN(R^{47}R^{48})$,
21) $(CR^iR^j)_rC(O)N(R^{47}R^{48})$, or
22) oxo, or c) a 4-, 5- or 6-membered heterocyclic ring containing 1 or 2 nitrogen atoms, unsubstituted, mono-substituted or di-substituted with $C_1$-$C_6$ alkyl;

Y is $CH_2$, $NR^{53}$, $NC(O)R^{53}$, $S(O)_{0-2}$ or O;
G is $H_2$ or O;
$R^a$, $R^b$, $R^i$, $R^j$, $R^k$, and $R^l$ are independently selected from the group consisting of:
1) hydrogen,
2) $C_1$-$C_6$ alkyl,
3) halogen,
4) aryl,
5) $R^{80}$,
6) $C_3$-$C_{10}$ cycloalkyl, and
7) $OR^4$,
said alkyl, aryl, and cycloalkyl being unsubstituted, mono-substituted with $R^7$, disubstituted with $R^7$ and $R^{15}$, trisubstituted with $R^7$, $R^{15}$ and $R^{16}$, or tetrasubstituted with $R^7$, $R^{15}$, $R^{16}$, and $R^{17}$;
$R^1$ is independently selected from:
1) hydrogen,
2) halogen,
3) CN,
4) $OR^{40}$,
5) $N(R^{40}R^{41})$,
6) $C(O)OR^{40}$,
7) $R^{81}$,
8) $S(O)_{0-2}R^6$,
9) $N(R^{40})(CR^aR^b)_nR^6$, wherein $R^6=R^{83}$,
10) $N(R^{40})(CR^aR^b)_nN(R^{41}R^{42})$,
11)

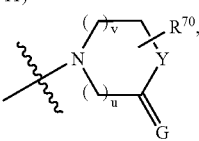

12)

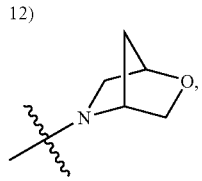

13) $C(O)N(R^{41}R^{42})$, and
14) a 4-, 5-, or 6-membered heterocyclic ring containing 1 nitrogen atom, unsubstituted, or mono-, di- or tri-substituted with —OH, $R^2$, $R^8$, and $R^{10}$ are independently selected from hydrogen and halogen;
$R^9$ is $OCH_3$ or $OCHF_2$,
$R^4$, $R^{40}$, $R^{41}$, $R^{42}$, $R^{46}$, $R^{47}$, $R^{48}$, $R^{49}$, $R^{50}$, $R^{51}$, $R^{52}$, and $R^{53}$ are independently selected from:
1) hydrogen,
2) $C_1$-$C_6$ alkyl,
3) $C_3$-$C_{10}$ cycloalkyl,
4) aryl,
5) $R^{81}$,
6) $CF_3$,
7) $C_2$-$C_6$ alkenyl, and
8) $C_2$-$C_6$ alkynyl,
said alkyl, aryl, and cycloalkyl is unsubstituted, mono-substituted with $R^{18}$, di-substituted with $R^{18}$ and $R^{19}$, tri-substituted with $R^{18}$, $R^{19}$ and $R^{20}$, or tetra-substituted with $R^{18}$, $R^{19}$, $R^{20}$ and $R^{21}$;
$R^5$ is independently selected from:
1) hydrogen,
2) halogen,
3) CN,
4) $C(O)N(R^{49}R^{50})$,
5) $C(O)OR^{49}$,
6) $S(O)_{0-2}N(R^{49}R^{50})$,
7) $S(O)_{0-2}R^{62}$,
8) $C_1$-$C_6$ alkyl,
9) $C_3$-$C_{10}$ cycloalkyl,
10) $R^{82}$,
said alkyl, aryl, and cycloalkyl is unsubstituted, mono-substituted with $R^{22}$, di-substituted with $R^{22}$ and $R^{23}$, tri-substituted with $R^{22}$, $R^{23}$ and $R^{24}$, or tetra-substituted with $R^{22}$, $R^{23}$, $R^{24}$ and $R^{25}$;
$R^6$, $R^{61}$, $R^{62}$ and $R^{63}$ are independently selected from:
1) $C_1$-$C_6$ alkyl,
2) aryl,
3) $R^{83}$, and
4) $C_3$-$C_{10}$ cycloalkyl;
said alkyl, aryl, and cycloalkyl is unsubstituted, mono-substituted with $R^{26}$, di-substituted with $R^{26}$ and $R^{27}$, tri-substituted with $R^{26}$, $R^{27}$ and $R^{28}$, or tetra-substituted with $R^{26}$, $R^{27}$, $R^{28}$ and $R^{29}$;
$R^7$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{70}$ are independently selected from:
1) $C_1$-$C_6$ alkyl,
2) halogen,
3) $OR^{51}$,
4) $CF_3$,
5) aryl,
6) $C_3$-$C_{10}$ cycloalkyl,
7) $R^{84}$,
8) $S(O)_{0-2}N(R^{51}R^{52})$, 9) C(O)OR$^{51}$,
10) C(O)R$^{51}$,
11) CN,
12) C(O)N(R$^{51}$R$^{52}$),
13) N(R$^{51}$)C(O)R$^{52}$,
14) S(O)$_{0-2}$R$^{63}$,
15) NO$_2$, and
16) N(R$^{51}$R$^{52}$);

R$^{80}$, R$^{81}$, R$^{82}$, R$^{83}$ and R$^{84}$ are independently selected from a group of unsubstituted or substituted heterocyclic rings consisting of a 4-6 membered unsaturated or saturated monocyclic ring with 1, 2, 3 or 4 heteroatom ring atoms selected from the group consisting N, O and S, and a 9- or 10-membered unsaturated or saturated bicyclic ring with 1, 2, 3 or 4 heteroatom ring atoms selected from the group consisting or N, O or S;

n, r, s and t are independently 0, 1, 2, 3, 4, 5 or 6;
u is 0, 1 or 2; and
v is 0, 1 or 2, wherein said compound is selected from the group consisting of

[(6-methoxy-4-phenylisoquinolin-3-yl)methyl]dimethylamine,
1-(1-chloro-6-methoxy-4-phenylisoquinolin-3-yl)-N,N-dimethylmethanamine,
{[6-methoxy-1-(methylthio)-4-phenylisoquinolin-3-yl]methyl}dimethylamine,
[6-methoxy-1-(methylsulfonyl)-4-phenylisoquinolin-3-yl]methyl(dimethyl)amine oxide,
1-[6-methoxy-1-(methylsulfonyl)-4-phenylisoquinolin-3-yl]-N,N-dimethylmethanamine,
3-[(dimethylamino)methyl]-6-methoxy-4-phenylisoquinoline-1-carbonitrile,
2,3-Dimethyl-6-methoxy-4-phenylisoquinolinium hydroxide,
6-methoxy-1-(2-methoxyethoxy)-3-methyl-4-phenylisoquinoline,
{3-[(6-methoxy-3-methyl-4-phenylisoquinolin-1-yl)oxy]propyl}amine,
2-[(6-methoxy-3-methyl-4-phenylisoquinolin-1-yl)amino]ethanol,
6-methoxy-3-methyl-1-(methylsulfonyl)-4-phenylisoquinoline,
6-methoxy-N-(2-methoxyethyl)-3-methyl-4-phenylisoquinolin-1-amine,
N-(6-methoxy-3-methyl-4-phenylisoquinolin-1-yl)ethane-1,2-diamine,
6-methoxy-3-methyl-4-phenylisoquinoline,
N-(3,4-dimethoxybenzyl)-6-methoxy-3-methyl-4-phenylisoquinolin-1-amine,
6-methoxy-3-methyl-4-phenylisoquinolin-1-amine,
1-(ethylsulfonyl)-6-methoxy-3-methyl-4-phenylisoquinoline,
1-(benzylsulfonyl)-6-methoxy-3-methyl-4-phenylisoquinoline,
6-methoxy-3-methyl-4-phenyl-1-(phenylsulfonyl)isoquinoline,
6-methoxy-3-methyl-4-phenylisoquinoline-1-carbonitrile,
3-tert-butyl-6-methoxy-1-(2-methoxyethoxy)-4-phenylisoquinoline,
1-chloro-6-methoxy-4-phenylisoquinoline-3-carbonitrile,
6-methoxy-4-phenylisoquinoline-1,3-dicarbonitrile,
1-(allyloxy)-6-methoxy-4-phenylisoquinoline-3-carbonitrile,
1-(2,3-dihydroxypropoxy)-6-methoxy-4-phenylisoquinoline-3-carbonitrile,
1-(allylamino)-6-methoxy-4-phenylisoquinoline-3-carbonitrile,
(+/−)-1-[(2,3-dihydroxypropyl)amino]-6-methoxy-4-phenylisoquinoline-3-carbonitrile,
1-{[(2S)-2,3-dihydroxypropyl]amino}-6-methoxy-4-phenylisoquinoline-3-carbonitrile,
1-{[(2R)-2,3-dihydroxypropyl]amino}-6-methoxy-4-phenylisoquinoline-3-carbonitrile,
(+/−)-1-[(2,2-dimethyl-1,3-dioxolan-4-yl)methoxy]-6-methoxy-4-phenylisoquinoline-3-carbonitrile,
1-{[(4S)-2,2-dimethyl-1,3-dioxolan-4-yl]methoxy}-6-methoxy-4-phenylisoquinoline-3-carbonitrile,
1-{[(4R)-2,2-dimethyl-1,3-dioxolan-4-yl]methoxy}-6-methoxy-4-phenylisoquinoline-3-carbonitrile,
1-{[(2R)-2,3-dihydroxypropyl]oxy}-6-methoxy-4-phenylisoquinoline-3-carbonitrile,
1-{[(2S)-2,3-dihydroxypropyl]oxy}-6-methoxy-4-phenylisoquinoline-3-carbonitrile,
(+/−)-1-{[2,3-dihydroxypropyl]oxy}-6-methoxy-4-phenylisoquinoline-3-carbonitrile,
1-[(3R)-3-hydroxypyrrolidin-1-yl]-6-methoxy-4-phenylisoquinoline-3-carbonitrile,
1-[(3S)-3-hydroxypyrrolidin-1-yl]-6-methoxy-4-phenylisoquinoline-3-carbonitrile,
(+/−)-1-[3-hydroxypyrrolidin-1-yl]-6-methoxy-4-phenylisoquinoline-3-carbonitrile,
1-[cis-3,4-dihydroxypyrrolidin-1-yl]-6-methoxy-4-phenylisoquinoline-3-carbonitrile,
6-methoxy-4-phenyl-1-pyrrolidin-1-ylisoquinoline-3-carbonitrile,
6-methoxy-1-(methylsulfonyl)-4-phenylisoquinoline-3-carbonitrile,
6-methoxy-4-phenylisoquinoline-3-carbonitrile,
1,6-dimethoxy-4-phenylisoquinoline-3-carbonitrile,
1-chloro-4-(3-fluorophenyl)-6-methoxyisoquinoline-3-carbonitrile,
4-(3-fluorophenyl)-6-methoxyisoquinoline-3-carbonitrile,
4-(3-fluorophenyl)-6-methoxy-1-methylisoquinoline-3-carbonitrile,
4-(3-fluorophenyl)-1-[(2-hydroxyethyl)amino]-6-methoxyisoquinoline-3-carbonitrile,
1-amino-4-(3-fluorophenyl)-6-methoxyisoquinoline-3-carbonitrile,
4-(3-fluorophenyl)-1-[(3-hydroxypropyl)amino]-6-methoxyisoquinoline-3-carbonitrile,
1-(but-3-enyloxy)-4-(3-fluorophenyl)-6-methoxyisoquinoline-3-carbonitrile,
(+/−)-1-(2,3-dihydroxypropoxy)-4-(3-fluorophenyl)-6-methoxyisoquinoline-3-carbonitrile,
1-[(2R)-2,3-dihydroxypropoxy]-4-(3-fluorophenyl)-6-methoxyisoquinoline-3-carbonitrile,
1-[(2S)-2,3-dihydroxypropoxy]-4-(3-fluorophenyl)-6-methoxyisoquinoline-3-carbonitrile,
(+/−)-1-(3,4-dihydroxybutoxy)-4-(3-fluorophenyl)-6-methoxyisoquinoline-3-carbonitrile,
(+/−)-1-[(3R)-3,4-dihydroxybutoxy]-4-(3-fluorophenyl)-6-methoxyisoquinoline-3-carbonitrile,
1-[(3S)-3,4-dihydroxybutoxy]-4-(3-fluorophenyl)-6-methoxyisoquinoline-3-carbonitrile,
(+/−)-1-[(1,4-dioxan-2-ylmethyl)amino]-4-(3-fluorophenyl)-6-methoxyisoquinoline-3-carbonitrile,
1-[(1,4-dioxan-(2R)-2-ylmethyl)amino]-4-(3-fluorophenyl)-6-methoxyisoquinoline-3-carbonitrile,
1-[(1,4-dioxan-(2S)-2-ylmethyl)amino]-4-(3-fluorophenyl)-6-methoxyisoquinoline-3-carbonitrile, 4-(3-fluorophenyl)-6-methoxy-1-[(1-methyl-1H-imidazol-4-yl)methoxy]isoquinoline-3-carbonitrile, (+/−)-1-(1,3-dioxolan-4-ylmethoxy)-4-(3-fluorophenyl)-6-methoxyisoquinoline-3-carbonitrile, 1-(1,3-dioxolan-(4R)-ylmethoxy)-4-(3-fluorophenyl)-6-methoxyisoquinoline-3-carbonitrile, 1-(1,3-dioxolan-(4S)-4-ylmethoxy)-4-(3-fluorophenyl)-6-methoxyisoquinoline-3-carbonitrile, 1-(1,3-dioxan-5-yloxy)-4-(3-fluorophenyl)-6-methoxyisoquinoline-3-carbonitrile, 4-(3-fluorophenyl)-1-{[2-hydroxy-1-(hydroxymethyl)ethyl]amino}-6-methoxyisoquinoline-3-carbonitrile, 4-(3-fluorophenyl)-1-(1H-imidazol-5-ylmethoxy)-6-methoxyisoquinoline-3-carbonitrile, 1-{[(2R)-2,3-dihydroxypropyl]amino}-4-(3-fluorophenyl)-6-methoxyisoquinoline-3-carbonitrile, 1-{[(2S)-2,3-dihydroxypropyl]amino}-4-(3-fluorophenyl)-6-methoxyisoquinoline-3-carbonitrile, (+/−)-1-{[2,3-dihydroxypropyl]amino}-4-(3-fluorophenyl)-6-methoxyisoquinoline-3-carbonitrile, 1-(1H-imidazol-1-yl)-6-methoxy-4-phenylisoquinoline-3-carbonitrile, 6-methoxy-4-phenyl-1-[(pyridin-2-ylmethyl)amino]isoquinoline-3-carbonitrile, 6-methoxy-4-phenyl-1-[(2-pyridin-2-ylethyl)amino]isoquinoline-3-carbonitrile, (+/−)-1-[(3,4-dihydroxybutyl)amino]-4-(3-fluorophenyl)-6-methoxyisoquinoline-3-carbonitrile, 1-[(3R)-(3,4-dihydroxybutyl)amino]-4-(3-fluorophenyl)-6-methoxyisoquinoline-3-carbonitrile, 1-[(3S)-(3,4-dihydroxybutyl)amino]-4-(3-fluorophenyl)-6-methoxyisoquinoline-3-carbonitrile, 1-chloro-4-(2-fluorophenyl)-6-methoxyisoquinoline-3-carbonitrile, 4-(2-fluorophenyl)-6-methoxyisoquinoline-3-carbonitrile, (+/−)-1-[(2,3-dihydroxypropyl)amino]-4-(2-fluorophenyl)-6-methoxyisoquinoline-3-carbonitrile, 1-[(2S)-(2,3-dihydroxypropyl)amino]-4-(2-fluorophenyl)-6-methoxyisoquinoline-3-carbonitrile, 1-[(2R)-(2,3-dihydroxypropyl)amino]-4-(2-fluorophenyl)-6-methoxyisoquinoline-3-carbonitrile, (+/−)-6-(difluoromethoxy)-1-{[2,3-dihydroxypropyl]amino}-4-(3-fluorophenyl)isoquinoline-3-carbonitrile, 6-(difluoromethoxy)-1-{[(2S)-2,3-dihydroxypropyl]amino}-4-(3-fluorophenyl)isoquinoline-3-carbonitrile, 6-(difluoromethoxy)-1-{[(2R)-2,3-dihydroxypropyl]amino}-4-(3-fluorophenyl)isoquinoline-3-carbonitrile, (+/−)-6-(difluoromethoxy)-1-{[2,3-dihydroxypropyl]oxy}-4-(3-fluorophenyl)isoquinoline-3-carbonitrile, 6-(difluoromethoxy)-1-{[(2S)-2,3-dihydroxypropyl]oxy}-4-(3-fluorophenyl)isoquinoline-3-carbonitrile, 6-(difluoromethoxy)-1-{[(2R)-2,3-dihydroxypropyl]oxy}-4-(3-fluorophenyl)isoquinoline-3-carbonitrile, 1-(4-hydroxypiperidin-1-yl)-6-methoxy-4-phenylisoquinoline-3-carbonitrile, 1-azetidin-1-yl-6-methoxy-4-phenylisoquinoline-3-carbonitrile, (+/−)-1-[trans-3,4-dihydroxypyrrolidin-1-yl]-6-methoxy-4-phenylisoquinoline-3-carbonitrile, 1-[(3R,4R)-3,4-dihydroxypyrrolidin-1-yl]-6-methoxy-4-phenylisoquinoline-3-carbonitrile, 1-[(3S,4S)-3,4-dihydroxypyrrolidin-1-yl]-6-methoxy-4-phenylisoquinoline-3-carbonitrile, and 6-methoxy-N-(3-methoxypropyl)-3-methyl-4-phenylisoquinolin-1-amine.

2. A pharmaceutical formulation comprising a pharmaceutically acceptable carrier and the compound claim 1 or a pharmaceutically acceptable salt thereof.

3. A pharmaceutical composition made by combining the compound of claim 1 and a pharmaceutically acceptable carrier.

* * * * *